US012773271B2

(12) United States Patent
Morgan et al.

(10) Patent No.: US 12,773,271 B2
(45) Date of Patent: Oct. 27, 2026

(54) STERILIZABLE SURGICAL DEVICE WITH BATTERY SWITCH

(71) Applicant: MAKO Surgical Corp., Weston, FL (US)

(72) Inventors: Jonathan Mark Morgan, Biscayne Park, FL (US); Timothy Wade Perez, Plantation, FL (US); Fabian Riegelsberger, Umkirch (DE); Jochen Breisacher, Teningen (DE); Michael Schweizer, Freiburg (DE); Daniel Kühne, Freiburg (DE); Felix Jung, Freiburg (DE); Kana Nishimura, Baden-Baden (DE); Paul Hoekstra, Kalamazoo, MI (US)

(73) Assignee: MAKO Surgical Corp., Weston, FL (US)

( * ) Notice: Subject to any disclaimer, the term of this patent is extended or adjusted under 35 U.S.C. 154(b) by 498 days.

(21) Appl. No.: 18/305,079

(22) Filed: Apr. 21, 2023

(65) Prior Publication Data

US 2023/0338093 A1 Oct. 26, 2023

Related U.S. Application Data

(60) Provisional application No. 63/333,676, filed on Apr. 22, 2022.

(51) Int. Cl.
*A61B 34/20* (2016.01)
*A61B 90/00* (2016.01)

(52) U.S. Cl.
CPC .............. *A61B 34/20* (2016.02); *A61B 90/08* (2016.02); *A61B 2034/2055* (2016.02); *A61B 2034/2068* (2016.02); *A61B 2090/0813* (2016.02)

(58) Field of Classification Search
None
See application file for complete search history.

(56) References Cited

U.S. PATENT DOCUMENTS 1,676,945 A 7/1928 Ellis
4,321,315 A 3/1982 Jensen
(Continued)

FOREIGN PATENT DOCUMENTS

CA 2958013 C 1/2019
CN 102727308 A 10/2012
(Continued)

OTHER PUBLICATIONS

English language abstract and machine-assisted English translation for CN 102727308 A extracted from espacenet.com database on Apr. 24, 2023, 10 pages.
(Continued)

*Primary Examiner* — Deborah L Malamud
(74) *Attorney, Agent, or Firm* — Howard & Howard Attorneys PLLC

(57) ABSTRACT

A surgical tracker assembly for use with a navigation system. The tracker assembly includes a tracker body defining a chamber configured to receive a printed circuit board (PCB) including a plurality of markers that are actively energizable through the PCB. A plurality of openings formed in the tracker body and at least one channel formed in the tracker body extending between the chamber and one of the defined by the tracker body. Each of the markers are visible through one of the plurality of openings of the tracker body. The tracker body is configured to be sterilizable, with the PCB being located within the chamber of the tracker body, and the at least one channel is configured to enable sterilization fluid to enter into and drain from the chamber of the
(Continued)

tracker body during sterilization. The PCB may also include a sterilization resistant protective coating.

19 Claims, 28 Drawing Sheets

(56) References Cited

U.S. PATENT DOCUMENTS

| | | | |
|---|---|---|---|
| 4,622,274 | A | 11/1986 | Lowrance |
| 4,644,244 | A | 2/1987 | Kittelson |
| 4,745,882 | A | 5/1988 | Yarnall, Sr. et al. |
| 4,751,452 | A | 6/1988 | Kilmer et al. |
| 4,842,966 | A | 6/1989 | Omori et al. |
| 4,985,812 | A | 1/1991 | Uke |
| 5,021,305 | A | 6/1991 | Turner |
| 5,070,437 | A | 12/1991 | Roberts, Sr. |
| 5,122,427 | A | 6/1992 | Flowers et al. |
| 5,205,640 | A | 4/1993 | Shin |
| 5,309,913 | A | 5/1994 | Kormos et al. |
| 5,349,506 | A | 9/1994 | Maglica |
| 5,425,330 | A | 6/1995 | Touchton et al. |
| 5,445,166 | A | 8/1995 | Taylor |
| 5,445,900 | A | 8/1995 | Miller, Jr. et al. |
| 5,517,990 | A | 5/1996 | Kalfas et al. |
| 5,564,437 | A | 10/1996 | Bainville et al. |
| 5,572,999 | A | 11/1996 | Funda et al. |
| 5,596,314 | A | 1/1997 | Goldstein |
| 5,598,082 | A | 1/1997 | Gilpin et al. |
| 5,631,098 | A | 5/1997 | Suzuki |
| 5,695,500 | A | 12/1997 | Taylor et al. |
| 5,695,501 | A | 12/1997 | Carol et al. |
| 5,732,703 | A | 3/1998 | Kalfas et al. |
| 5,747,189 | A | 5/1998 | Perkins |
| 5,749,362 | A | 5/1998 | Funda et al. |
| 5,776,064 | A | 7/1998 | Kalfas et al. |
| 5,792,147 | A | 8/1998 | Evans et al. |
| 5,851,183 | A | 12/1998 | Bucholz |
| 5,868,100 | A | 2/1999 | Marsh |
| 5,868,103 | A | 2/1999 | Boyd |
| 5,871,018 | A | 2/1999 | Delp et al. |
| 5,871,445 | A | 2/1999 | Bucholz |
| 5,891,020 | A | 4/1999 | Uber et al. |
| 5,891,157 | A | 4/1999 | Day et al. |
| 5,911,198 | A | 6/1999 | Curen et al. |
| 5,921,992 | A | 7/1999 | Costales et al. |
| 5,923,254 | A | 7/1999 | Brune |
| 5,927,233 | A | 7/1999 | Mainini et al. |
| 5,934,225 | A | 8/1999 | Williams |
| 5,959,557 | A | 9/1999 | Lim |
| 5,967,982 | A | 10/1999 | Barnett |
| 5,976,156 | A | 11/1999 | Taylor et al. |
| 5,984,875 | A | 11/1999 | Brune |
| 5,987,349 | A | 11/1999 | Schulz |
| 6,011,987 | A | 1/2000 | Barnett |
| 6,024,695 | A | 2/2000 | Taylor et al. |
| 6,033,415 | A | 3/2000 | Mittelstadt et al. |
| 6,043,748 | A | 3/2000 | Touchton et al. |
| 6,071,288 | A | 6/2000 | Carol et al. |
| 6,076,008 | A | 6/2000 | Bucholz |
| 6,086,218 | A | 7/2000 | Robertson |
| 6,114,957 | A | 9/2000 | Westrick et al. |
| 6,120,465 | A | 9/2000 | Guthrie et al. |
| 6,126,670 | A | 10/2000 | Walker et al. |
| 6,139,359 | A | 10/2000 | Fuhreck et al. |
| 6,142,937 | A | 11/2000 | Lemcke et al. |
| 6,151,276 | A | 11/2000 | Peinetti |
| 6,161,033 | A | 12/2000 | Kuhn |
| 6,190,395 | B1 | 2/2001 | Williams |
| D439,561 | S | 3/2001 | Lee, IV et al. |
| 6,201,984 | B1 | 3/2001 | Funda et al. |
| 6,220,720 | B1 | 4/2001 | Stephens |
| 6,228,089 | B1 | 5/2001 | Wahrburg |
| 6,231,208 | B1 | 5/2001 | Dalton et al. |
| 6,231,526 | B1 | 5/2001 | Taylor et al. |
| 6,236,875 | B1 | 5/2001 | Bucholz et al. |
| 6,261,300 | B1 | 7/2001 | Carol et al. |
| 6,294,746 | B1 | 9/2001 | Yee |
| 6,333,971 | B2 | 12/2001 | McCrory et al. |
| 6,340,363 | B1 | 1/2002 | Bolger et al. |
| 6,347,240 | B1 | 2/2002 | Foley et al. |
| 6,371,055 | B1 | 4/2002 | Lawrence |
| 6,374,135 | B1 | 4/2002 | Bucholz |
| 6,377,839 | B1 | 4/2002 | Kalfas et al. |
| 6,385,475 | B1 | 5/2002 | Cinquin et al. |
| 6,409,686 | B1 | 6/2002 | Guthrie et al. |
| 6,423,077 | B2 | 7/2002 | Carol et al. |
| 6,434,415 | B1 | 8/2002 | Foley et al. |
| 6,434,507 | B1 | 8/2002 | Clayton et al. |
| 6,450,978 | B1 | 9/2002 | Brosseau et al. |
| 6,453,190 | B1 | 9/2002 | Acker et al. |
| 6,463,319 | B1 | 10/2002 | Bucholz |
| 6,497,134 | B1 | 12/2002 | Faul et al. |
| 6,533,737 | B1 | 3/2003 | Brosseau et al. |
| 6,547,782 | B1 | 4/2003 | Taylor |
| 6,675,040 | B1 | 1/2004 | Cosman |
| 6,678,545 | B2 | 1/2004 | Bucholz |
| 6,694,168 | B2 | 2/2004 | Traxel et al. |
| 6,711,431 | B2 | 3/2004 | Sarin et al. |
| 6,725,079 | B2 | 4/2004 | Zuk et al. |
| 6,725,082 | B2 | 4/2004 | Sati et al. |
| 6,782,285 | B2 | 8/2004 | Birkenbach et al. |
| 6,827,721 | B2 | 12/2004 | Perren et al. |
| 6,838,619 | B1 | 1/2005 | Soyfertis |
| 6,855,152 | B2 | 2/2005 | Suhm et al. |
| 6,859,660 | B2 | 2/2005 | Vilsmeier |
| 6,859,661 | B2 | 2/2005 | Tuke |
| 6,915,150 | B2 | 7/2005 | Cinquin et al. |
| 6,917,295 | B2 | 7/2005 | Groh et al. |
| 6,917,827 | B2 | 7/2005 | Kienzle, III |
| 6,978,166 | B2 | 12/2005 | Foley et al. |
| D515,027 | S | 2/2006 | Groh et al. |
| 7,033,360 | B2 | 4/2006 | Cinquin et al. |
| 7,046,152 | B1 | 5/2006 | Peinetti et al. |
| 7,047,657 | B2 | 5/2006 | Goeggelmann et al. |
| 7,072,704 | B2 | 7/2006 | Bucholz |
| D528,502 | S | 9/2006 | Fleetwood |
| D531,117 | S | 10/2006 | Schrick et al. |
| 7,137,712 | B2 | 11/2006 | Brunner et al. |
| 7,139,601 | B2 | 11/2006 | Bucholz et al. |
| 7,162,292 | B2 | 1/2007 | Ohno et al. |
| 7,208,348 | B2 | 4/2007 | Geng et al. |
| 7,209,776 | B2 | 4/2007 | Leitner |
| 7,237,556 | B2 | 7/2007 | Smothers et al. |
| 7,274,958 | B2 | 9/2007 | Jutras et al. |
| 7,275,547 | B2 | 10/2007 | Willis |
| 7,294,106 | B2 | 11/2007 | Birkenbach et al. |
| 7,302,288 | B1 | 11/2007 | Schellengberg |
| 7,311,714 | B1 | 12/2007 | Wascher |
| 7,319,897 | B2 | 1/2008 | Leitner et al. |
| 7,392,076 | B2 | 6/2008 | Moctezuma de La Barrera |
| 7,447,537 | B1 | 11/2008 | Funda et al. |
| 7,458,977 | B2 | 12/2008 | McGinley et al. |
| 7,477,926 | B2 | 1/2009 | McCombs |
| 7,491,198 | B2 | 2/2009 | Kockro |
| 7,492,930 | B2 | 2/2009 | Leitner et al. |
| 7,493,153 | B2 | 2/2009 | Ahmed et al. |
| D591,232 | S | 4/2009 | Zhuang |
| 7,527,387 | B2 | 5/2009 | Birkenbach |
| 7,541,937 | B2 | 6/2009 | Groh et al. |
| 7,561,051 | B1 | 7/2009 | Kynor et al. |
| 7,613,501 | B2 | 11/2009 | Scherch |
| 7,636,595 | B2 | 12/2009 | Marquart et al. |
| 7,643,862 | B2 | 1/2010 | Schoenefeld |
| 7,649,337 | B2 | 1/2010 | Jehlein-Proctor et al. |
| 7,668,584 | B2 | 2/2010 | Jansen |
| 7,725,162 | B2 | 5/2010 | Malackowski et al. |
| 7,744,605 | B2 | 6/2010 | Vilsmeier et al. |
| 7,744,607 | B2 | 6/2010 | Wascher |
| 7,753,921 | B2 | 7/2010 | Leitner |
| 7,780,677 | B2 | 8/2010 | Leitner |
| D623,589 | S | 9/2010 | Tarter et al. |
| 7,814,816 | B2 | 10/2010 | Alberti et al. |
| 7,820,446 | B2 | 10/2010 | Feilkas et al. |
| 7,822,244 | B2 | 10/2010 | Blumhofer |

(56) References Cited

U.S. PATENT DOCUMENTS

| | | | |
|---|---|---|---|
| 7,822,588 | B2 | 10/2010 | Mueller et al. |
| 7,831,295 | B2 | 11/2010 | Friedrich |
| 7,840,256 | B2 | 11/2010 | Lakin et al. |
| 7,874,686 | B2 | 1/2011 | Rossner et al. |
| 7,877,890 | B2 | 2/2011 | Weber |
| 7,885,701 | B2 | 2/2011 | DiSilvestro et al. |
| 7,970,174 | B2 | 6/2011 | Goldbach |
| 7,983,733 | B2 | 7/2011 | Viswanathan |
| 7,993,353 | B2 | 8/2011 | Roeßner et al. |
| 8,017,515 | B2 | 9/2011 | Marimuthu et al. |
| 8,032,204 | B2 | 10/2011 | Solar et al. |
| 8,038,683 | B2 | 10/2011 | Couture et al. |
| 8,043,295 | B2 | 10/2011 | Reed et al. |
| 8,053,682 | B2 | 11/2011 | Park et al. |
| 8,073,530 | B2 | 12/2011 | Solar et al. |
| 8,079,518 | B2 | 12/2011 | Turner et al. |
| 8,096,266 | B2 | 1/2012 | Rowe |
| 8,123,675 | B2 | 2/2012 | Funda et al. |
| 8,165,366 | B2 | 4/2012 | Haimerl et al. |
| 8,211,094 | B2 | 7/2012 | Neubauer et al. |
| 8,265,731 | B2 | 9/2012 | Kukuk et al. |
| 8,274,263 | B2 | 9/2012 | McPherson |
| 8,320,612 | B2 | 11/2012 | Knobel et al. |
| 8,357,165 | B2 | 1/2013 | Grant et al. |
| 8,386,022 | B2 | 2/2013 | Jutras et al. |
| D682,195 | S | 5/2013 | Aglassinger |
| 8,442,621 | B2 | 5/2013 | Gorek et al. |
| D683,696 | S | 6/2013 | Woodard et al. |
| 8,521,255 | B2 | 8/2013 | DiSilvestro et al. |
| 8,534,848 | B2 | 9/2013 | Hauri et al. |
| 8,591,262 | B2 | 11/2013 | Schaffer et al. |
| D697,510 | S | 1/2014 | Sato et al. |
| 8,638,450 | B2 | 1/2014 | Faul et al. |
| 8,662,683 | B2 | 3/2014 | Rossner |
| 8,663,204 | B2 | 3/2014 | Lechner et al. |
| 8,710,996 | B1 | 4/2014 | Gronneberg |
| 8,715,296 | B2 | 5/2014 | Plassky et al. |
| 8,734,432 | B2 | 5/2014 | Tuma et al. |
| 8,800,939 | B2 | 8/2014 | Karsak et al. |
| 8,836,146 | B2 | 9/2014 | Chou et al. |
| 8,864,476 | B2 | 10/2014 | Moormann et al. |
| 8,878,490 | B2 | 11/2014 | LaSota et al. |
| 8,915,599 | B2 | 12/2014 | Rossner |
| 8,965,483 | B2 | 2/2015 | Couture et al. |
| 9,005,211 | B2 | 4/2015 | Brundobler et al. |
| 9,030,444 | B2 | 5/2015 | Birkenbach et al. |
| D731,411 | S | 6/2015 | Nakaishi |
| 9,044,269 | B2 | 6/2015 | Woerlein |
| 9,050,108 | B2 | 6/2015 | Grinberg et al. |
| 9,066,755 | B1 | 6/2015 | Jacobs et al. |
| D735,466 | S | 8/2015 | Akin et al. |
| 9,119,655 | B2 | 9/2015 | Bowling et al. |
| D740,234 | S | 10/2015 | Johannessen |
| D749,504 | S | 2/2016 | Jeong et al. |
| D749,727 | S | 2/2016 | Wapler et al. |
| D752,512 | S | 3/2016 | Dorn et al. |
| D756,299 | S | 5/2016 | Seidl et al. |
| D756,909 | S | 5/2016 | Gupta et al. |
| D756,910 | S | 5/2016 | Gupta et al. |
| D756,911 | S | 5/2016 | Gupta et al. |
| D758,305 | S | 6/2016 | Dorn et al. |
| D761,428 | S | 7/2016 | Birkenbach |
| 9,393,039 | B2 | 7/2016 | Lechner et al. |
| 9,456,827 | B2 | 10/2016 | Grinberg et al. |
| 9,468,427 | B2 | 10/2016 | Dicorleto et al. |
| 9,486,295 | B2 | 11/2016 | Vilsmeier et al. |
| D773,396 | S | 12/2016 | Hoffgaard |
| D776,052 | S | 1/2017 | Nommensen et al. |
| D776,610 | S | 1/2017 | Nommensen et al. |
| D777,100 | S | 1/2017 | Price |
| 9,572,630 | B2 | 2/2017 | Haimerl |
| 9,622,824 | B2 | 4/2017 | Goldbach |
| 9,622,832 | B2 | 4/2017 | Birkenbach et al. |
| D794,555 | S | 8/2017 | Meyerhoffer |
| 9,730,680 | B2 | 8/2017 | Tuma et al. |
| 9,737,370 | B2 | 8/2017 | Kheradpir et al. |
| 9,808,321 | B2 | 11/2017 | Huldin et al. |
| D806,247 | S | 12/2017 | Kheradpir et al. |
| 9,949,665 | B2 | 4/2018 | Müller et al. |
| D816,838 | S | 5/2018 | Kheradpir et al. |
| 9,974,615 | B2 | 5/2018 | Woerlein et al. |
| D820,984 | S | 6/2018 | Kheradpir et al. |
| D823,470 | S | 7/2018 | Neubauer et al. |
| 10,028,722 | B2 | 7/2018 | Moreau-Gaudry et al. |
| 10,034,713 | B2 | 7/2018 | Yang et al. |
| 10,039,605 | B2 | 8/2018 | Kostrzewski et al. |
| D828,561 | S | 9/2018 | Kheradpir et al. |
| 10,064,687 | B2 | 9/2018 | Haimerl et al. |
| D830,965 | S | 10/2018 | Varatharajah et al. |
| D831,003 | S | 10/2018 | Suzuki |
| 10,105,149 | B2 | 10/2018 | Haider et al. |
| 10,117,712 | B2 | 11/2018 | Plassky et al. |
| D838,848 | S | 1/2019 | Neubauer et al. |
| D838,849 | S | 1/2019 | Neubauer et al. |
| D841,572 | S | 2/2019 | Gilpatrick et al. |
| 10,278,787 | B2 | 5/2019 | Sela et al. |
| 10,318,024 | B2 | 6/2019 | Gogarty et al. |
| 10,330,133 | B2 | 6/2019 | Reutter et al. |
| 10,335,239 | B2 | 7/2019 | Plassky et al. |
| 10,335,247 | B2 | 7/2019 | Lechner et al. |
| D857,649 | S | 8/2019 | Ohlander et al. |
| D857,892 | S | 8/2019 | Crawford et al. |
| 10,368,851 | B2 | 8/2019 | Tuma et al. |
| D859,508 | S | 9/2019 | Zhang et al. |
| D860,447 | S | 9/2019 | Crawford et al. |
| D860,448 | S | 9/2019 | Crawford et al. |
| D860,943 | S | 9/2019 | Xie |
| 10,405,929 | B1 | 9/2019 | Seltmann et al. |
| D865,172 | S | 10/2019 | Crawford et al. |
| 10,429,957 | B2 | 10/2019 | Gogarty et al. |
| 10,456,207 | B2 | 10/2019 | Flatt |
| 10,499,996 | B2 | 12/2019 | de Almeida Barreto |
| 10,507,063 | B2 | 12/2019 | Zuhars et al. |
| 10,531,925 | B2 | 1/2020 | Malackowski et al. |
| 10,537,393 | B2 | 1/2020 | Huldin et al. |
| 10,537,395 | B2 | 1/2020 | Perez |
| 10,573,010 | B2 | 2/2020 | Held |
| 10,588,295 | B1 | 3/2020 | Riley |
| 10,667,390 | B2 | 5/2020 | Ketani et al. |
| 10,675,096 | B2 | 6/2020 | Utz et al. |
| 10,695,099 | B2 | 6/2020 | Scholl |
| 10,709,509 | B2 | 7/2020 | Scholl et al. |
| 10,722,223 | B2 | 7/2020 | Wehrli et al. |
| 10,725,566 | B2 | 7/2020 | Gogarty et al. |
| 10,731,687 | B2 | 8/2020 | Ponzer et al. |
| 10,765,480 | B2 | 9/2020 | Srimohanarajah et al. |
| 10,772,692 | B1 | 9/2020 | Li et al. |
| 10,792,108 | B2 | 10/2020 | Yang et al. |
| 10,806,519 | B2 | 10/2020 | Boivin et al. |
| 10,806,539 | B1 | 10/2020 | Richter et al. |
| 10,828,123 | B2 | 11/2020 | Mark et al. |
| 10,842,582 | B2 | 11/2020 | Lennertz et al. |
| 10,864,044 | B2 | 12/2020 | Nikou et al. |
| 10,864,045 | B2 | 12/2020 | Nikou et al. |
| 10,881,462 | B2 | 1/2021 | Heavener et al. |
| 10,898,271 | B2 | 1/2021 | Kemp et al. |
| D912,617 | S | 3/2021 | Qiao |
| 10,939,968 | B2 | 3/2021 | Kostrzewski et al. |
| 10,939,977 | B2 | 3/2021 | Messinger et al. |
| 10,993,771 | B2 | 5/2021 | Srimohanarajah et al. |
| 11,013,562 | B2 | 5/2021 | Marti et al. |
| 11,020,187 | B2 | 6/2021 | Kheradpir et al. |
| 11,033,353 | B2 | 6/2021 | Roger et al. |
| D925,451 | S | 7/2021 | Moreno et al. |
| 11,071,590 | B2 | 7/2021 | Moctezuma De la Barrera |
| 11,071,593 | B2 | 7/2021 | Abhari et al. |
| D931,798 | S | 9/2021 | He |
| D931,799 | S | 9/2021 | He |
| 11,114,731 | B2 | 9/2021 | Sazarin |
| 11,117,197 | B2 | 9/2021 | Lindenmann et al. |
| 2002/0087154 | A1 | 7/2002 | Shippert |
| 2002/0095081 | A1 | 7/2002 | Vilsmeier |
| 2002/0123310 | A1 | 9/2002 | Ikeda et al. |
| 2003/0220689 | A1 | 11/2003 | Ritland et al. |

(56) References Cited

U.S. PATENT DOCUMENTS

2004/0068263 A1 4/2004 Chouinard et al.
2004/0073279 A1 4/2004 Malackowski et al.
2004/0087852 A1 5/2004 Chen et al.
2004/0102792 A1 5/2004 Sarin et al.
2004/0113795 A1 6/2004 Groh et al.
2004/0167393 A1 8/2004 Solar et al.
2004/0181149 A1 9/2004 Langlotz et al.
2004/0254454 A1 12/2004 Kockro
2005/0065670 A1 3/2005 Tripmaker
2005/0075632 A1 4/2005 Russell et al.
2005/0113659 A1 5/2005 Pothier et al.
2005/0119561 A1 6/2005 Kienzle, III
2005/0124988 A1 6/2005 Terrill-Grisoni et al.
2005/0148855 A1 7/2005 Kienzle, III
2005/0149050 A1 7/2005 Stifter et al.
2005/0182320 A1 8/2005 Stifter et al.
2005/0228404 A1 10/2005 Vandevelde
2006/0004284 A1 1/2006 Grunschlager et al.
2006/0036162 A1 2/2006 Shahidi et al.
2006/0036397 A1 2/2006 Dick
2006/0122541 A1 6/2006 Tuma
2006/0142657 A1 6/2006 Quaid et al.
2006/0189867 A1 8/2006 Revie et al.
2006/0190011 A1 8/2006 Ries
2006/0195048 A1 8/2006 Leitner et al.
2006/0200025 A1 9/2006 Elliott et al.
2006/0241400 A1 10/2006 Bucholz
2006/0241405 A1 10/2006 Leitner et al.
2006/0246347 A1 11/2006 Diehl et al.
2006/0257379 A1 11/2006 Giordano et al.
2006/0271056 A1 11/2006 Terrill-Grisoni
2007/0003825 A1 1/2007 Touchton et al.
2007/0016009 A1 1/2007 Lakin et al.
2007/0018975 A1 1/2007 Chuanggui et al.
2007/0038059 A1 2/2007 Sheffer et al.
2007/0050983 A1 3/2007 Schnak et al.
2007/0050995 A1 3/2007 Schnak et al.
2007/0050997 A1 3/2007 Schnak et al.
2007/0078678 A1 4/2007 DiSilvestro et al.
2007/0106282 A1 5/2007 Lavallee
2007/0129629 A1 6/2007 Beauregard et al.
2007/0167744 A1 7/2007 Beauregard et al.
2007/0169782 A1 7/2007 Smothers et al.
2007/0194100 A1 8/2007 Plassky et al.
2007/0236514 A1 10/2007 Agusanto et al.
2007/0238981 A1 10/2007 Zhu et al.
2007/0238982 A1 10/2007 Caylor, III
2007/0239026 A1 10/2007 Immerz et al.
2007/0239169 A1 10/2007 Plaskos et al.
2007/0257638 A1 11/2007 Amend et al.
2007/0270660 A1 11/2007 Caylor et al.
2007/0270690 A1 11/2007 Woerlein
2007/0287910 A1 12/2007 Stallings et al.
2007/0299334 A1 12/2007 Vilsmeier
2008/0013809 A1 1/2008 Zhu et al.
2008/0051768 A1 2/2008 Stumpf
2008/0103509 A1 5/2008 Goldbach
2008/0125630 A1 5/2008 Caylor
2008/0154120 A1 6/2008 von Jako, M.D. et al.
2008/0172055 A1 7/2008 Mollard et al.
2008/0177203 A1 7/2008 von Jako
2008/0183068 A1 7/2008 Carls et al.
2008/0200794 A1 8/2008 Teichman et al.
2008/0208081 A1 8/2008 Murphy et al.
2008/0238368 A1 10/2008 Baron et al.
2008/0255442 A1 10/2008 Ashby et al.
2008/0281989 A1 11/2008 Hager et al.
2008/0287781 A1 11/2008 Revie et al.
2008/0287805 A1 11/2008 Li
2009/0041276 A1 2/2009 Sattler
2009/0099445 A1 4/2009 Burger
2009/0102420 A1 4/2009 Uehlein-Proctor et al.
2009/0109045 A1 4/2009 Delmonico et al.
2009/0157059 A1 6/2009 Allen et al.
2009/0163930 A1 6/2009 Aoude et al.
2009/0221908 A1 9/2009 Glossop
2009/0247861 A1 10/2009 Manus et al.
2009/0281428 A1 11/2009 Kammerzell et al.
2009/0306499 A1 12/2009 Van Vorhis et al.
2010/0063387 A1 3/2010 Timinger
2010/0179418 A1 7/2010 Mueller et al.
2010/0305435 A1 12/2010 Magill
2010/0305439 A1 12/2010 Shai et al.
2011/0040180 A1 2/2011 Leitner et al.
2011/0054449 A1 3/2011 Tien et al.
2011/0070478 A1 3/2011 Meschter
2011/0118750 A1 5/2011 Wu et al.
2011/0144476 A1 6/2011 Jolesz et al.
2011/0178395 A1 7/2011 Miesner et al.
2011/0196376 A1 8/2011 Ozgur
2011/0263971 A1 10/2011 Nikou et al.
2012/0035507 A1 2/2012 George et al.
2012/0168587 A1 7/2012 Karsak et al.
2013/0052059 A1 2/2013 Moormann et al.
2013/0052060 A1 2/2013 Meza et al.
2013/0079676 A1 3/2013 Hermle et al.
2014/0104284 A1 4/2014 Shenoy et al.
2014/0200439 A1 7/2014 Barsoum et al.
2014/0276007 A1 9/2014 Sela et al.
2014/0316234 A1 10/2014 Waite et al.
2015/0045656 A1 2/2015 Yoon et al.
2015/0156016 A1 6/2015 Moore et al.
2015/0196369 A1 7/2015 Glossop
2015/0201918 A1 7/2015 Kumar et al.
2015/0250459 A1 9/2015 Arm et al.
2015/0282735 A1 10/2015 Rossner
2015/0342462 A1 12/2015 Park et al.
2016/0038242 A1 2/2016 Lacono et al.
2016/0151119 A1 6/2016 Michel et al.
2016/0184029 A1 6/2016 Peng et al.
2016/0220145 A1 8/2016 Rossner
2016/0228033 A1 8/2016 Rossner
2016/0256225 A1 9/2016 Crawford et al.
2016/0302871 A1 10/2016 Gregerson et al.
2016/0317232 A1 11/2016 Vaillant et al.
2016/0354009 A1 12/2016 Schroeder
2017/0007328 A1 1/2017 Cattin et al.
2017/0007353 A1 1/2017 Fleig et al.
2017/0042557 A1 2/2017 Plaskos et al.
2017/0086941 A1 3/2017 Marti et al.
2017/0165005 A1 6/2017 Kheradpir et al.
2017/0165006 A1 6/2017 Woods et al.
2017/0209225 A1 7/2017 Wu
2017/0238996 A1 8/2017 Frame et al.
2017/0252114 A1 9/2017 Crawford et al.
2017/0258535 A1 9/2017 Crawford et al.
2017/0265774 A1 9/2017 Johnson et al.
2017/0265943 A1 9/2017 Sela et al.
2017/0311843 A1 11/2017 Bailey et al.
2017/0312033 A1 11/2017 Huang et al.
2017/0319289 A1 11/2017 Neff
2017/0347922 A1 12/2017 Bhandari
2017/0360521 A1 12/2017 Johnson
2018/0107291 A1 4/2018 Gogarty et al.
2018/0132839 A1 5/2018 Friedrich et al.
2018/0147021 A2 5/2018 Fleig et al.
2018/0185100 A1 7/2018 Weinstein et al.
2018/0205051 A1 7/2018 Sakai et al.
2018/0221098 A1 8/2018 Forsyth et al.
2018/0228553 A1 8/2018 Bai et al.
2018/0256259 A1 9/2018 Crawford
2018/0279993 A1 10/2018 Crawford et al.
2018/0296283 A1 10/2018 Crawford et al.
2018/0311051 A1 11/2018 Donaldson et al.
2018/0325610 A1 11/2018 Cameron et al.
2018/0338799 A1 11/2018 Hladio et al.
2019/0000561 A1 1/2019 Decker et al.
2019/0000569 A1 1/2019 Crawford et al.
2019/0000571 A1 1/2019 Johnson et al.
2019/0015163 A1 1/2019 Abhari et al.
2019/0021798 A1 1/2019 Netravali et al.
2019/0029765 A1 1/2019 Crawford et al.
2019/0038366 A1 2/2019 Johnson et al.
2019/0105116 A1 4/2019 Johnson et al.

(56) References Cited

U.S. PATENT DOCUMENTS

| | | | |
|---|---|---|---|
| 2019/0117313 | A1 | 4/2019 | Crawford |
| 2019/0142401 | A1 | 5/2019 | Tuma et al. |
| 2019/0175283 | A1 | 6/2019 | Bonny et al. |
| 2019/0209080 | A1 | 7/2019 | Gullotti et al. |
| 2019/0223962 | A1 | 7/2019 | Roldan et al. |
| 2019/0231447 | A1 | 8/2019 | Ebbitt et al. |
| 2019/0274765 | A1 | 9/2019 | Crawford et al. |
| 2019/0321108 | A1 | 10/2019 | Ghanam et al. |
| 2019/0336029 | A1 | 11/2019 | Wood et al. |
| 2019/0357986 | A1 | 11/2019 | Morgan et al. |
| 2019/0380794 | A1 | 12/2019 | Al Jewad et al. |
| 2019/0388155 | A1 | 12/2019 | Cattin et al. |
| 2019/0388161 | A1 | 12/2019 | Cicchini et al. |
| 2020/0008878 | A1 | 1/2020 | Srimohanarajah et al. |
| 2020/0069376 | A1 | 3/2020 | Garcia et al. |
| 2020/0078097 | A1 | 3/2020 | Gregerson et al. |
| 2020/0100848 | A1 | 4/2020 | Zuhars et al. |
| 2020/0129241 | A1 | 4/2020 | Forstein et al. |
| 2020/0129243 | A1 | 4/2020 | Kemp et al. |
| 2020/0146754 | A1 | 5/2020 | Row et al. |
| 2020/0155241 | A1 | 5/2020 | Cascarano et al. |
| 2020/0188031 | A1 | 6/2020 | Palushi et al. |
| 2020/0197113 | A1 | 6/2020 | Felenc |
| 2020/0197191 | A1 | 6/2020 | Akhlaghpour et al. |
| 2020/0237445 | A1 | 7/2020 | Snyder et al. |
| 2020/0261120 | A1 | 8/2020 | Scholl |
| 2020/0281656 | A1 | 9/2020 | Torabi et al. |
| 2020/0289210 | A1 | 9/2020 | Scholl et al. |
| 2020/0305978 | A1 | 10/2020 | Tan et al. |
| 2020/0323521 | A1 | 10/2020 | Wehrli et al. |
| 2020/0345428 | A1 | 11/2020 | Marti et al. |
| 2020/0367973 | A1 | 11/2020 | Han et al. |
| 2020/0368898 | A1 | 11/2020 | Perez |
| 2020/0390506 | A1 | 12/2020 | Bonny |
| 2020/0405395 | A1 | 12/2020 | Gullotti et al. |
| 2021/0030443 | A1 | 2/2021 | Scholl et al. |
| 2021/0030479 | A1 | 2/2021 | Marti et al. |
| 2021/0052327 | A1 | 2/2021 | Kuznik et al. |
| 2021/0059757 | A1 | 3/2021 | Nikou et al. |
| 2021/0059760 | A1 | 3/2021 | Tseng et al. |
| 2021/0085403 | A1 | 3/2021 | Roger et al. |
| 2021/0093393 | A1 | 4/2021 | Quist et al. |
| 2021/0093394 | A1 | 4/2021 | Yang et al. |
| 2021/0153851 | A1 | 5/2021 | Ma et al. |
| 2021/0165197 | A1 | 6/2021 | Litsch et al. |
| 2021/0196403 | A1 | 7/2021 | Andersson |
| 2021/0205037 | A1 | 7/2021 | Tabandeh et al. |
| 2021/0233330 | A1 | 7/2021 | Sutherland et al. |
| 2021/0236208 | A1 | 8/2021 | Drexl et al. |
| 2021/0244478 | A1 | 8/2021 | Richter et al. |
| 2021/0244481 | A1 | 8/2021 | Jaramaz et al. |
| 2021/0251700 | A1 | 8/2021 | Kheradpir et al. |
| 2021/0259781 | A1 | 8/2021 | Forstein et al. |
| 2021/0307765 | A1 | 10/2021 | Dumpe et al. |
| 2021/0307838 | A1 | 10/2021 | Xia et al. |
| 2022/0211441 | A1 | 7/2022 | Johnson et al. |

FOREIGN PATENT DOCUMENTS

| | | | |
|---|---|---|---|
| CN | 103133357 | A | 6/2013 |
| CN | 112716605 | B | 6/2021 |
| DE | 102010064389 | A1 | 7/2012 |
| DE | 102016006813 | A1 | 12/2017 |
| EP | 1806959 | A1 | 7/2007 |
| EP | 1872735 | A1 | 1/2008 |
| EP | 1950820 | A1 | 7/2008 |
| EP | 2594801 | B1 | 10/2017 |
| TW | I469422 | B | 1/2015 |
| WO | 96004626 | A1 | 2/1996 |
| WO | 9836371 | A1 | 8/1998 |
| WO | 9933406 | A1 | 7/1999 |
| WO | 0028911 | A1 | 5/2000 |
| WO | 0053115 | A1 | 9/2000 |
| WO | 200064367 | A1 | 11/2000 |
| WO | 2020010448 | A1 | 1/2001 |
| WO | 2001026574 | A1 | 4/2001 |
| WO | 0224094 | A2 | 3/2002 |
| WO | 02062248 | A1 | 8/2002 |
| WO | 03026505 | A1 | 4/2003 |
| WO | 2004107959 | A2 | 12/2004 |
| WO | 2005001679 | A1 | 1/2005 |
| WO | 2005037120 | A1 | 4/2005 |
| WO | 2005063139 | A1 | 7/2005 |
| WO | 2005122940 | A1 | 12/2005 |
| WO | 2006062295 | A1 | 6/2006 |
| WO | 2006074954 | A1 | 7/2006 |
| WO | 2006081558 | A2 | 8/2006 |
| WO | 2007010330 | A1 | 1/2007 |
| WO | 2008076079 | A8 | 9/2008 |
| WO | 2008104548 | A1 | 9/2008 |
| WO | 2008130355 | A1 | 10/2008 |
| WO | 2010003247 | A1 | 1/2010 |
| WO | 2012013304 | A1 | 2/2012 |
| WO | 2012152879 | A1 | 11/2012 |
| WO | 2015060711 | A2 | 4/2015 |
| WO | 2015144246 | A1 | 10/2015 |
| WO | 2015150877 | A1 | 10/2015 |
| WO | 2017072653 | A1 | 5/2017 |
| WO | 2018113887 | A2 | 6/2018 |
| WO | 2019048284 | A1 | 3/2019 |
| WO | 2019090705 | A1 | 5/2019 |
| WO | 2019127449 | A1 | 7/2019 |
| WO | 2019135805 | A1 | 7/2019 |
| WO | 2019210077 | A2 | 10/2019 |
| WO | 2020207583 | A1 | 1/2020 |
| WO | 2020208171 | A1 | 1/2020 |
| WO | 2020056527 | A1 | 3/2020 |
| WO | 2020113030 | A1 | 6/2020 |
| WO | 2020160143 | A1 | 8/2020 |
| WO | 2020163457 | A1 | 8/2020 |
| WO | 2020205714 | A1 | 10/2020 |
| WO | 2020210782 | A1 | 10/2020 |
| WO | 2020220441 | A1 | 11/2020 |
| WO | 2020223312 | A1 | 11/2020 |
| WO | 2021059253 | A2 | 4/2021 |
| WO | 2021084484 | A2 | 5/2021 |
| WO | 2021113227 | A1 | 6/2021 |
| WO | 2021156479 | A1 | 8/2021 |
| WO | 2022011090 | A1 | 1/2022 |
| WO | W02023002045 | A1 | 1/2023 |

OTHER PUBLICATIONS

English language abstract and machine-assisted English translation for CN 103133357 A extracted from espacenet.com database on Apr. 24, 2023, 14 pages.

English language abstract and machine-assisted English translation for CN 112716605 B extracted from espacenet.com database on Apr. 24, 2023, 10 pages.

English language abstract for DE 10 2010 064 389 A extracted from espacenet.com database on Apr. 24, 2023, 2 pages.

English language abstract and machine-assisted English translation for DE 10 2016 006 813 A1 extracted from espacenet.com database on Apr. 24, 2023, 14 pages.

English language abstract for EP 1 872 735 A1 extracted from espacenet.com database on Apr. 24, 2023, 2 pages.

English language abstract and machine-assisted English translation for EP 1 950 820 A1 extracted from espacenet.com database on Apr. 24, 2023, 8 pages.

English language abstract for TWI 469422 B extracted from espacenet.com database on Apr. 24, 2023, 2 pages.

English language abstract and machine-assisted English translation for WO 00/28911 A1 extracted from espacenet.com database on Apr. 25, 2023, 13 pages.

English language abstract and machine-assisted English translation for WO 00/53115 A1 extracted from espacenet.com database on Apr. 25, 2023, 4 pages.

(56) References Cited

OTHER PUBLICATIONS

English language abstract and machine-assisted English translation for WO 01/26574 A1 extracted from espacenet.com database on Apr. 25, 2023, 7 pages.
English language abstract for WO 03/026505 A1 extracted from espacenet.com database on Apr. 25, 2023, 2 pages.
English language abstract and machine-assisted English translation for WO 2005/001679 A1 extracted from espacenet.com database on Apr. 25, 2023, 8 pages.
English language abstract and machine-assisted English translation for WO 2005/037120 A1 extracted from espacenet.com database on Apr. 25, 2023, 8 pages.
English language abstract and machine-assisted English translation for WO 2005/122940 A1 extracted from espacenet.com database on Apr. 25, 2023, 10 pages.
English language abstract and machine-assisted English translation for WO 2006/074954 A1 extracted from espacenet.com database on Apr. 25, 2023, 10 pages.
English language abstract and machine-assisted English translation for WO 2007/010330 A1 extracted from espacenet.com database on Apr. 25, 2023, 14 pages.
English language abstract and machine-assisted English translation for WO 2008/104548 A1 extracted from espacenet.com database on Apr. 25, 2023, 10 pages ..
English language abstract and machine-assisted English translation for WO 2012/013304 A1 extracted from espacenet.com database on Apr. 25, 2023, 9 pages.
English language abstract and machine-assisted English translation for WO 2012/152879 A1 extracted from espacenet.com database on Apr. 25, 2023, 15 pages.
English language abstract and machine-assisted English translation for WO 2019/090705 A1 extracted from espacenet.com database on Apr. 25, 2023, 9 pages.
English language abstract for WO 2019/127449 A1 extracted from espacenet.com database on Apr. 25, 2023, 2 pages.
English language abstract for WO 2020/22041 A1 extracted from espacenet.com database on Apr. 25, 2023, 1 page.
International Search Report for Application No. PCT/US2023/019415 dated Aug. 24, 2023, 2 pages.

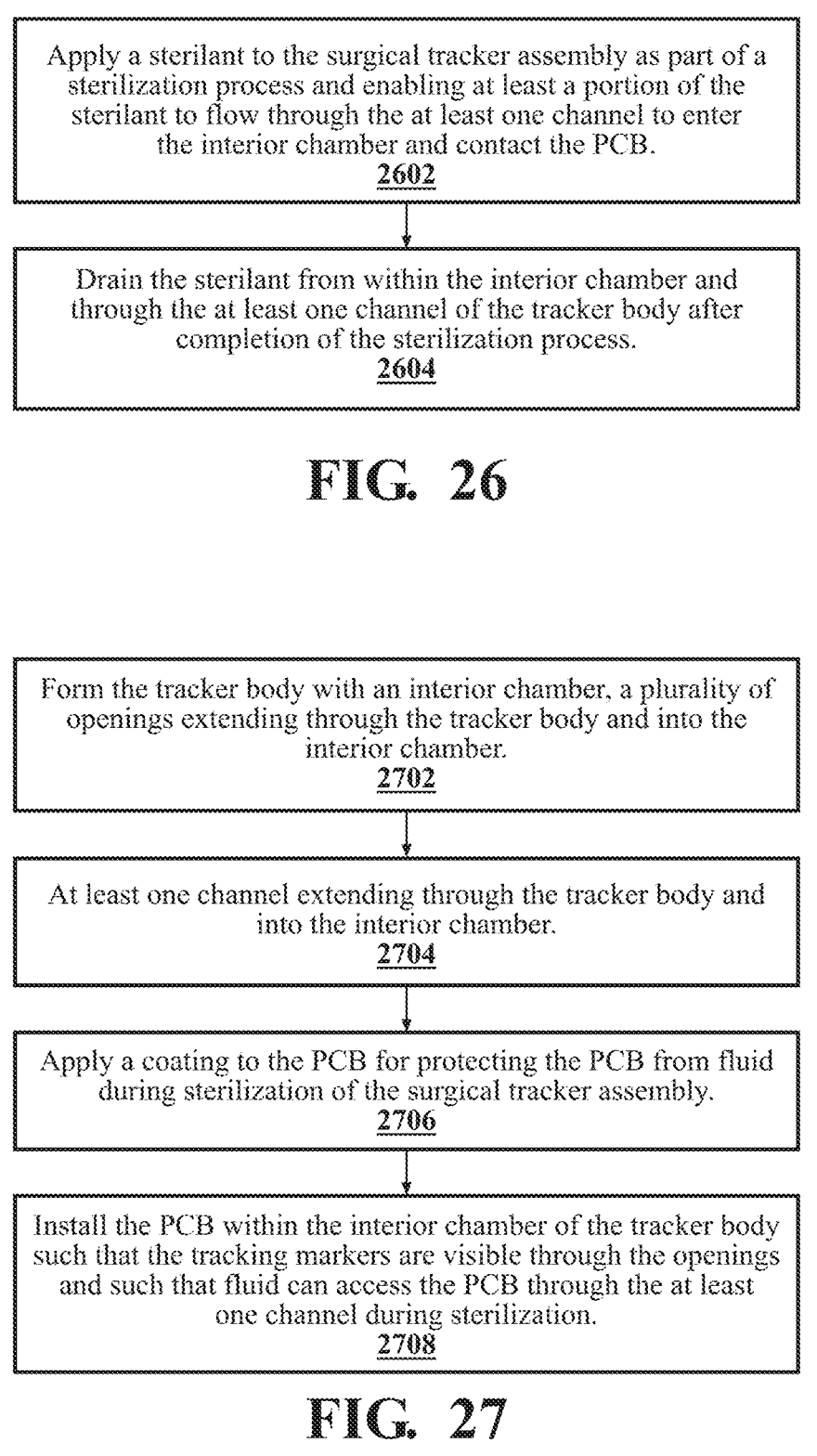

Apply a sterilant to the surgical tracker assembly as part of a sterilization process and enabling at least a portion of the sterilant to flow through the at least one channel to enter the interior chamber and contact the PCB.
2602

Drain the sterilant from within the interior chamber and through the at least one channel of the tracker body after completion of the sterilization process.
2604

FIG. 26

Form the tracker body with an interior chamber, a plurality of openings extending through the tracker body and into the interior chamber.
2702

At least one channel extending through the tracker body and into the interior chamber.
2704

Apply a coating to the PCB for protecting the PCB from fluid during sterilization of the surgical tracker assembly.
2706

Install the PCB within the interior chamber of the tracker body such that the tracking markers are visible through the openings and such that fluid can access the PCB through the at least one channel during sterilization.
2708

FIG. 27

STERILIZABLE SURGICAL DEVICE WITH BATTERY SWITCH

CROSS-REFERENCE TO RELATED APPLICATIONS

The present application claims priority to and all the benefits of U.S. Provisional Patent Application No. 63/333,676, filed on Apr. 22, 2022, which is expressly incorporated herein by reference.

BACKGROUND

Navigation systems are frequently utilized to assist medical professionals in carrying out various types of surgical procedures, including neurosurgical and orthopedic procedures. To this end, a surgeon may utilize a navigation system to track, monitor, or otherwise locate one or more tools, surgical instruments, and/or portions of a patient's anatomy within a common reference frame. Typically, tools and/or surgical instruments are tracked together with the anatomy, and their relative movement is depicted on a display. Often, trackers are attached or otherwise integrated into the objects being tracked. A localizer cooperates with tracking elements (e.g., fiducials, markers, and the like) coupled to the trackers to monitor the tracker to determine a position and/or orientation of the object being tracked.

Many types of navigation systems may utilize an active tracker that requires a power source for operation of components of the tracker, e.g., activation of markers on the tracker. Many active trackers have utilized a battery as the power source. However, if the battery is not replaceable or removable from the tracker, sterilization of the tracker can destroy the battery, reduce viable lifetime of the battery and/or force the tracker to be a "single use" tracker that must be discarded. Furthermore, even if the battery is removable from the conventional tracker, the internal components of the tracker are typically not well adapted to withstand the sterilization process. In such instances, the sensitive internal components of the tracker must be removed before sterilization to ensure the internal components are not damaged. Removal of these components is a time-consuming process that adds complexity and costs. Accordingly, there remains a need in the art to overcome at least the deficiencies described above.

SUMMARY

This Summary introduces a selection of concepts in a simplified form that are further described below in the Detailed Description below. This Summary is not intended to limit the scope of the claimed subject matter nor identify key features or essential features of the claimed subject matter.

According to a first aspect, a surgical tracker is provided for identifying and/or tracking a surgical instrument. The surgical tracker includes a tracker body that may include a first surface, a second surface spaced from and opposite the first surface, and a side surface connected between the first and second surfaces, the tracker body defining a chamber formed within the first surface, second surface, and side surface. The tracker also includes a plurality of openings formed in the first surface. The tracker also includes at least one channel formed in the tracker body, the at least one channel extending between the chamber and one of the surfaces of the tracker body. The tracker also includes a printed circuit board (PCB) being configured to support a plurality of markers that are actively energizable through the PCB, and where the PCB is located within the chamber of the tracker body and where each one of the markers is visible through one of the plurality of openings of the tracker body. The tracker also includes where the tracker body is configured to be sterilizable with the PCB being located within the chamber of the tracker body, and where the at least one channel is configured to enable sterilization fluid to enter into and drain from the chamber of the tracker body during sterilization.

According to a second aspect, a surgical tracker is provided. The surgical tracker also includes a tracker body defining an interior chamber. The tracker also includes a plurality of openings extending through the tracker body and into the interior chamber. The tracker also includes at least one channel extending through the tracker body and into the interior chamber, the at least one channel configured to enable fluid to enter into and drain from the interior chamber. The tracker also includes a printed circuit board (PCB) located within the interior chamber and being configured to support a plurality of tracking markers, where each tracking marker is visible through and substantially occupies one of the openings.

According to a third aspect, a surgical tracker is disclosed. The surgical tracker assembly also includes a tracker body defining an interior chamber and a battery opening, where a first contact and a second contact are disposed in the battery opening. The assembly also includes a channel formed within the tracker body, the channel extending from the interior chamber and through an exterior surface of the tracker body and configured to enable sterilization fluid to enter into and drain from the interior chamber of the tracker body during sterilization. The assembly also includes a printed circuit board (PCB) at least partially disposed in the interior chamber, the PCB supporting at least one marker and the PCB being connected to the first contact and the second contact. The assembly also includes a battery assembly removably couplable to the tracker body and configured to be securely installed in the battery opening, the battery assembly may include a first battery contact configured to engage the first contact and a second battery contact configured to engage the second contact to form an electrical connection with the PCB and to enable the PCB to actively energize the at least one marker.

According to a fourth aspect, a surgical tracker is disclosed. The surgical tracker assembly also includes a tracker body defining an interior chamber. The assembly also includes a channel extending through the tracker body and into the interior chamber, the channel configured to enable sterilization fluid to enter into and drain from the interior chamber. The assembly also includes a printed circuit board (PCB) at least partially disposed in the interior chamber, the PCB supporting at least one tracking marker. The assembly also includes where the PCB is coated with a parylene coating to protect the PCB from sterilization fluid that enters the interior chamber of the tracker body through the channel during sterilization.

According to a fifth aspect, a surgical tracker assembly is provided. The surgical tracker assembly comprises a tracker body defining an interior chamber and a battery opening, wherein a first contact and a second contact are disposed in the battery opening. A printed circuit board (PCB) is at least partially disposed in the interior chamber, the PCB supporting at least one marker and the PCB being connected to the first contact and the second contact. A battery assembly comprises a first battery contact and a second battery contact. The battery assembly is configured to be installed in the battery opening in a first position wherein the first battery contact of the battery assembly engages the first contact and the second battery contact of the battery assembly is disengaged from the second contact thereby creating an open circuit between the battery assembly and the PCB. The battery assembly, when installed in the battery opening, is configured to be rotated from the first position to a second position wherein the first battery contact of the battery assembly engages the first contact and the second battery contact of the battery assembly engages the second contact to form a closed circuit between the battery assembly and the PCB for energizing the PCB.

According to a sixth aspect, a method of sterilizing a surgical tracker assembly including a tracker body defining an interior chamber is disclosed. The method also includes applying a sterilant to the surgical tracker assembly as part of a sterilization process and enabling at least a portion of the sterilant to flow through the at least one channel to enter the interior chamber and contact the PCB. The method also includes draining the sterilant from within the interior chamber and through the at least one channel of the tracker body after completion of the sterilization process.

According to a seventh aspect, a method of manufacturing a surgical tracker assembly including a tracker body and a printed circuit board (PCB) supporting a plurality of tracking markers is disclosed. The method also includes forming the tracker body with an interior chamber, a plurality of openings extending through the tracker body and into the interior chamber; and at least one channel extending through the tracker body and into the interior chamber. The method also includes applying a coating to the PCB for protecting the PCB from fluid during sterilization of the surgical tracker assembly. The method also includes installing the PCB within the interior chamber of the tracker body such that the tracking markers are visible through the openings and such that fluid can access the PCB through the at least one channel during sterilization.

According to an eighth aspect, a method of activating a surgical tracker is disclosed. The method may include connecting a battery assembly to a surgical tracker. The method also includes installing the battery assembly in the battery opening in a first position where the first battery contact of the battery assembly is engaging the first contact and the second battery contact of the battery assembly is disengaged from the second contact thereby creating an open circuit between the battery assembly and the PCB. The method also includes while installed in the battery opening, rotating the battery assembly from the first position to a second position where the first battery contact of the battery assembly is engaging the first contact and the second battery contact of the battery assembly is engaging the second contact to form a closed circuit between the battery assembly and the PCB.

According to a ninth aspect, a battery assembly is provided that is configured to couple to a battery opening of a surgical tracker. The battery assembly comprises a body that is annular and defines an exterior surface and an interior chamber configured to receive a battery. Two electrical contacts are coupled to the battery within the interior chamber. A first and a second electrical contact extend through the exterior surface of the body such that they are exposed. The first electrical contact is located at a distal end of the body. The second electrical contact is located on the side of the body. The exterior surface comprises one or more channels to guide an electrical contact of the surgical tracker into engagement with the second electrical contact in response to rotation of the battery assembly within the battery opening of the surgical tracker.

According to a tenth aspect, an adapter is provided for mounting a tracker to a surgical instrument for use with a surgical navigation system to track the pose of the surgical instrument.

Any of the above aspects can be utilized individually, or in combination.

Any of the above aspects can be utilized with any of the following implementations:

In some implementations, the tracker body defines at least three tracker body arms and each of the tracker body arms may define at least one opening formed in the tracker body. In some implementations, the at least one channel is formed in each tracker body arm of the tracker body. The tracker can be a tool tracker, an anatomy tracker, a manipulator tracker or base tracker, an end effector tracker, a pointer tracker, a hand-held robotic cutting tool tracker, an imaging device tracker, a limb holder tracker, a surgical table tracker, a head-mounted device tracker, or the like.

In some implementations, the PCB and the tracker body may be configured to have similar shapes. This may include being formed in the shape of a triangle, square, rectangle, or other similar polygonal shape. It is also contemplated that the PCB and the tracker body may comprise less traditional shapes such as being x-shaped, T-shaped, or the like. In some implementations, each of the PCB arms is configured to support one of the markers and/or each of the PCB arms is arranged within the tracker body such that each marker is visible through one of the plurality of openings formed in the tracker body. In some implementations, the PCB is sterilizable. This may be accomplished by applying a protective coating to the PCB. One type of coating that may be applied to the PCB is a parylene coating. In some implementations, the PCB comprises an infrared (IR) communication receiver. In some implementations, the PCB may further comprise a line-of-sight (LOS) indicator that is configured to be controlled to indicate presence and/or absence of a line-of-sight communication from any one or more of the markers to a camera of a surgical navigation system.

In some implementations, the tracker body further defines a battery opening that is configured to receive a battery assembly, the battery removably couplable to the tracker body via the battery opening. A first electrical contact and/or a second electrical contact may be disposed in the battery opening and connected to the PCB, the first contact and the second contact configured to engage opposing battery contacts of the battery assembly to form an electrical connection between the battery assembly and the PCB when the battery assembly is disposed in the battery opening. In some implementations, the battery assembly can be a battery module switch. In some implementations, the battery assembly can provide a seal to the battery opening when installed. In some implementations, the battery assembly is a disposable, single use, component.

According to an eleventh aspect, a sterilizable printed circuit board assembly (PCBA) is provided. The sterilizable printed circuit board assembly includes a printed circuit board (PCB) substrate may include layers including a first outer layer, a second outer layer, and one or more inner layers disposed between the first and second outer layers. The assembly also includes a via-in-pad formed in the PCB substrate and may include a via hole extending through at least one of the layers, the via hole may include a first end terminating at one of the inner layers and a second end terminating at, or beyond, one of the outer layers, and the via-in-pad may include a plating that seals the via hole at the second end. The assembly also includes a parylene coating that is sterilization resistant and disposed in direct contact with one or both of the first and second outer layers.

According to a twelfth aspect, a sterilizable surgical or medical device is provided. The sterilizable surgical or medical device includes a housing defining: an interior chamber; and an opening defined in an outer surface of the housing and in fluid communication with the interior chamber, the opening configured to enable fluid to enter into and drain from the interior chamber. The device also includes a sterilizable printed circuit board assembly (PCBA) disposed within the interior chamber of the housing and may include: a printed circuit board (PCB) substrate may include layers including a first outer layer, a second outer layer, and one or more inner layers disposed between the first and second outer layers; a via-in-pad formed in the PCB substrate and may include a via hole extending through at least two of the layers, the via hole may include a first end terminating at one of the inner layers and a second end terminating at, or beyond, one of the outer layers, and the via-in-pad may include a plating that seals the via hole at the second end; an electronic or electrical component electrically connected to the via-in-pad and being configured to facilitate operation of the surgical or medical device; and a parylene coating that is sterilization resistant and disposed in direct contact with one or both of the outer layers and in direct contact with at least a portion of the electronic or electrical component.

According to a thirteenth aspect, a sterilizable tracking device is provided. The sterilizable tracking device includes a tracker body defining: an interior chamber; an opening defined in an outer surface of the tracker body and in communication with a channel extending through the tracker body and into the interior chamber, the opening and the channel configured to enable sterilization fluid to enter into and drain from the interior chamber. The device also includes a sterilizable printed circuit board assembly (PCBA) disposed within the interior chamber of the tracker body and may include: a printed circuit board (PCB) substrate may include layers including a first outer layer, a second outer layer, and one or more inner layers disposed between the first and second outer layers; a via-in-pad formed in the PCB substrate and may include a via hole extending through at least two of the layers, the via hole may include a first end terminating at one of the inner layers and a second end terminating at, or beyond, one of the outer layers, and the via-in-pad may include a plating that seals the via hole at the second end; a tracking marker electrically connected to the via-in-pad; and a parylene coating that is sterilization resistant and disposed in direct contact with one or both of the outer layers and in direct contact with at least a portion of the tracking marker.

According to a fourteenth aspect, a sterilizable printed circuit board assembly (PCBA) is provided. The sterilizable printed circuit board assembly includes a printed circuit board (PCB) substrate may include layers including a first outer layer, a second outer layer, and one or more inner layers disposed between the first and second outer layers. The assembly also includes a via-in-pad formed in the PCB substrate and may include a via hole extending through at least one of the outer layers, the via-in-pad may include a plating that seals the via hole at the second end. The assembly also includes a conformal coating that is sterilization resistant and disposed in direct contact with one or both of the first and second outer layers.

In some implementations, the PCBA or sterilizable surgical/medical device may optionally be configured where the plating seals the via hole such that no solder mask is otherwise required to seal the via hole.

In some implementations, the PCBA or sterilizable surgical/medical device may optionally be configured where the parylene coating is solely the only coating disposed on the PCBA. It is also contemplated that the parylene coating is disposed in direct contact with the first and second outer layers, and the plating. The parylene coating may be a conformal coating.

In some implementations, the PCBA or sterilizable surgical/medical device may optionally be configured where the via-in-pad further comprises a surface cap disposed over the plating, and wherein the parylene coating is disposed in direct contact with the surface cap. It is also contemplated that the via hole has an interior surface that is plated with a conductive material and a non-conductive material that fills the via hole.

In some implementations, the PCBA or sterilizable surgical/medical device may optionally be configured where the plating is integrated and flush with the one of the outer layers, or wherein the plating is disposed on top of one of the outer layers. The PCBA or sterilizable surgical/medical device may also further comprise an electronic or electrical component is electrically connected to the via-in-pad, and wherein the parylene coating covers at least a portion of the electronic or electrical component.

In some implementations, the PCBA or sterilizable surgical/medical device may optionally be configured where the PCB comprises one or more conductive traces disposed on, or in, the inner layers, and wherein the PCB is designed such that no conductive traces are disposed on an exterior surface of the outer layers.

In some implementations, the PCBA or sterilizable surgical/medical device may optionally comprise a solder mask is applied directly to a portion of the first and second outer layers surrounding the via-in-pad, the parylene coating being applied directly to a remaining portion of the first and second outer layers and over the solder mask.

According to a fifteenth aspect, a method of manufacturing a sterilizable printed circuit board assembly (PCBA) is provided. The method includes assembling a printed circuit board (PCB) substrate including a first outer layer, a second outer layer, and one or more inner layers disposed between the first and second outer layers. The method also includes forming a via-in-pad in the PCB substrate with a via hole extending through at least one of the outer layers. The method also includes sealing the via hole with a plating at the second end. The method also includes applying a parylene coating that is sterilization resistant to the PCBA such that the parylene coating is disposed in direct contact with one or both of the outer layers.

Any of the above implementations can be combined, in part, or in whole.

Other features and advantages of the configurations of the present disclosure will be readily appreciated, as the same becomes better understood, after reading the subsequent description taken in conjunction with the accompanying drawings.

BRIEF DESCRIPTION OF THE DRAWINGS

FIG. 26 is a flow chart illustrating a method of sterilizing a surgical tracker assembly including a tracker body defining an interior chamber, a plurality of openings extending through the tracker body and into the interior chamber, at least one channel extending through the tracker body and into the interior chamber, and a printed circuit board (PCB) located within the interior chamber and being configured to support a plurality of tracking markers.

FIG. 27 is a flow chart illustrating a method of manufacturing a surgical tracker assembly including a tracker body and a printed circuit board (PCB) supporting a plurality of tracking markers.

Figure 1:
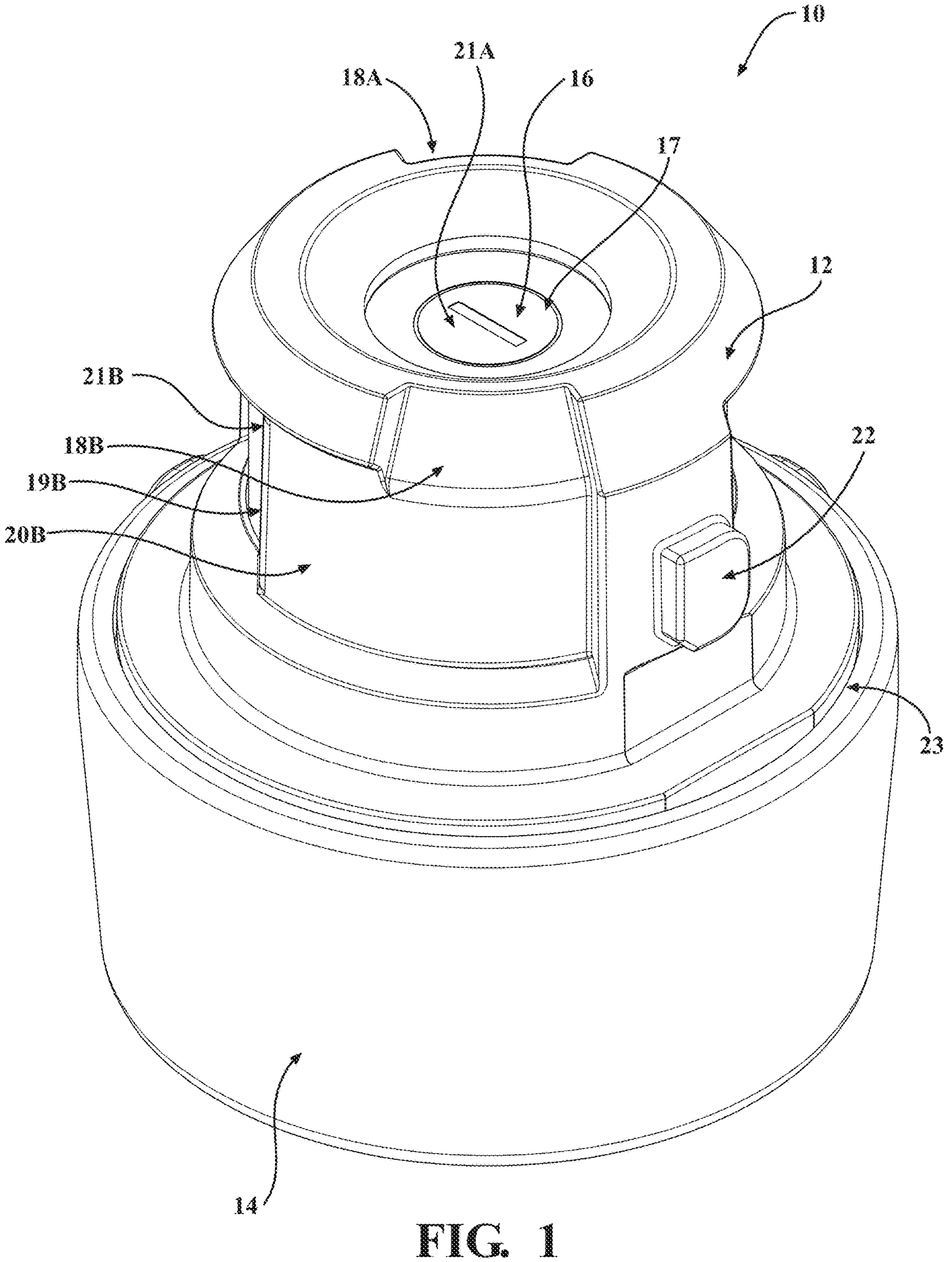
FIG. 1 is a perspective view of a battery assembly for use with a tracker, according to one implementation.

It will be appreciated that one or more of the configurations depicted throughout the drawings may have certain components, structural features, and/or assemblies removed, depicted schematically, and/or shown in phantom for illustrative purposes.

DETAILED DESCRIPTION

I. Surgical Tracker Assembly

The present disclosure describes a tracker that can be sterilizable such that a single tracker is capable of being used multiple times. To accomplish this, the tracker and/or tracker assembly may comprise features to assist with the sterilization process. The tracker assembly may be adapted to allow for the sterilant utilized in the sterilization process to reach all surfaces of the tracker assembly. Furthermore, the sensitive electrical or electronic components of the tracker assembly may be treated with an additive or coating to prevent damage if exposed to the sterilant. It is further contemplated that the tracker assembly may comprise a removable and/or replaceable battery assembly. In addition to powering the electronic components of the tracker assembly, the battery assembly may be configured to activate and/or deactivate the tracker assembly. Other advantages will be understood as the various features of the tracker assembly will be described in greater detail below.

Referring now to the Figures, wherein like numerals indicate like or corresponding parts throughout the several views, implementations of a surgical tracker assembly 1 are provided. The surgical tracker assembly 1 comprises a surgical tracker 30 (as illustrated in FIGS. 7 to 13) and a battery assembly 10 (as shown in FIGS. 1 to 6) for use with the surgical tracker 30. The surgical tracker assembly 1 is configured to couple to, or is fixed to, a surgical object to be tracked. The surgical tracker assembly 1 can be used for tracking any surgical object, such as a surgical instrument, a navigated pointer or digitizer, the patient anatomy, a robotic manipulator arm, a robotic manipulator end-effector, a robotic manipulator base or cart, a hand-held tool, an imaging device or gantry, a limb holder, a surgical table, a head-mounted device, or the like. The tracker assembly 1 can be utilized for tracking any object of the surgical system described in U.S. Pat. No. 9,119,655, entitled, "Surgical Manipulator Capable of Controlling a Surgical Instrument in Multiple Modes", the entire contents of which is hereby incorporated by reference. Each of the components of the surgical tracker assembly 1 introduced above will be described in greater detail below.

A. Removeable Battery Assembly Implementations

Referring to FIGS. 1 to 6, the battery assembly 10 may include a housing 12, 14 comprised of a first portion 12 and a second portion 14. The first portion 12 and second portion 14 collectively define a void 15A, 15B (best illustrated in FIG. 6) for receiving and housing a battery 16 or similar power source. The first portion 12 and second portion 14 may be formed from a plastic or similar polymeric material. The material may be selected from a group of polymers capable of providing insulating properties to prevent the battery from unessentially creating an electric connection other than through the designated apertures 17, 19 (described below). Alternatively, it is also contemplated that all or a limited portion of the first portion 12 and second portion 14 may be formed from a steel, carbon, titanium, or similar material capable of serving as a conductive surface between the battery 16 and/or an external electrical contact 45. In another implementation, the entire housing of the battery assembly 10 may be integrally formed of a single-unitary material.

Figure 6:
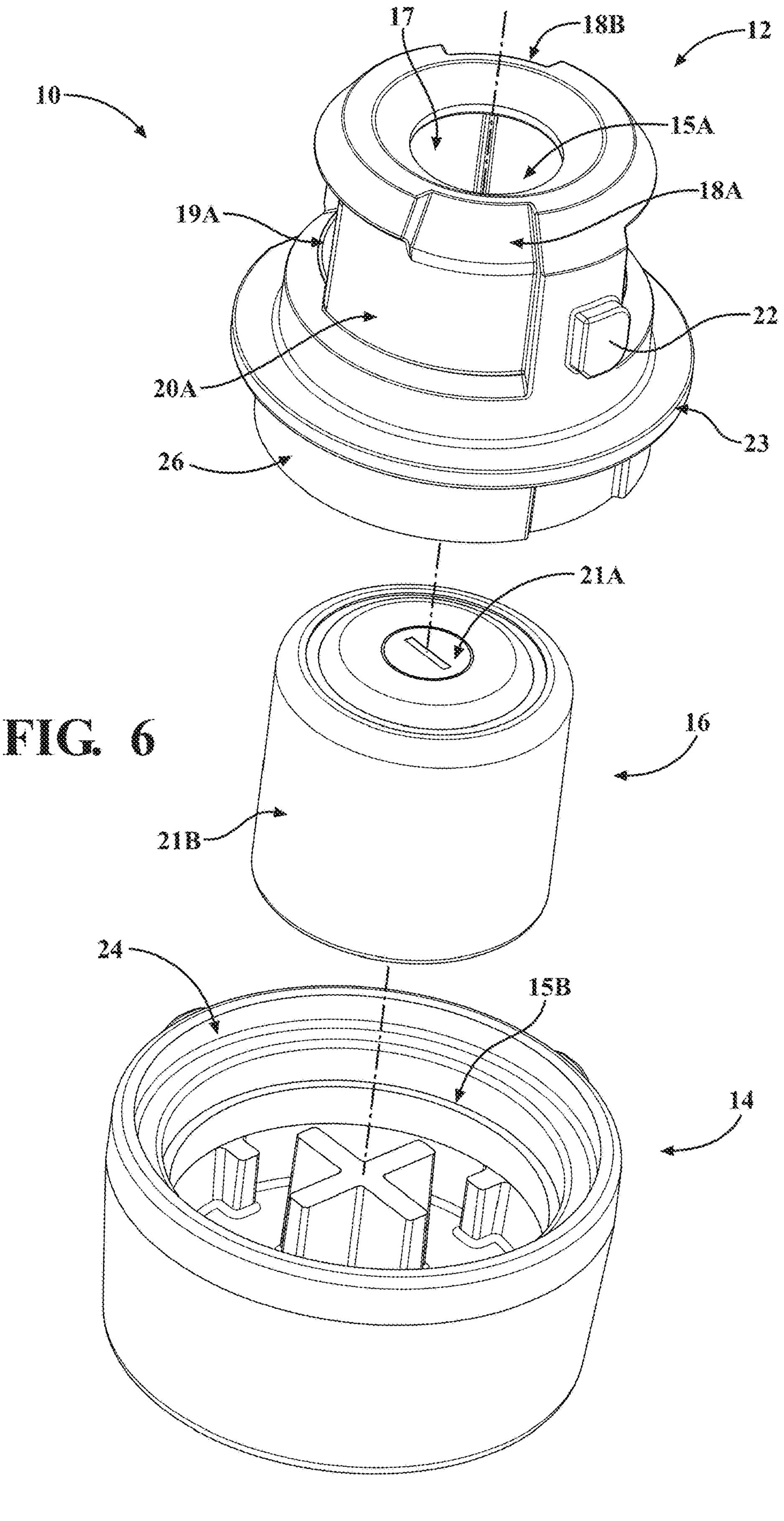
FIG. 6 is a partial exploded view of the battery assembly of FIGS. 1-5, the battery assembly including a housing having a first portion and a second portion configured to at least partially enclose a battery, according to one implementation.
Figure 7:
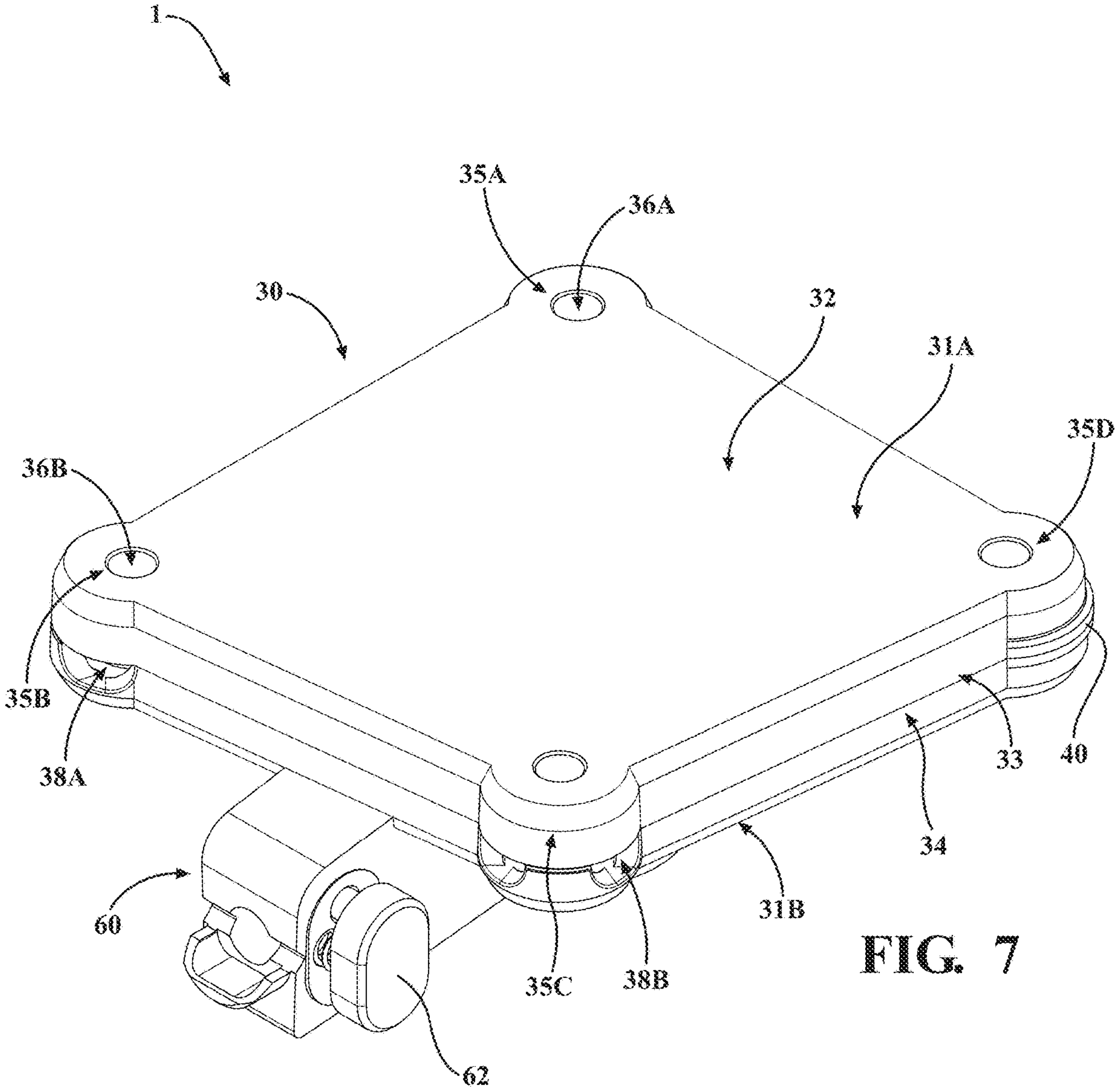
FIG. 7 is a perspective view of one implementation of a tracker including a tracker housing and a tracker mount.
Figure 8:
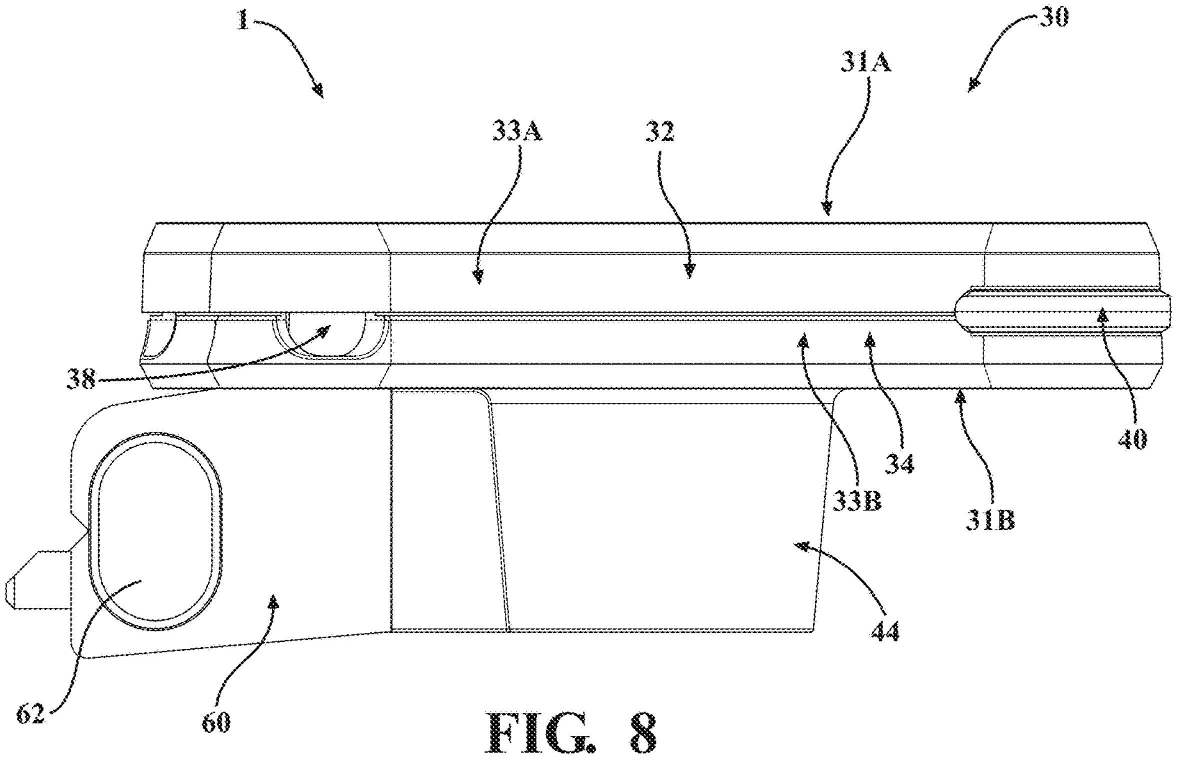
FIG. 8 is a side view of the tracker of FIG. 7, illustrating a first side of the tracker.
Figure 9:
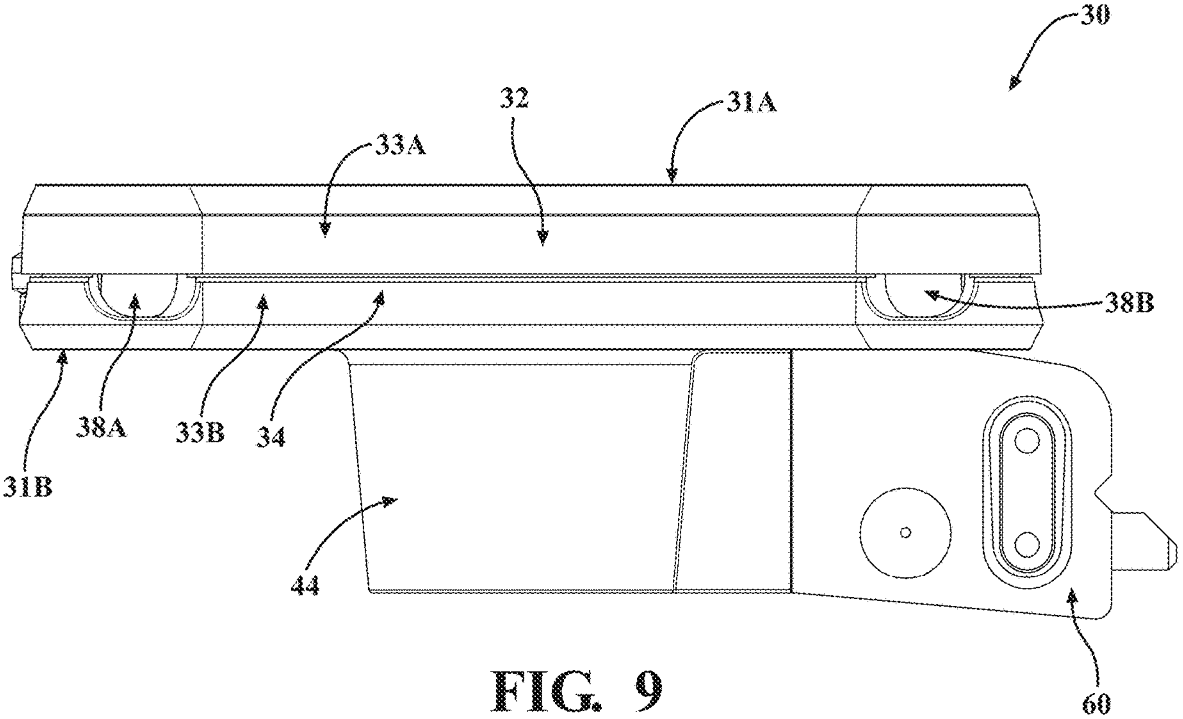
FIG. 9 is a side view of the tracker of FIG. 7, illustrating a second side of the tracker.
Figure 10:
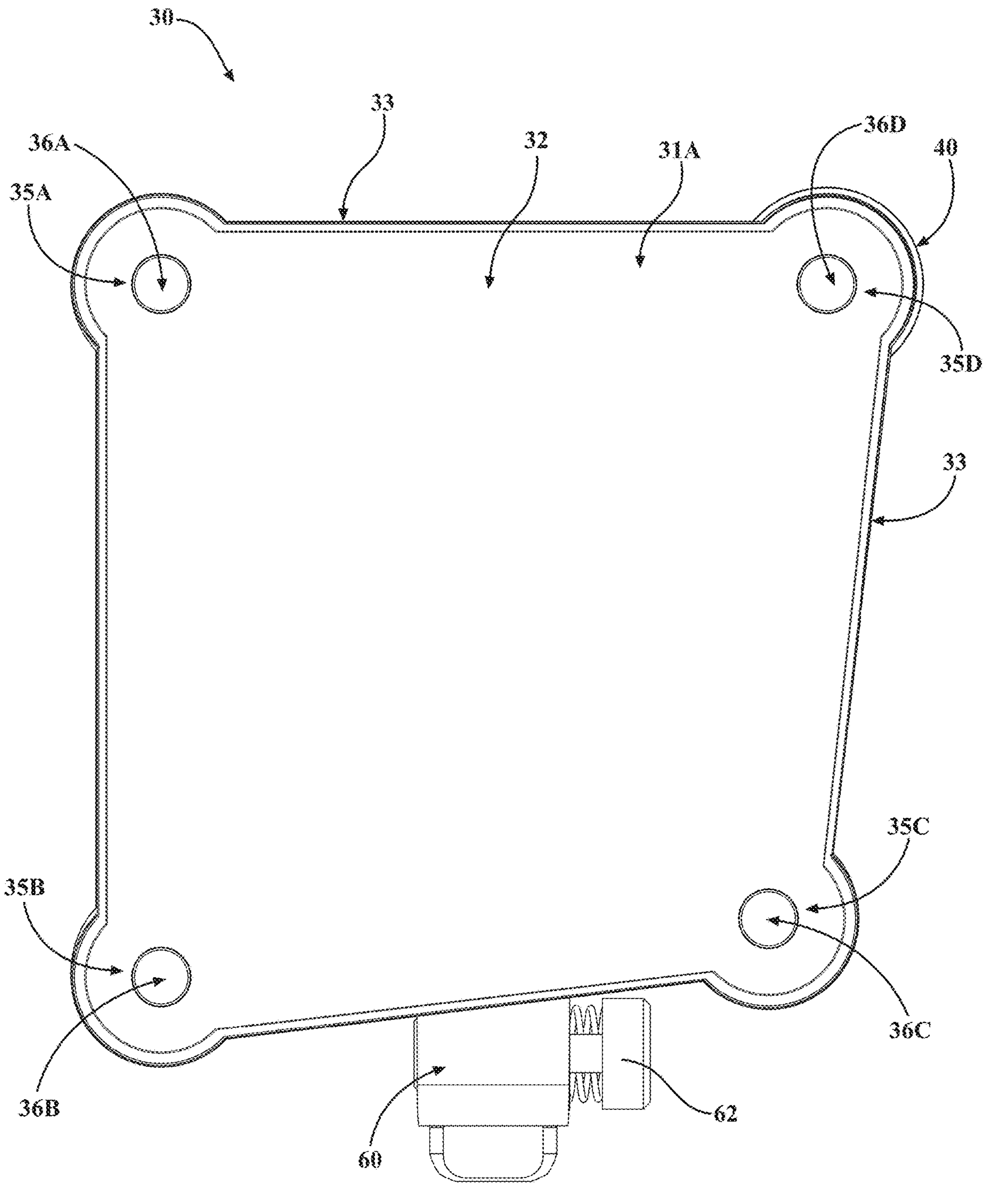
FIG. 10 is a top view of the tracker of FIG. 7, the tracker housing including a top portion defining openings through which a fiducial may be observed.

The first portion 12 and second portion 14 may be separable from one another to allow the battery 16 to be inserted and/or installed between the two portions 12, 14. The first portion 12 and the second portion 14 of the battery assembly 10 may comprise complementary coupling features 24, 26 to allow for removably coupling the first portion 12 and the second portion 14 to one another. For example, as best illustrated in FIG. 6, the first portion 12 and the second portion 14 may comprise complementary coupling features 24, 26 configured to create a snap fit or press fit. This may include one of the first or second portion 12, 14 defining a coupling feature 24, 26 including a recess and the other of the first and second portion 12, 14 defining a complementary coupling feature 24, 26 including protrusion or detent configured to be seated in the recess when the first and second portions 12, 14 are coupled together. The recess and/or protrusion may be arranged annularly about the respective first and second portions 12, 14. Alternatively, the complementary coupling features 24, 26 may include one or more separate features, such as an arrangement of recesses formed as indent and corresponding protrusions/detents on the opposing portion 12, 14. The first portion 12 and the second portion 14 may also include complementary coupling features 24, 26 comprising a threaded or interlocking configuration that is engaged by rotating one of the first portion 12 or the second portion 14 relative to the other to removably couple them together. For example, the coupling features 24, 26 of the first and second portions 12, 14 may comprises reciprocal threaded portions that are configured to rotationally engage one another and couple the first and second portions 12, 14 to one another. Alternatively, the coupling features 24, 26 of the first and second portions 12, 14 may comprise a groove(s) and complementary detent(s) arranged on the first and second portions 12, 14 and configured to couple the first and second portions 12, 14 via a quarter turn or similar fastening procedure. The second portion 14 may comprise a plurality of finger grips that extend from the surface thereof to enable a user to grasp and easily rotate the second portion 14.

The first portion 12 may define a first aperture 17 and/or a second aperture 19A, 19B. The first aperture 17 and/or the second aperture 19A, 19B may be positioned on the first portion 12 and configured to provide access to the battery contacts 21A, 21B on the battery 16 from outside the housing 12, 14. For example, the first aperture 17 may be defined in a distal (top) surface of the first portion 12 to provide access to a first battery contact 21A on the battery 10. The second aperture 19A, 19B may be defined in a side surface of the first portion 12 to provide access to a second electrical contact 21B on the battery 10. It is further contemplated that the first portion may define two or more second apertures 19A, 19B arranged on the side surface of the first portion 12. For example, as illustrated in FIGS. 1-6, the first portion 12 may be configured to define a pair of second aperture 19A, 19B on opposed sides of the first portion 12.

The first portion 12 may also be shaped and/or configured to define features for removably coupling the battery assembly 10 to the tracker 30. For example, the first portion 12 may define one or more vertical channels 18A, 18B or chamfers for receiving and/or orienting the battery assembly 10 relative to complementary features of the tracker 30. The first portion 12 may further define a lateral channel 20A, 20B in connection and/or communication with the vertical channels 18A, 18B. The lateral channel 20A, 20B may be configured to receive the complementary features of the tracker 30, allow the rotation of the battery assembly 10 relative to the tracker 30. The vertical channels 18A, 18B and/or the lateral channel 20A, 20B may further be configured to position a complementary feature on the tracker relative to at least one of the second aperture(s) 19A, 19B to form an electrical connection between the battery 16 and the tracker 30. For example, vertical channels 18A, 18B and/or the lateral channel 20A, 20B may define a pathway to guide and/or position the electrical connector 45 of the tracker 30 within the apertures 17, 19A, 19B and relative to the battery contacts 21A, 21B on the battery 16. For example, the vertical channels 18A, 18B of the battery housing 12, 14 may receive the electrical connector 45 of the tracker 30 and direct it to the lateral channel 20A, 20B as the battery assembly 10 is inserted into the tracker 30. The lateral channel 20A, 20B may then direct the electrical connector 45 of the tracker 30 to one of the second aperture(s) 19A, 19B as the battery assembly 10 is related relative to the tracker 30 positioning the electrical connector 45 of the tracker 30 in contact with one of the battery contacts 21A, 21B of the battery to form an electrical connection between the battery 16 and he tracker 30 through one of the second aperture(s) 19A, 19B. This will be described in greater detail below.

In addition to alignment and/or positioning the battery assembly 10 relative to the tracker 30, the vertical channels 18A, 18B and/or the lateral channel 20A, 20B may also be configured to couple the battery assembly 10 to the tracker 30. As illustrated in the figures, the vertical channels 18A, 18B may comprise a ramped surface leading to the lateral channel 20A, 20B. The ramped surface of the vertical channel 18A, 18B may allow for the use of a biased component on the tracker 30, such as the electrical connector 45, to create a friction fit, compressive fit, interference fit, or the like between vertical channel 18A, 18B and/or the lateral channel 20A, 20B to couple the battery assembly 10 to the tracker 30.

The battery assembly 10 may further comprises an attachment member 22 configured to removably secure the battery assembly 10 to the device it is intended to provide power to, such as the tracker 30. For example, the first portion 12 may define one or more attachment members 22A, 22B defined as a detent or protrusion, as is illustrated in FIGS. 1-6. The attachment members 22A, 22B may be symmetrically about and/or mirror opposites of one another. For example, as illustrated in FIGS. 1-6, the housing 12, 14 comprises a first attachment member 22A and a second attachment member 22B arranged as mirror opposites on the first portion 12. While only a first attachment member 22A and a second attachment member 22B are illustrated in the Figures, it is contemplated that the battery assembly 10 may comprise only a single attachment member 22, or may comprises a plurality of attachment members 22A, 22B symmetrically spaced about the housing 12, 14. The attachment member(s) 22A, 22B defined as detent or protrusion extending from a surface of the first potion 12 of the battery assembly 10 may be configured to cooperate with a groove or channel 46A, 46B on the tracker 30 configured to removably secure the battery assembly 10 to the tracker 30. As will be described in greater detailed below, the groove or channel 46A, 46B on the tracker 30 may be shaped and/or arranged to create an interlocking coupling mechanism or interference fit with the attachment member(s) 22A, 22B of the battery assembly 10. One advantage of having the attachment members 22A, 22B arranged as mirror opposites or symmetrically about the housing 12, 14 of the battery assembly 10 is that it allows the battery to be easily installed within the tracker 30 in the nearest of a plurality of orientations relative to the tracker 30. For example, where the battery assembly 10 includes the first attachment member 22A and the second attachment member 22B arranged as mirror opposites, the battery assembly 10 may be installed within the tracker 30 via the closest of either of two orientations. The attachment members 22A, 22B can be utilized as the primary means of coupling the battery assembly 10 to the tracker 30 and/or in addition to/combination with the vertical channels 18A, 18B and/or the lateral channel 20A, 20B described above.

Figure 2:
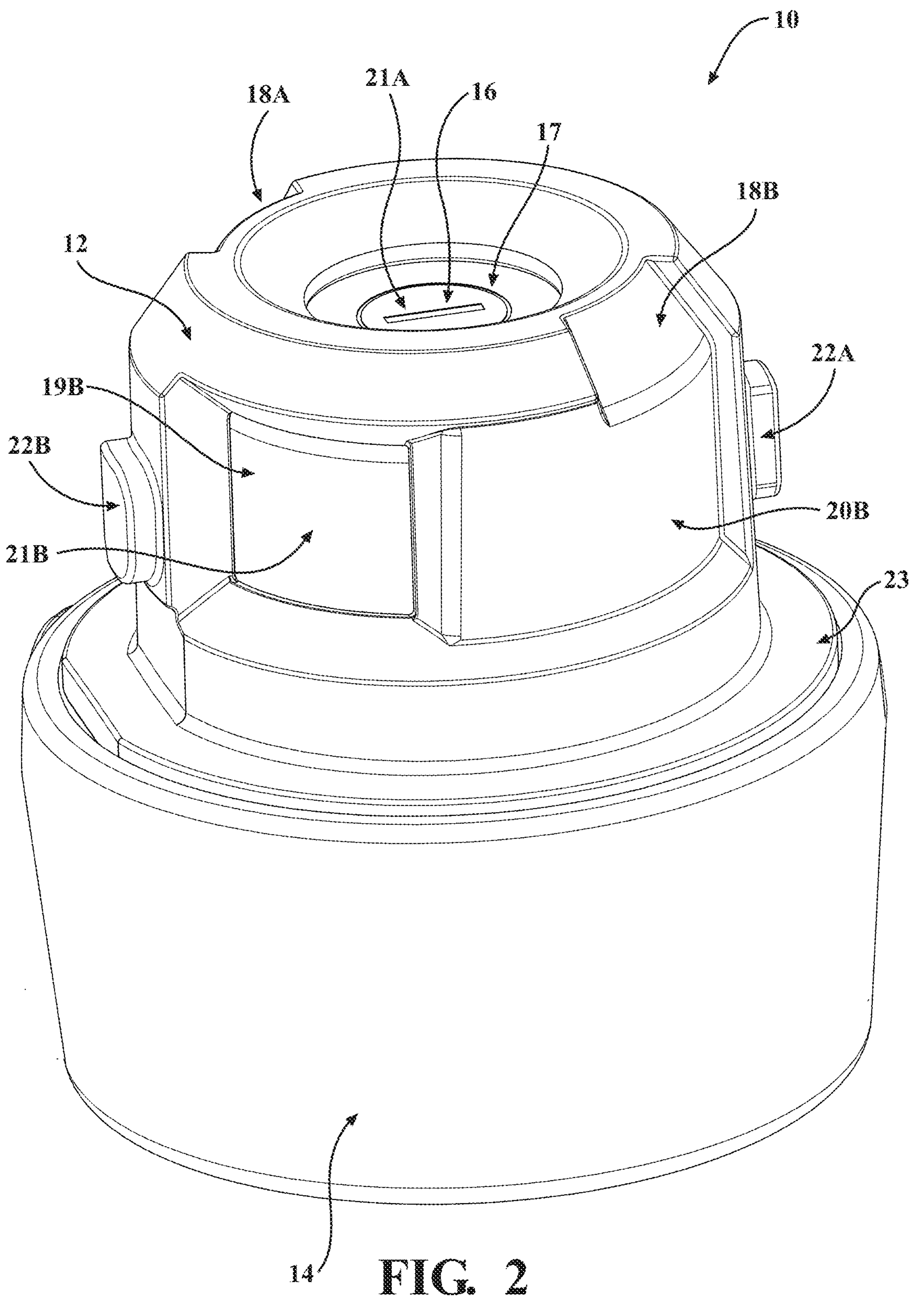
FIG. 2 is an alternative perspective view of the battery assembly of FIG. 1, illustrating additional features on battery assembly.
Figure 3:
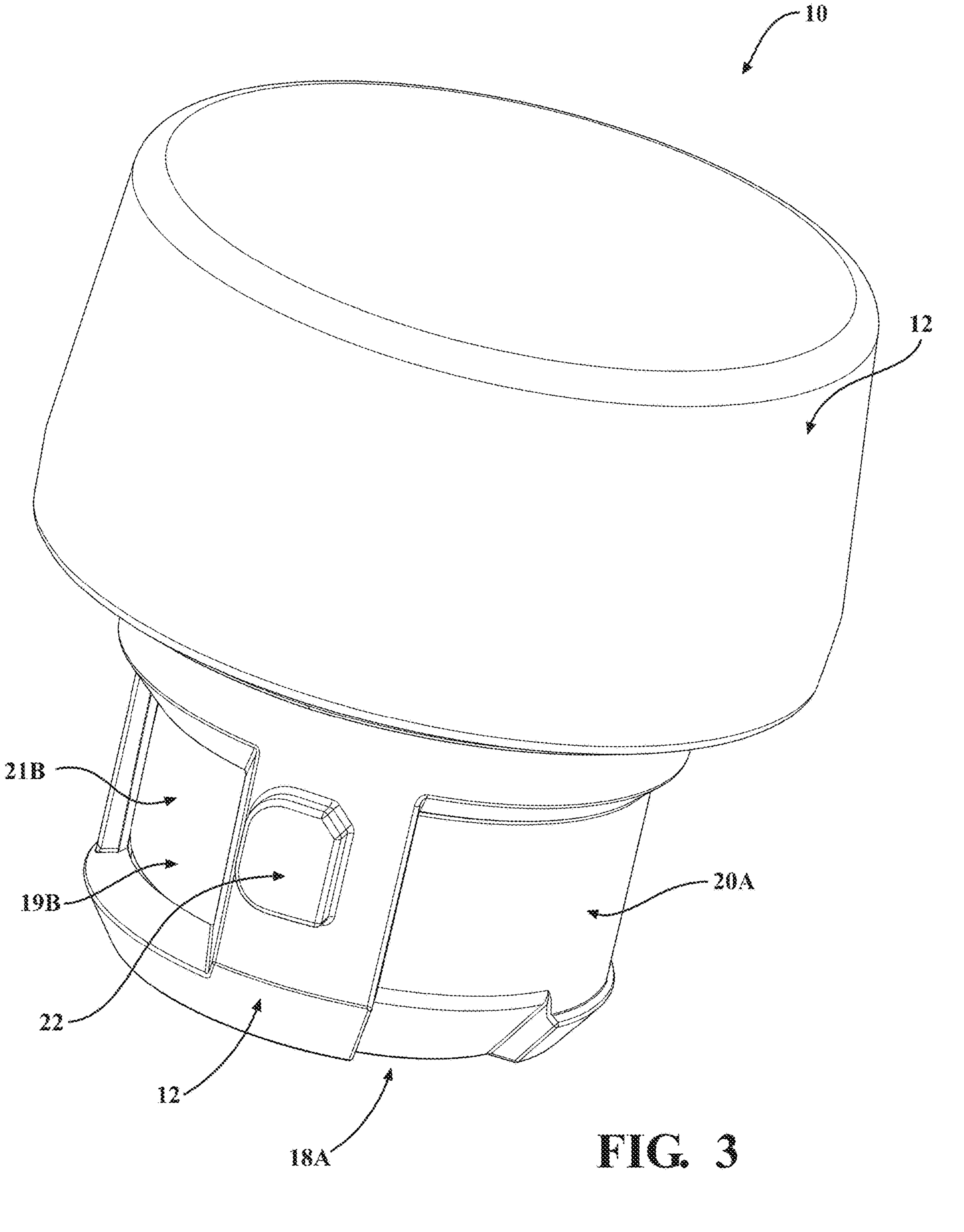
FIG. 3 is an alternative perspective view of the battery assembly of FIGS. 1 and 2, illustrating a bottom portion of the battery assembly.
Figure 4A:
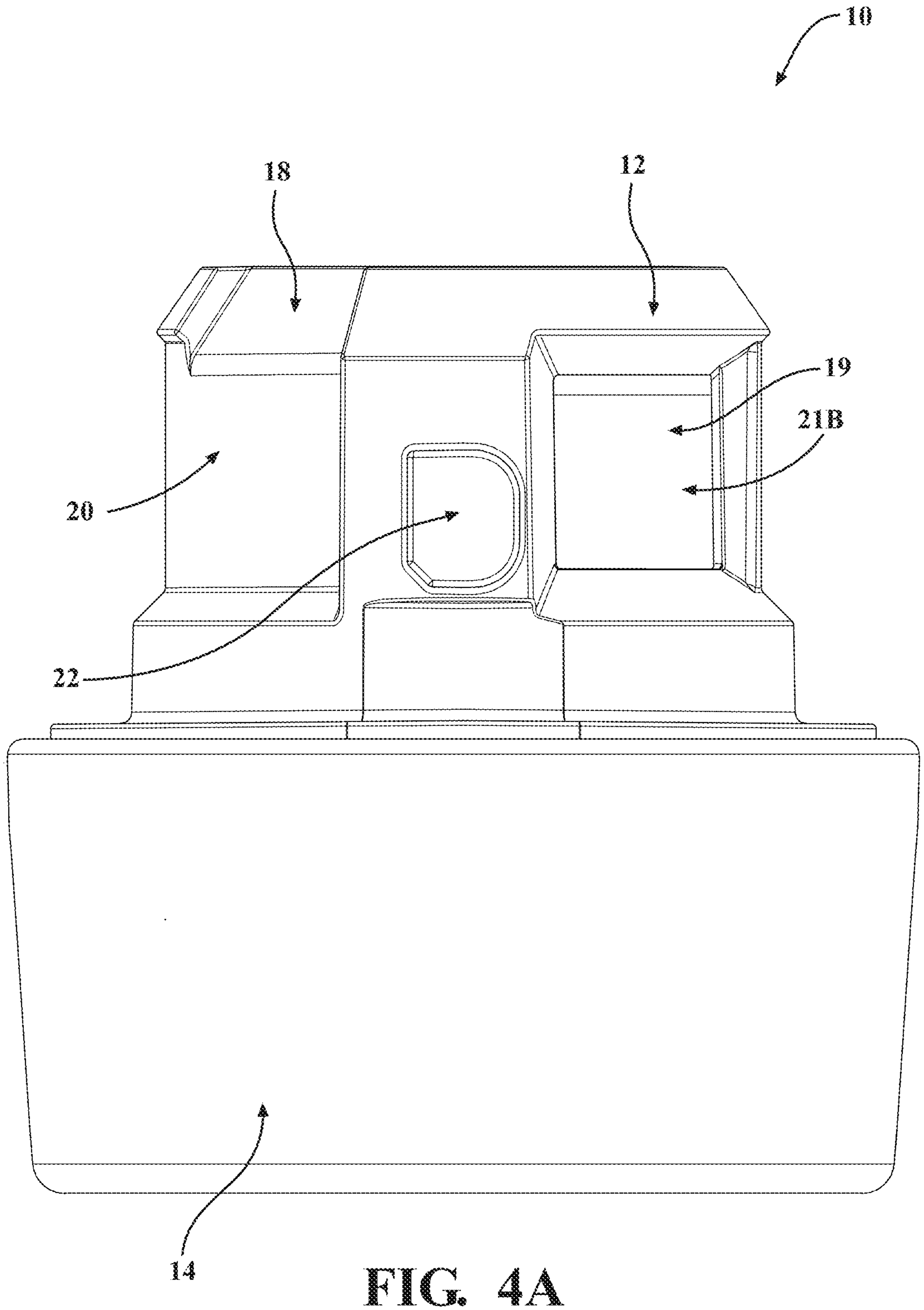
FIG. 4A is a side view of the battery assembly of FIGS. 1-3, illustrating the battery assembly as viewed from a first direction.
Figure 4B:
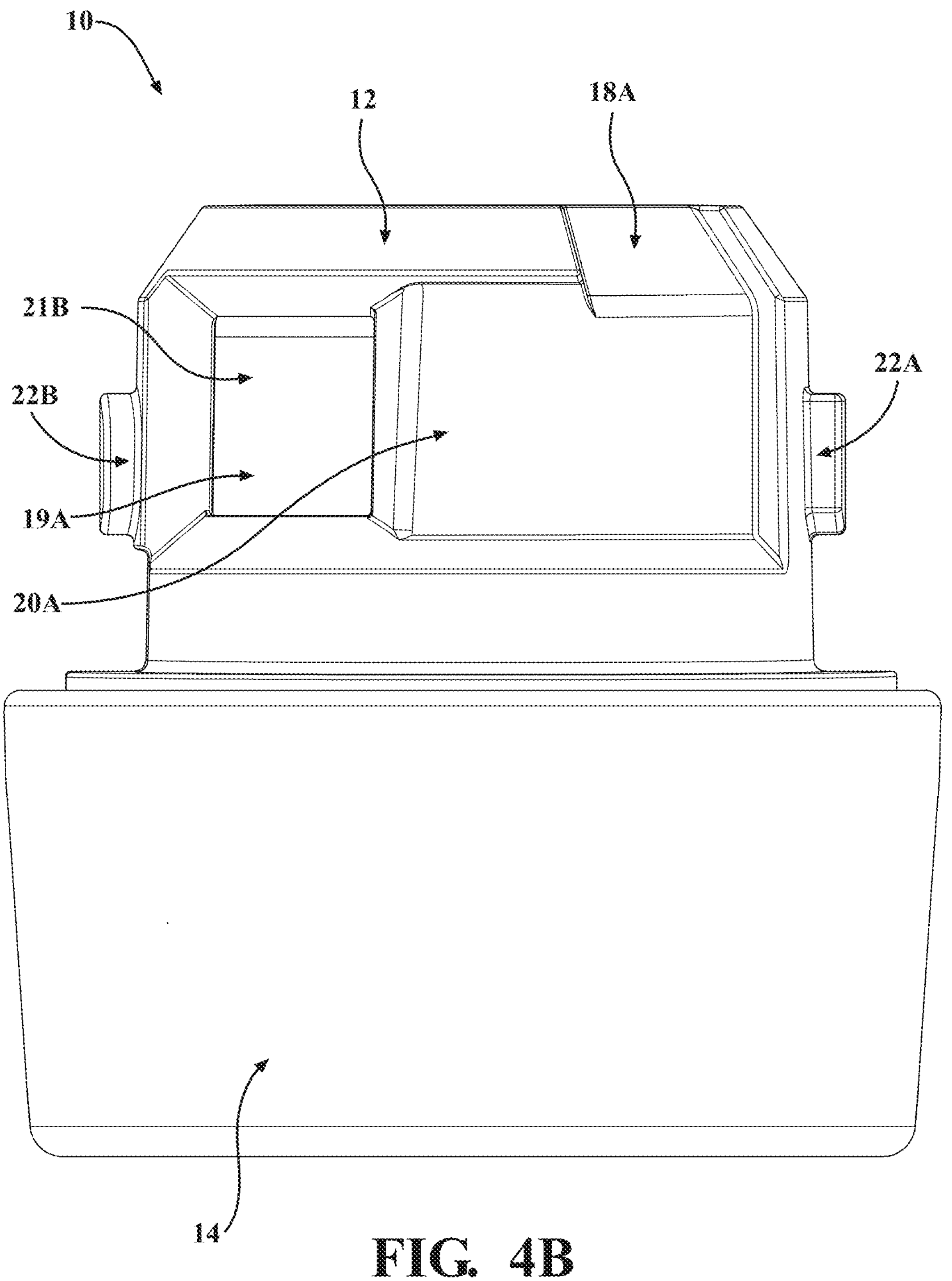
FIG. 4B is a side view of the battery assembly of FIGS. 1-3, illustrating the battery assembly as viewed from a second direction.
Figure 5:
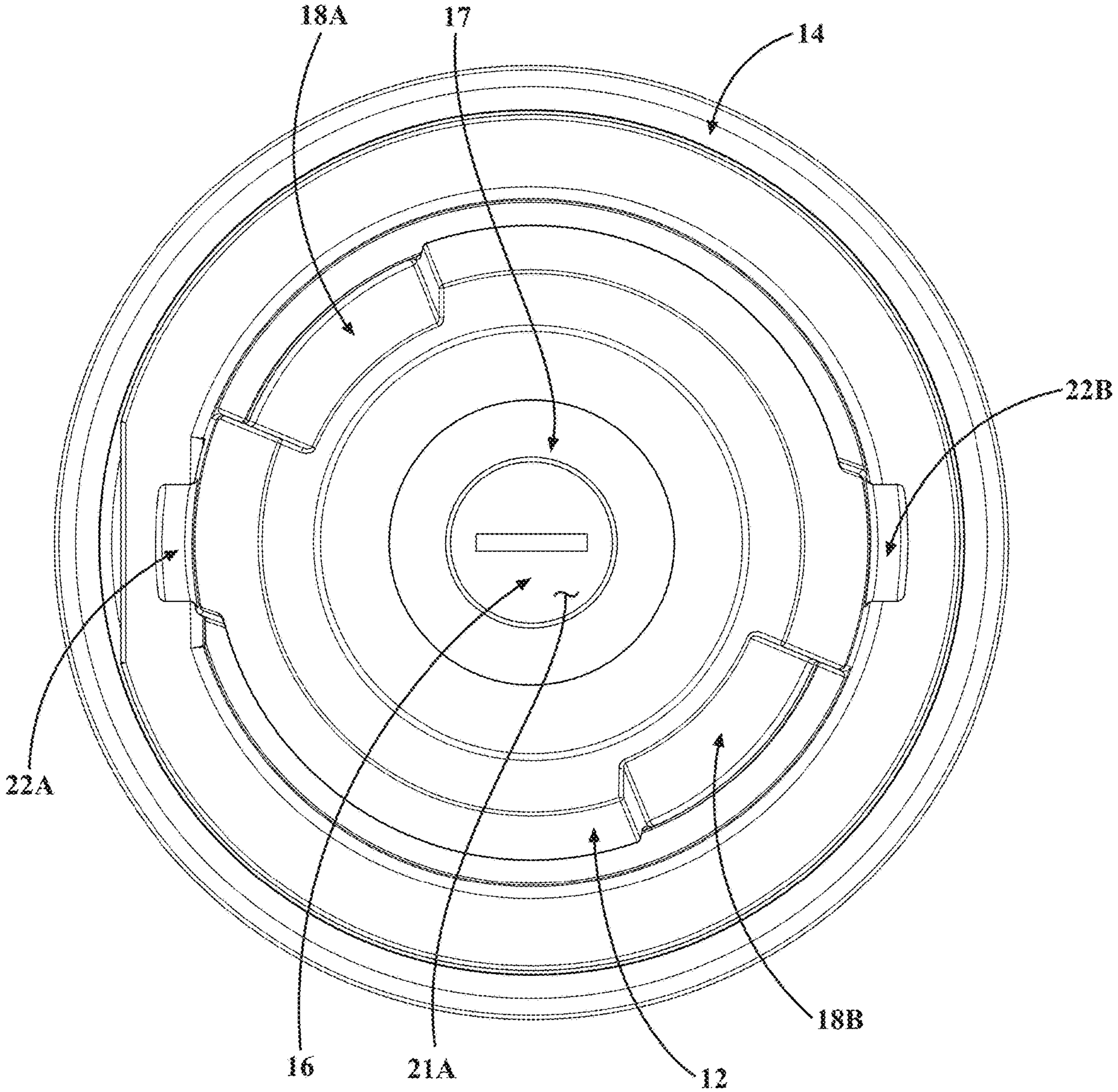
FIG. 5 is a top view of the battery assembly of FIGS. 1-4B.

The battery assembly 10 may further comprise a seal 23, such as a gasket or O-ring, configured to create a seal between the battery assembly 10 and the device it is coupled to, such as the tracker 30. As illustrated in FIGS. 1, 2, and 6, the seal 23 may be disposed on or around the outside edge of the shoulder defined by the first and/or second portion 12, 14. In one configuration, the seal 23 may be a removable gasket, such as an O-ring. As illustrated in the Figures, the seal 23 is a thermal plastic elastomer (TPE) permanently attached to the first portion 12 of the battery assembly. The seal 23 may be attached by a chemical and thermal bond.

While the battery assembly 10 is described as being couplable to the tracker 30, it is also contemplated that the battery assembly 10 described herein may be configured and/or modified to be coupled to any item requiring a removable and/or replaceable power source. For example, the battery assembly 10 may include a battery sized to operate/power a hand tool, such as a surgical instrument 70 including a drill or saw, with the housing 12, 14 being configured and adapted to be coupled to the hand tool 70 to create an electrical connection.

B. Surgical Tracker Implementations

Referring to FIGS. 7 to 13, one example configuration of the tracker 30 is illustrated. The tracker 30 may be powered by the battery assembly 10 described above as part of the tracker assembly 1. The tracker 30 may comprise a tracker body 32, 34 formed from a first body member 32 and a second body member 34. The tracker body 32, 24 includes a first surface 31A, an opposed second surface 31B, and a plurality of side surfaces 33 connecting between the first and second surfaces 31A, 31B. The first body member 32 and second body member 34 may be formed from a material that is not susceptible to damage when exposed to a sterilant or repeatedly subjected to a sterilization process. It is also contemplated that the first body member 32 and the second body member 34 may be formed from a plastic or similar polymeric material, steel, carbon, titanium, or similar material. The body members 32, 34 can also be integrally formed a single-unitary material.

The tracker body 32, 34 may comprise any shape, such as a square, rectangle, x-shape, circle, or the like. As illustrated in the figures, the tracker body 32, 34 may be configured in a generally square shape, with an arm 35A, 35B, 35C, 35D extending outward from the tracker body 32, 34. For example, the tracker body 32, 34 may be shaped such that an arm 35A, 35B, 35C, 35D extends from each corner. As illustrated in the figures, the tracker body 32, 34 may include four arm 35A, 35B, 35C, 35D extending outward from the tracker body 32, 34, each arm 35A, 35B, 35C, 35D extending in a different direction from a central portion of the tracker body 32, 34. Each of the arms 35A, 35B, 35C, 35D may be configured to define an aperture 36A, 36B, 36C, 36D. While not required, each of the apertures 36A, 36B, 36C, 36D may be covered by a window or similar coating that allows for light to pass through and/or be visualized through the aperture 36A, 36B, 36C, 36D.

Figure 13:
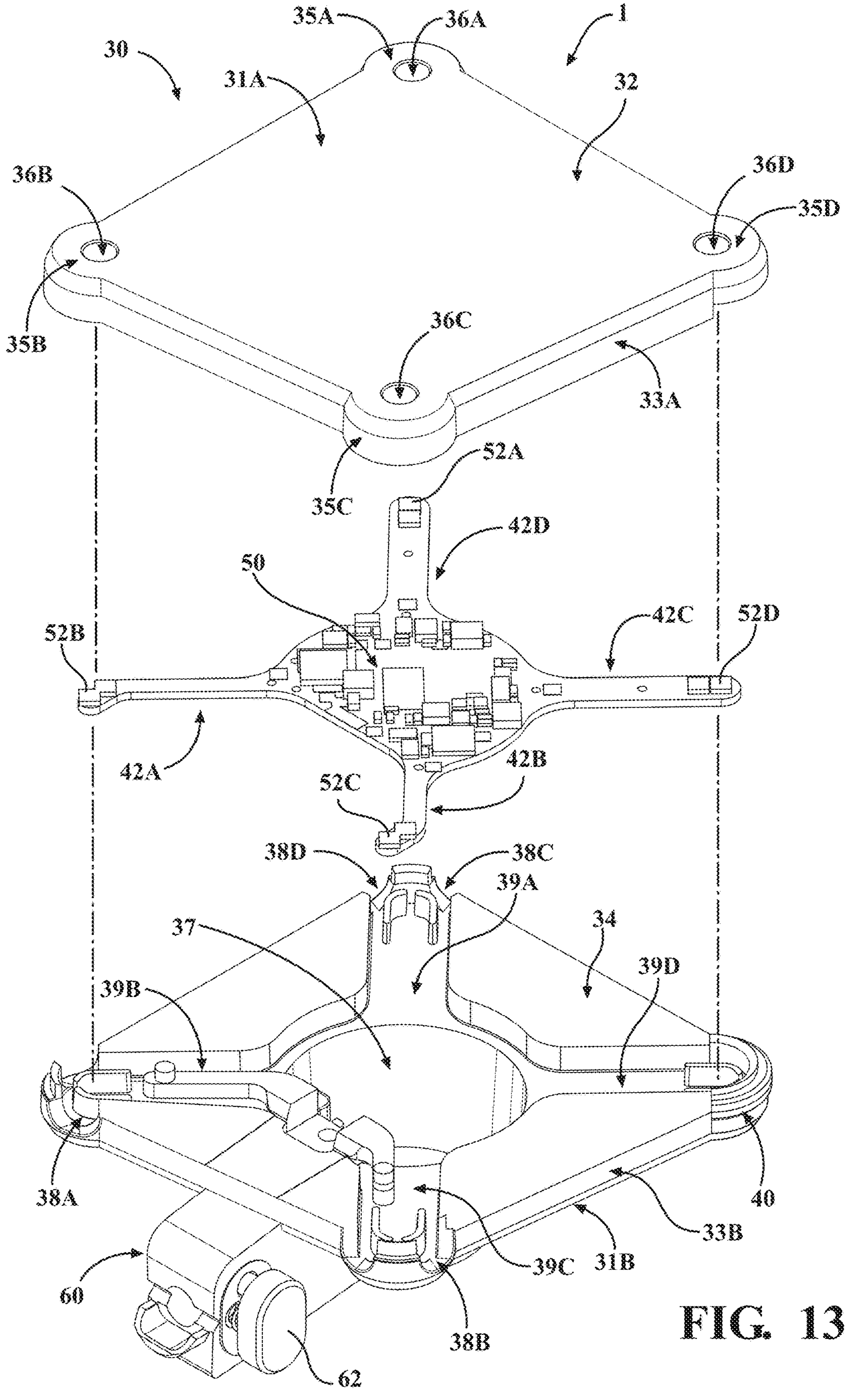
FIG. 13 is a partially exploded view of the tracker of FIG. 7, illustrating the housing including the top and bottom portions and a printed circuit board arranged to be disposed between the top and bottom portions of the housing.

As shown in FIG. 13, a chamber 37 is defined between the first and second surface 31A, 31B of the first body member 32 and the second body member 34. The first body member 32 and/or the second body member 34 may further define one or more channels 39A, 39B, 39C, 39D that extend outward from the chamber 37. The one or more channels 39A, 39B, 39C, 39D may extend outward from the chamber 37 toward one of the exterior surfaces 31A, 31B of the tracker body 32, 34. For example, as illustrated in the figures, a channel 39A, 39B, 39C, 39D extends outward from the chamber 37 to each of the arm 35A, 35B, 35C, 35D defined by the tracker body 32, 34 and extending through the side surface 33 of the tracker body 32, 34. While not shown in the figures, it is further contemplated that the channel 39A, 39B, 39C, 39D may extend outward from the chamber 37 and extend through either of the first or second surface 31A, 31B of the tracker body 32, 34.

The exterior surfaces 31A, 31B of the tracker body 32, 34 may further define one or more openings 38, each of the one or more openings in fluid communication with one of the one or more channels 39A, 39B, 39C, 39D. The openings 38 in conjunction with the channels 39A, 39B, 39C, 39D form a pathway to/from and through the chamber 37 of the tracker body 32, 34 to allow sterilant to enter/exit through the chamber 37. The channels 39A, 39B, 39C, 39D and opening(s) 38 also serve as a drain for any debris, sterilant, or the like that may enter the channel 39A, 39B, 39C, 39D and/or chamber 37 to drain from the tracker body 32, 34. As illustrate in the Figures, the second body 34 of the tracker body 32, 34 defines the at least one opening 38. Alternatively, it is also contemplated that the opening may be defined by the first body 32 of the tracker body 32, 34. Furthermore, while the opening 38 is illustrated as two openings 38 defined proximate the corner(s) of the tracker body 32, 34 and in communication with the channels 39A, 39B, 39C, 39D, it is further contemplated that there may only be a single opening defined in the first and/or the second body 32, 34 of the tracker body 30 proximate the corner(s) of the tracker body 32, 34. While not illustrated in the figures, it is further contemplated that the one or more channels 39A, 39B, 39C, 39D may extend from the chamber 37 toward any side or exterior surface of the tracker body 32, 34, and the openings may be defined in a side or exterior surface of the tracker body 32, 34 to be in fluid communication with each of the one or more channels 39A, 39B, 39C, 39D.

The tracker 30 may further comprise a printed circuit board (PCB) 50. The PCB 50 may be shaped to correspond to the shape of the chamber 37 and channels 39A, 39B, 39C, 39D defined by the tracker body 32, 34. For instance, assuming the chamber 37 and channels 39A, 39B, 39C, 39D defined by the tracker body 32, 34 are arranged in an X-shape, the PCB 50 may be configured to have a shape conforming to the X-shape (e.g., including leg portions 42A, 42B, 42C, 42D corresponding to the channels 39A, 39B, 39C, 39D formed in the tracker body 32, 34). The PCB 50 may include a central portion and a plurality of leg portions 42A, 42B, 42C, 42D that extend from the central portion of the PCB 50. While the tracker 30 is illustrated in the figures as having a generally X-shaped PCB 50, it is contemplated that the PCB 50 may be formed in any number of suitable shapes, such as a square, rectangle, disk, triangle, plate, circle, sphere, trapezoid cube, or the like that correspond to and/or fit within the shape of the chamber 37 and channels 39A, 39B, 39C, 39D defined by the tracker body 32, 34.

Figure 14:
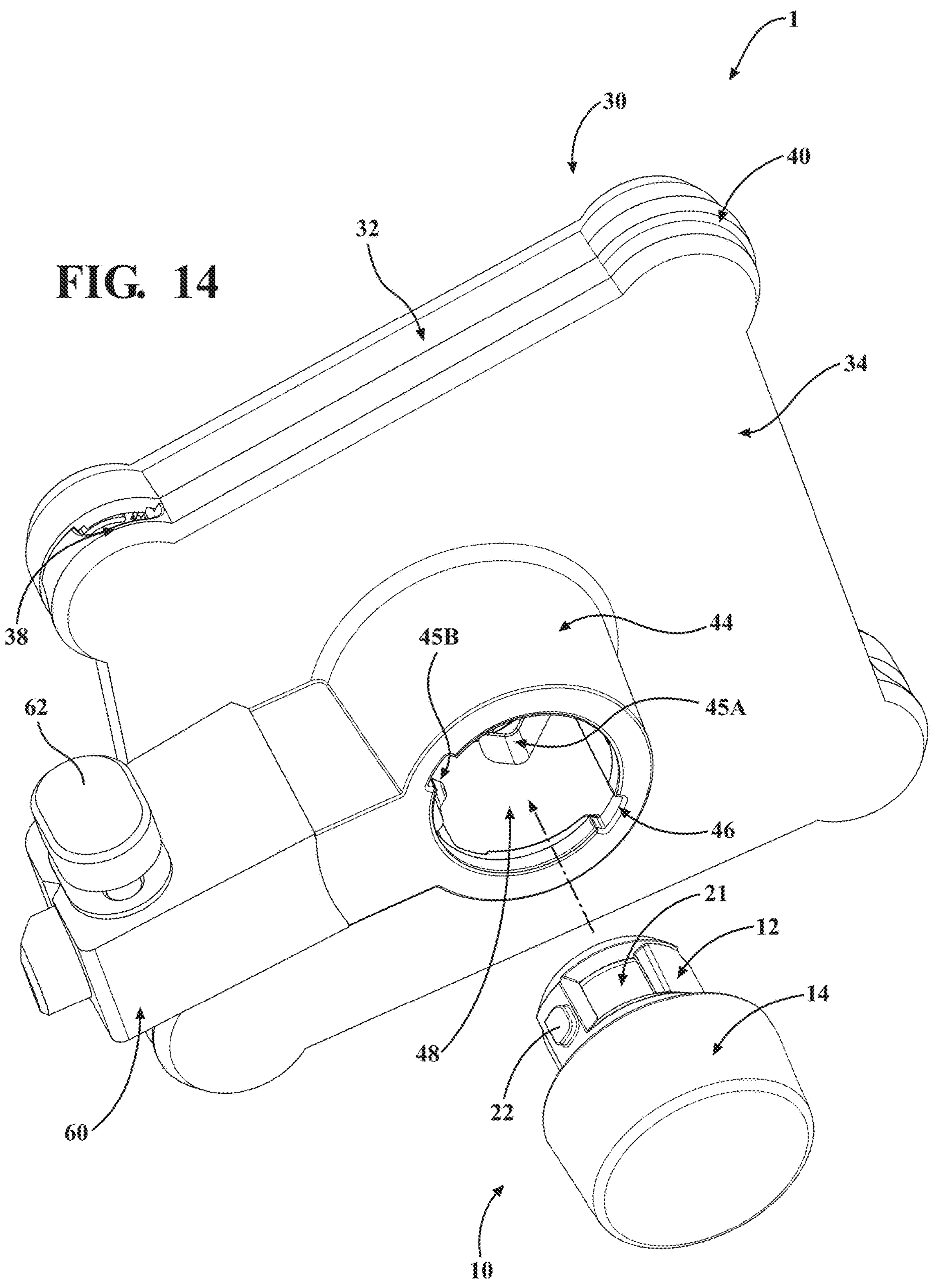
FIG. 14 is a perspective view of a partially exploded tracker assembly including the tracker of FIGS. 7-13 and the battery assembly of FIGS. 1-6.
Figure 15:
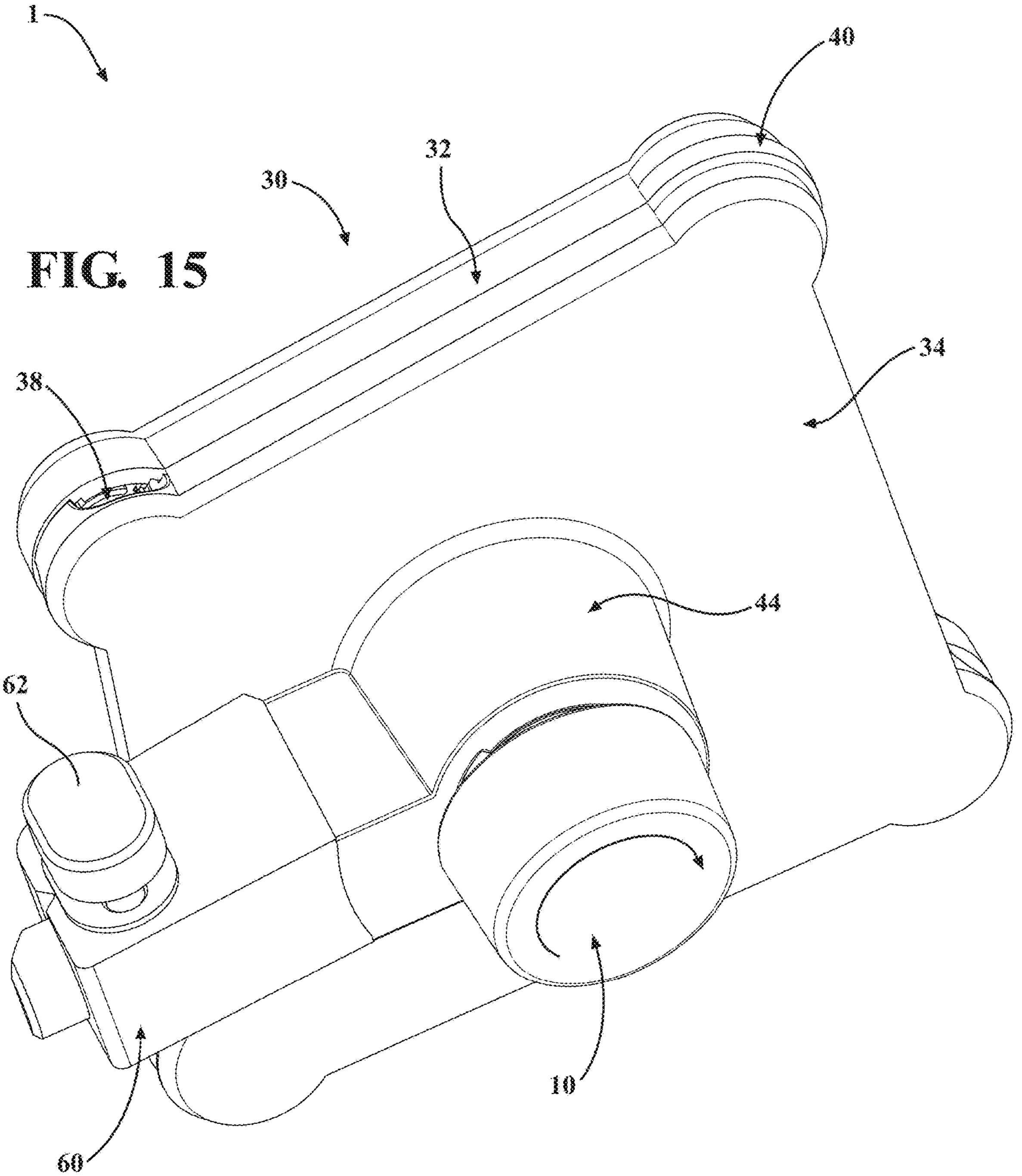
FIG. 15 is a perspective view of the tracker assembly of FIG. 14 including the battery assembly coupled to the tracker.

The PCB may further comprise at least one marker 52A, 52B, 52C, 52D which may also be referred to as fiducials or tracking element. The PCB 50 may include traces connecting the markers 52A, 52B, 52C, 52D, a control circuit (not shown), and electrical connector 45 for forming an electrical connection with the battery 16. The markers 52A, 52B, 52C, 52D may be configured as light sources or reflective type markers 52A, 52B, 52C, 52D. The markers 52A, 52B, 52C, 52D may be coupled to the PCB 50 in a unique pattern or arrangement that is identifiable to a navigation system (not shown). For example, as illustrated in FIG. 13, markers 52A, 52B, 52C, 52D are disposed on each of the leg portions 42A, 42B, 42C, 42D of the PCB 50. The markers 52A, 52B, 52C, 52D may be positioned on the PCB 50 so that each of the markers 52A, 52B, 52C, 52D is visible through one of the apertures 36A, 36B, 36C, 36D defined in the tracker body 32, 34. For example, as illustrated in FIG. 13, the markers 52A, 52B, 52C, 52D are arranged on the leg portions 42A, 42B, 42C, 42D of the PCB such that when the tracker body 32, 34 is assembled with the PCB disposed in the chamber 37, the markers 52A, 52B, 52C, 52D are positioned to be visible through the apertures 36A, 36B, 36C, 36D. In the instance of PCB 50 including markers 52A, 52B, 52C, 52D as a light source, such as LEDs, the tracker 30 may also include the battery assembly 10 described above that is coupled to the tracker 30. For example, as illustrated in FIGS. 14 and 15, the battery assembly 10 may be coupled to the underside of the tracker 30 and electrically connected to each of the markers 52A, 52B, 52C, 52D of the PCB 50. Some implementations of LED tracking markers are shown and described in U.S. Patent Application Publ. No. 2019/0321108 and International Application No. PCT/IB2020/060187, both of which are hereby incorporated by reference.

The markers 52A, 52B, 52C, 52D of the PCB 50 described above may thus be arranged in a predefined pattern on the PCB 50 and to be visible through the 36A, 36B, 36C, 36D such that the pattern is recognized by the navigation system to track a surgical object or instrument 70 associated with the tracker 30. Each marker 52A, 52B, 52C, 52D may be a light emitting diode (LED), or more particularly, an infrared LED (IR-LED), that is configured to emit light at a wavelength corresponding to the range of wavelengths detectable by the camera unit of the navigation system.

Referring to FIGS. 7 to 13, an example configuration of a tracker 30 is illustrated. As described above, during a surgical procedure, the tracker 30 including one or more markers 52A, 52B, 52C, 52D may be coupled to the surgical object to allow the navigation system to determine the position and/or orientation of the object. The markers 52A, 52B, 52C, 52D may be active light sources (e.g., LEDs) driven by an electrical current in a predefined pattern, and the navigation system may be configured to detect the pose of the tracker 30, and correspondingly the pose of the surgical object by detecting light signals received from the markers 52A, 52B, 52C, 52D and matching the detected light signals to the predetermined pattern. While the tracker 30 described herein may be sterilizable and reusable, it is also contemplated that the tracker 30 may be a disposable tracker. An implementation of a disposable tracker is shown and described in International Application No. PCT/IB2020/059064, which is hereby incorporated by reference.

The PCB 50 may further be configured to survive exposure to a sterilant and/or sterilization process. Based on the design of the tracker body 32, 34 being configured to allow sterilant to flow into and/or contact all surfaces of the tracker body 32, 34 the PCB 50 is likely to be exposed to sterilant when the tracker 30 is subjected to a sterilization process. In order to prevent damage to the PCB 50 by the sterilant and/or the sterilization process, the exterior surface(s) of the PCB 50 may be protected by the application of a conformal coating 520, which creates a barrier on the PCB 50 preventing the ingress of debris and/or fluids. Exemplary conformal coatings may comprise a parylene film applied to assembled PCBs 50. This may include application of the parylene film and/or coating being applied to leg portions 42A, 42B, 42C, 42D, the markers 52A, 52B, 52C, 52D, and/or the other components of the PCB 50 during manufacturing.

As described above, the tracker 30 may be configured to be subjected to a sterilization process to allow for repeated use of a single tracer 30. A method of sterilizing the surgical tracker 30 may comprise applying a sterilant to the surgical tracker 30 as part of a sterilization process and enabling at least a portion of the sterilant to flow through the channels 39 to enter the interior chamber 37 and contact the PCB 50. The method may further comprise draining the sterilant from within the interior chamber 37 through the channel 39 and/or openings 38 defined by the tracker body 32, 34 after completion of the sterilization process.

In some configurations, the tracker 30 may further comprise circuitry for a status indicator 40 electrically coupled to at least one of the markers 52A, 52B, 52C, 52D, the battery 16, and/or the PCB 50. In one implementation, the status indicator 40 may comprise an LED that emits visible (i.e., non-infrared) light so that a surgeon can easily see a status of the tracker 30. The status can relate to the tracker 30 properly functioning or malfunctioning. For example, the status indicator 40 may emit visible light to indicate when the tracker 30 is operating correctly and/or that the markers 52A, 52B, 52C, 52D are in view of the navigation system (established line-of-sight). Alternatively, the status indicator 40 may be configured to emit visible light to indicate when the tracker 30 is not operating correctly and/or one or more of the markers 52A, 52B, 52C, 52D are not in view of the navigation system (lost line-of-sight). The status indicator 40 may also be configured to provide additional diagnostic or operational information to the surgeon, such as remaining battery capacity of the battery assembly 10. For example, the status indicator 40 may flash or blink when the battery 16 voltage corresponds to a first level, and when the battery 16 voltage corresponds to a second level the status indicator 40 may turn off. The status indicator 40 may further be implemented with more than one LED, or an LED capable of illuminating with more than one color. If more than one LED is used the voltage level of the battery 16 may correspond to the number of LEDs that are concurrently illuminated. If multi-color LEDs are used the color may correspond to the voltage level of the battery 16. Any other status can be communicated with the status indicator 40.

C. Connection of Battery Assembly to Tracker

Referring to FIGS. 14 and 15, the tracker 30 may also include a battery mount 44 for attaching the battery assembly 10 to the tracker 30. The battery mount 44 may be configured for connecting and/or securing the battery assembly 10 to the tracker body 32, 34 for the purpose of powering the electrical components of the tracker 30, such as the markers 52A, 52B, 52C, 52D. For example, as illustrated in FIGS. 14 and 15, the battery mount 44 may be disposed directly on the second surface 31B of the second body member 34, which may also be referred to as the bottom surface or underside of the of the tracker body 32, 34 of the tracker 30. As such, when secured to the battery mount 44, the battery assembly 10 extends outward from the second surface 31B of the second body member 34. This arrangement may prevent the battery assembly 10 from interfering with or intercepting the light signals emitted from the markers 52A, 52B, 52C, 52D by virtue of the markers 52A, 52B, 52C, 52D being disposed on the opposed first surface 31A. While the battery mount 44 is illustrated in the Figures as being disposed on the second surface 31B of the second body member 34, it is also contemplated that the battery mount 44 could be disposed on the first surface 31A of the first body member 32, such as if the navigation system is to observe the tracker 30 from angles not affected by the battery assembly 10.

Figure 11:
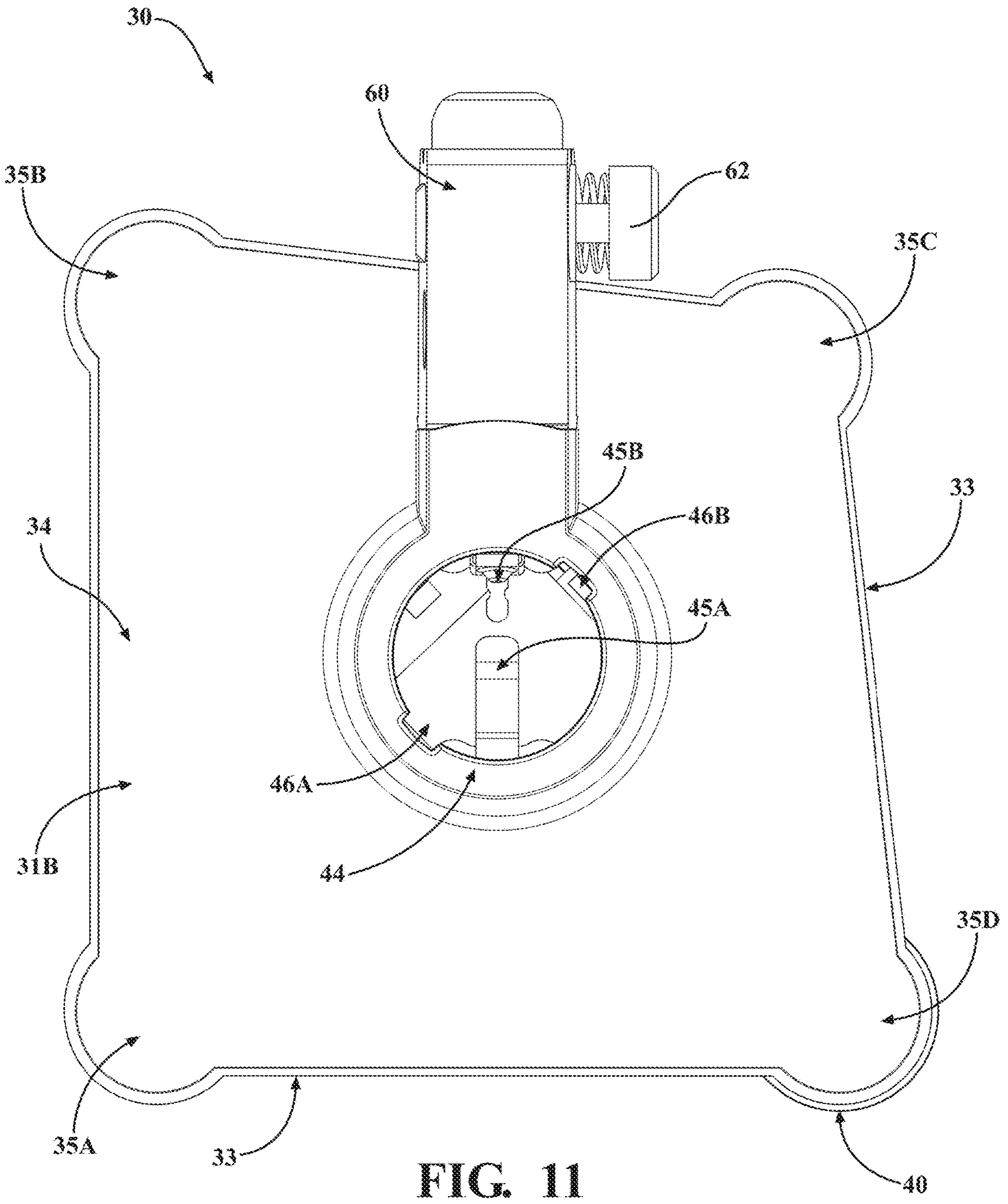
FIG. 11 is a bottom view of a of the tracker of FIG. 7, the tracker housing including a bottom portion defining a battery opening for receiving a battery assembly such as the battery assembly of FIGS. 1-6.
Figure 12:
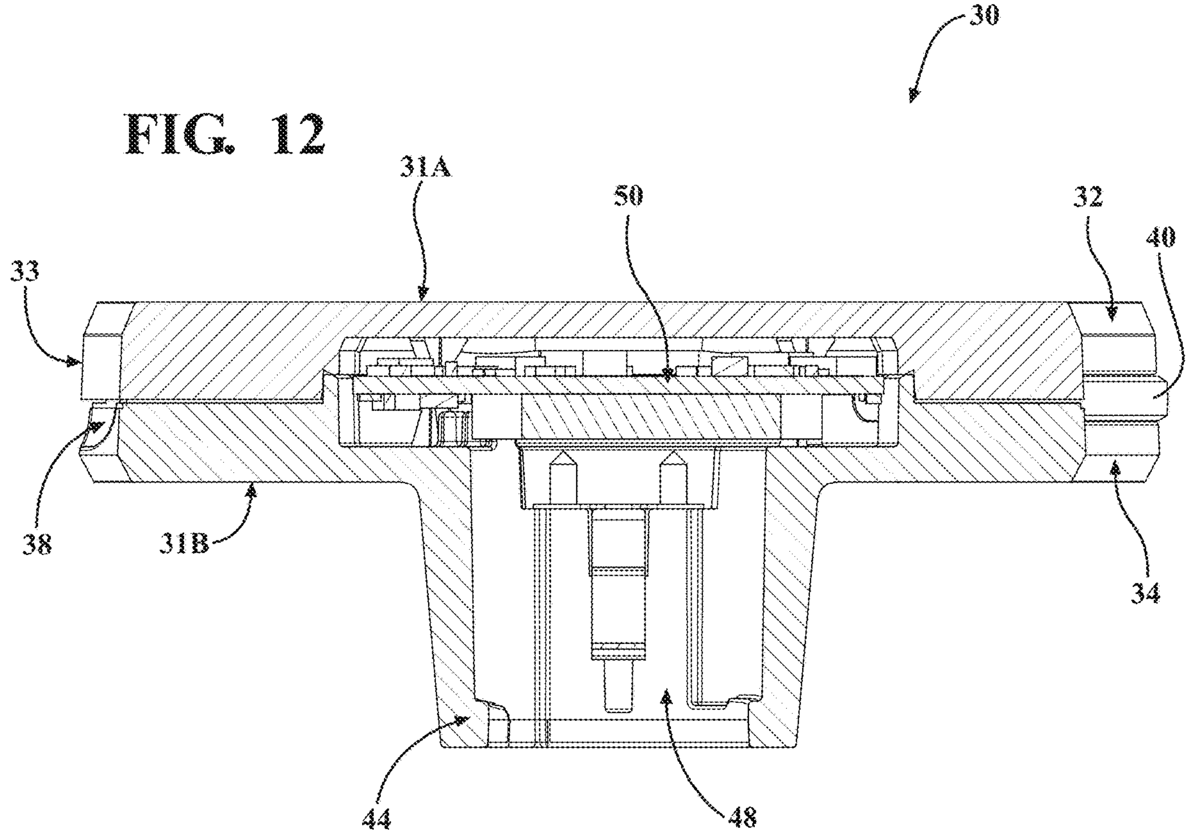
FIG. 12 is a sectional view of the tracker of FIG. 7, illustrating internal components of the tracker when assembled.

The battery mount 44 defines an opening 48. The opening 48 may be sized and configured to receive the battery assembly 10 described above. For example, the interior diameter of the opening 48 may be sized and/or shaped to receive the first portion 12 of the battery housing 12, 14. The interior surface of the opening 48 may also comprise a groove or channel 46A, 46B. For example, as illustrated in FIG. 11, the interior surface of the opening 48 defines to channels 46A, 46B positioned opposite on another. While two channels 46A, 46B are illustrated in the figures, it is contemplated that the opening 48 may be configured to define only a single channel 46A, 46B, or it may also be configured to define more than two channel 46A, 46B, 46*x*.

The channel(s) 46A, 46B may be sized and shaped to provide for removable coupling of the battery assembly 10 to the tracker 30 via the battery mount 44. For example, channel(s) 46A, 46B may be positioned within the opening 48 and configured to receive the attachment member(s) 22A, 22B, which as described above may be defined as a detent or protrusion extending from an outer surface of the first potion 12 of the battery assembly 10. The channel(s) 46A, 46B may be shaped to create an interlocking or friction fit with the attachment member(s) 22A, 22B of the battery assembly 10. For example, the channel(s) 46A, 46B may comprise a L-like shape, such that the attachment member(s) 22A, 22B of the battery assembly 10 may be slid along the channel(s) 46A, 46B as the battery assembly 10 is inserted into the opening 48 of the battery mount 44, and then be rotated or twisted once fully inserted so that the channel(s) 46A, 46B interlock with the attachment member(s) 22A, 22B of the battery assembly 10 to prevent the battery assembly from sliding out.

The battery mount 44 may further comprise two or more terminals defining electrical contacts 45A, 45B for engaging a battery 16 of the battery assembly 10 when the battery assembly 10 is seated in the battery mount 44. In particular, the electrical contacts 45A, 45B may be configured to communicate electrical energy between the battery 16 disposed in the battery mount 44 and the PCB 50, which in turn is connected to each of the markers 52A, 52B, 52C, 52D and other elements of the tracker 30 that require a power source for operation. Some implementations of LED tracking markers 52A, 52B, 52C, 52D that are powered by a battery are shown and described in U.S. Patent Application Publ. No. 2019/0321108 and International Application No. PCT/IB2020/060187, both of which are hereby incorporated by reference.

The electrical contacts 45A, 45B may be sized, shaped, and/or configured to cooperate with the vertical channels 18A, 18B and/or the lateral channel 20A, 20B of the battery assembly 10 described above. As illustrated in the Figures, the tracker 30 may comprise a first electrical contact 45A and a second electrical contact 45B. The first electrical contact 45A may be configured as a biased or spring-loaded contact configured capable of being compressed when engaged by the first battery contact 21A of the battery assembly 10. For example, as illustrated in FIGS. 11 and 16A-16D, the first electrical contact 45A may be configured as a coil spring. Alternatively, the first electrical contact 45A may also be configured as a leaf spring, coil spring or the like capable of providing a resistive force when engaged by the first battery contact 21A of the battery assembly 10 to for the purpose of maintaining contact between the first battery contact 21A and the first electrical contact 45A when the battery assembly is coupled to the tracker 30.

The second electrical contact 45A may be configured to engage with and/or interact with at least one of the vertical channel 18A, 18B and/or the lateral channel 20A, 20B. As described above, the vertical channel 18A, 18B may comprise a ramped surface, this may be configured to initiate contact with the second electrical contact 45B. As such, the second electrical contact 45B may be configured as a biased contact. In operation, as the battery assembly 10 is inserted into the opening 48 of the tracker, the ramped surface of the vertical channel 18A, 18B may initiate contact with the second electrical contact 45B. As the battery assembly 10 is inserted further into the tracker 30, the second electrical contact 45B will be compressed as it travels along the ramped surface of the vertical channel 18A, 18B. In addition to the biasing force assisting to ensure contact between the second electrical contact 45B and the battery assembly 10, the biasing force of the second electrical contact 45B can also be configured to create a friction fit between the battery assembly 10 and the tracker 30 when coupled together. The vertical channel 18A, 18B guide the second electrical contact 45B to the lateral channel 20A, 20B as the battery assembly is inserted further into the opening 48. Once inserted to max depth, the lateral channel 20A, 20B may be configured to guide the second electrical contact 45B to one of the second aperture(s) 19A, 19B of the battery housing 12, 14, and by extension, to the second battery contact 21B. For example, as the battery assembly 10 is inserted into the opening 48 of the battery mount 44 and the attachment member(s) 22A, 22B of the battery assembly 10 move along the channel(s) 46A, 46B of the battery mount to couple the battery assembly 10 to the battery mount 44, the vertical channels 18A, 18B and/or the lateral channel 20A, 20B may be configured to position and/or seat the electrical contacts 45A, 45B within the first and second aperture(s) 17, 19A, 19B of the battery housing 12 to create an electrical connection between the electrical contacts 45A, 45B of the battery mount 44 and the battery contacts 21A, 21B on the battery 16. This may be accomplished by engaging a first electrical contact 45A with a first battery contact 21A and engaging a second electrical contact 45B with a second battery contact 21B to define an electrical circuit between the battery 16 and the PCB 50, and by extension the components of the tracker 30 that require a power source for operation. The step of engaging the first electrical contact 45A with the first battery contact 21A and engaging the second electrical contact 45B with the second battery contact 21B to form an electrical circuit between the battery 16 and the PCB 50 may also serve as a selective switch for activation of the PCB 50, and more broadly the tracker 30. Forming the connection between the first electrical contact 45A and the first battery contact 21A and between the second electrical contact 45B and the second battery contact 21B may be configured to close the circuit and allow electricity to flow from the battery 16 to the components of the tracker 30. Alternatively, disengaging the first electrical contact 45A with the first battery contact 21A and engaging the second electrical contact 45B with the second battery contact 21B by removing the battery assembly 10 from the tracker 30 will open the circuit between the battery 16 and the PCB 50 causing the electrical components of the tracker 30 to be deactivated.

When the battery assembly 10 is coupled to the tracker 30, the seal 23 of the battery assembly 10 may form a hermetic seal between the battery assembly 10 and the tracker 30. This may prevent fluid and/or debris from entering the opening 48 when the battery assembly 10 is coupled to the tracker 30. Fluid or debris inside the opening 48 may interfere with the electrical connection between the battery 16 and the electrical contact(s) 45A, 45B of the tracker 30.

Figure 16A:
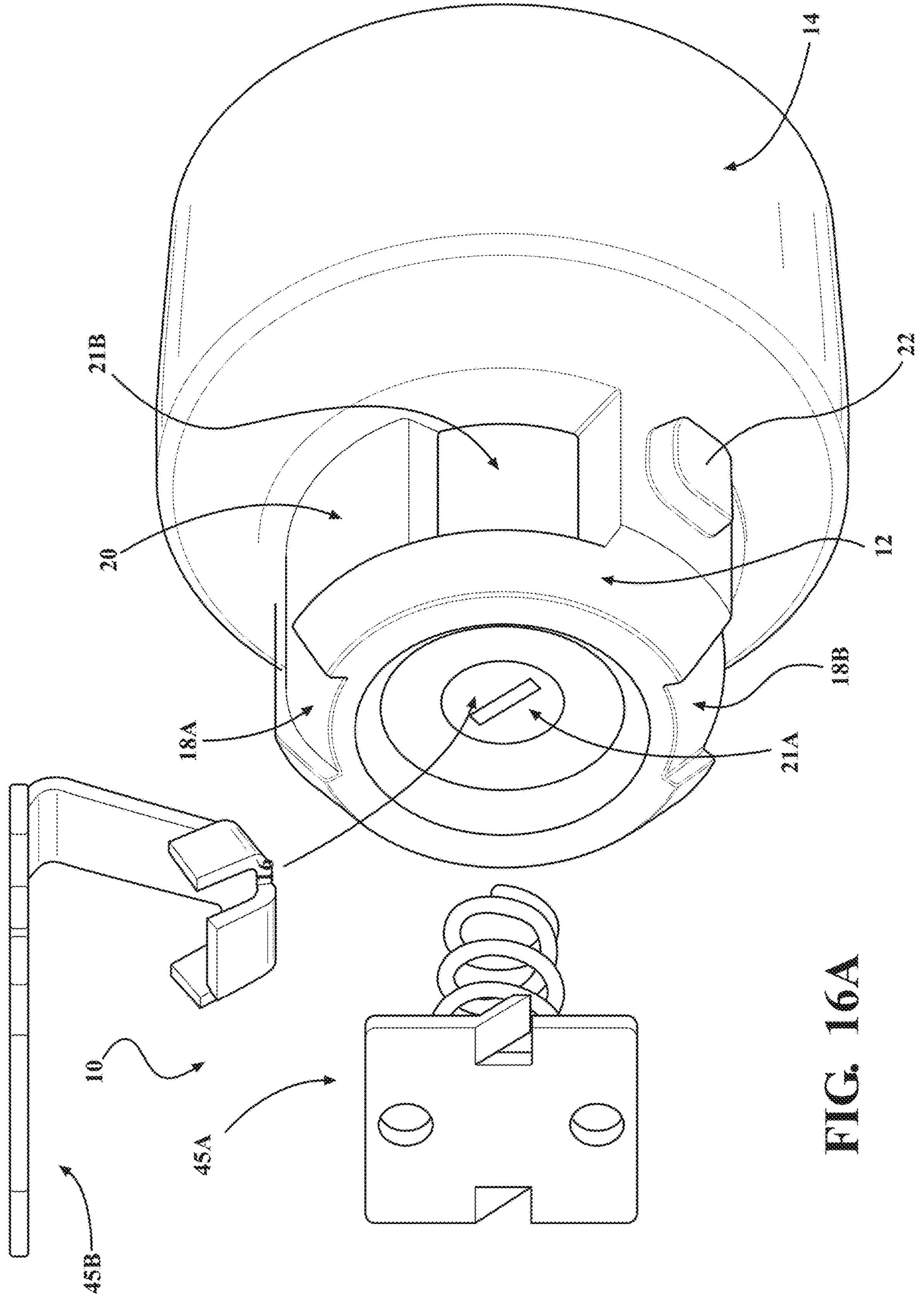
FIG. 16A is a perspective view of the battery assembly of FIGS. 1-6 and the electrical connections disposed in the battery opening of the tracker of FIGS. 7-13, illustrating the arrangement of the electrical connections of the battery opening relative to the battery assembly prior to coupling of the battery assembly to the tracker.

FIGS. 16A to 16D illustrate the stages of positioning the battery assembly 10 relative to the electrical contacts 45A, 45B of the tracker mount 40 to create an electrical connection between the electrical contacts 45A, 45B of the battery mount 44 and the battery contacts 21A, 21B on the battery 16. For simplicity in illustration, portions of the tracker mount 40 are not shown. FIG. 16A illustrates the position of the electrical contacts 45A, 45B of the battery mount 44 relative to the battery contacts 21A, 21B on the battery 16 prior to fully inserting the battery assembly 10 into the opening 48 of the battery mount 44 on the tracker 30. In this configuration, the electrical contacts 45A, 45B are fully extended (i.e. not compressed) and are separated or disengaged from the battery contacts 21A, 21B, leaving the circuit open and no power from the battery 16 to the tracker assembly 30.

Figure 16B:
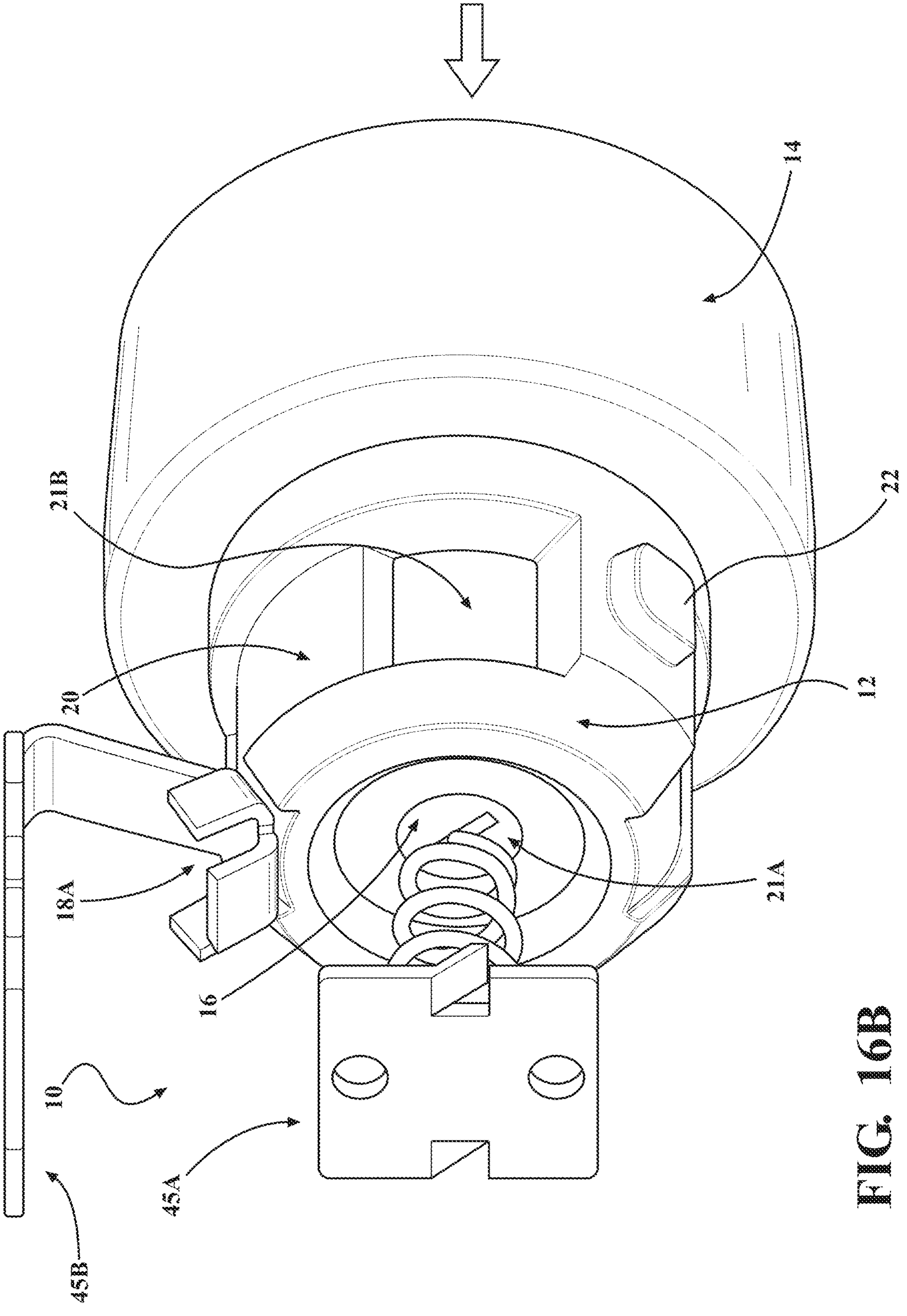
FIG. 16B is a perspective view of the battery assembly and the electrical connections disposed in the battery opening of FIG. 16A, illustrating the arrangement of the electrical connections of the battery opening relative to the battery assembly at a first stage of coupling the battery assembly to the tracker.

FIG. 16B illustrates the position of the electrical contacts 45A, 45B of the battery mount 44 relative to the battery contacts 21A, 21B on the battery 16 as the battery assembly 10 is initially being inserted into the opening 48 of the battery mount 44 on the tracker 30. The battery assembly is orientated in a first position rotationally relative to the tracker 30, such that the attachment member(s) 22A, 22B are aligned with the channel(s) 46A, 46B and the second electrical contact 45B is aligned with one of the vertical channels 18A, 18B. In this configuration, the first electrical contact 45A may or may not be engaged with the first battery contact 21A. At some point during insertion of battery assembly 10 into the opening 48, the battery 16 will contact/engage the first electrical contact 45A. Once the battery 16 engages the first electrical contact 45A, the first electrical contact will compress as the battery 16 is inserted further such that the first electrical contact will be in a partially loaded state. The second electrical contact 45B is engaged with the ramped surface at the entry or top of one of the vertical channels 18A, 18B defining in the battery housing 12, 14. The biasing force of the second electrical contact 45B may create a friction fit with the vertical channel 18A, 18B as it travels along the ramped surface, causing the second electrical contact 45B to be compressed. As illustrated in FIG. 16B, the second electrical contact 45B is still separated from the second battery contact 21B of the battery 16, leaving the circuit open and no power from the battery 16 to the tracker assembly 30.

Figure 16C:
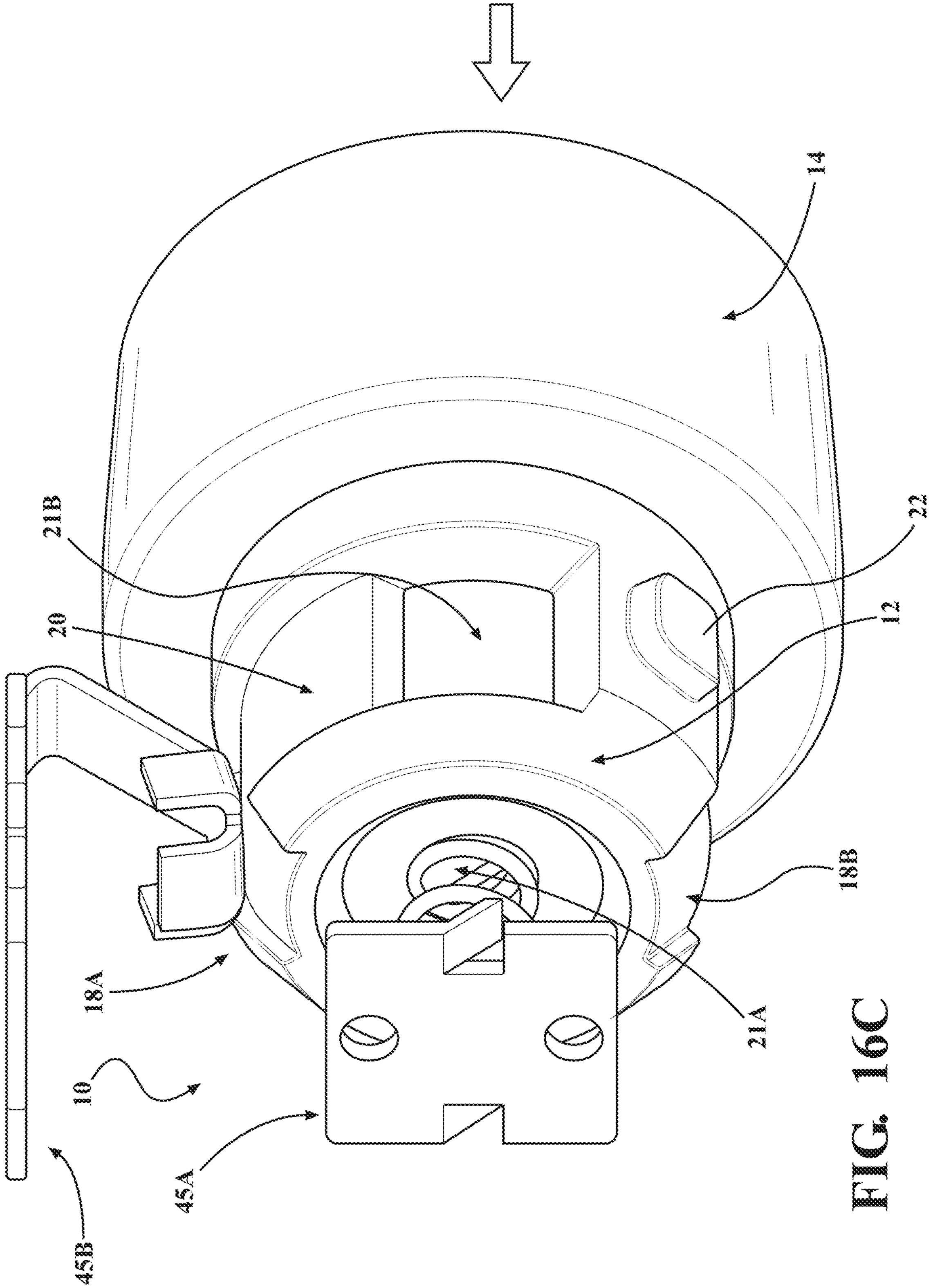
FIG. 16C is a perspective view of the battery assembly and the electrical connections disposed in the battery opening of FIG. 16A, illustrating the arrangement of the electrical connections of the battery opening relative to the battery assembly at a second stage of coupling the battery assembly to the tracker.

FIG. 16C illustrates the position of the electrical contacts 45A, 45B of the battery mount 44 relative to the battery contacts 21A, 21B on the battery 16 as the battery assembly 10 is fully inserted into the opening 48 of the battery mount 44 on the tracker 30. The battery assembly 10 is still orientated in the first position rotationally relative to the tracker 30, with the second electrical contact 45B is aligned with one of the vertical channels 18A, 18B. In this configuration, the first electrical contact 45A is engaged with the first battery contact 21A and compressed. The second electrical contact 45B is engaged with the bottom of one of the vertical channels 18 but is still separated from the second battery contact 21B of the battery, leaving the circuit open and no power from the battery 16 to the tracker assembly 30. The second electrical contact 45B compressed such that it is applying a force to the battery assembly 10. When the second electrical contact 45B is positioned at the bottom of the vertical channels 18, the second electrical contact 45B is in position to transition to the lateral channel 20A, 20B defined in the battery housing 12, 14. At this point, battery assembly 10 is seated within the opening of the tracker 30 and the seal 23 of the battery assembly 10 is engaged with the tracker 30. The attachment member(s) 22A, 22B engaged with the channel(s) 46A, 46B and/or the second electrical contact 45B engaged with the vertical channel 18A, 18B may secure the battery assembly 10 within the opening 48 of the tracker. One advantage of this is that the battery assembly 10 may be coupled to the tracker 30 without activating the tracker 30 and/or draining the battery 16 until the tracker 30 is needed.

Figure 16D:
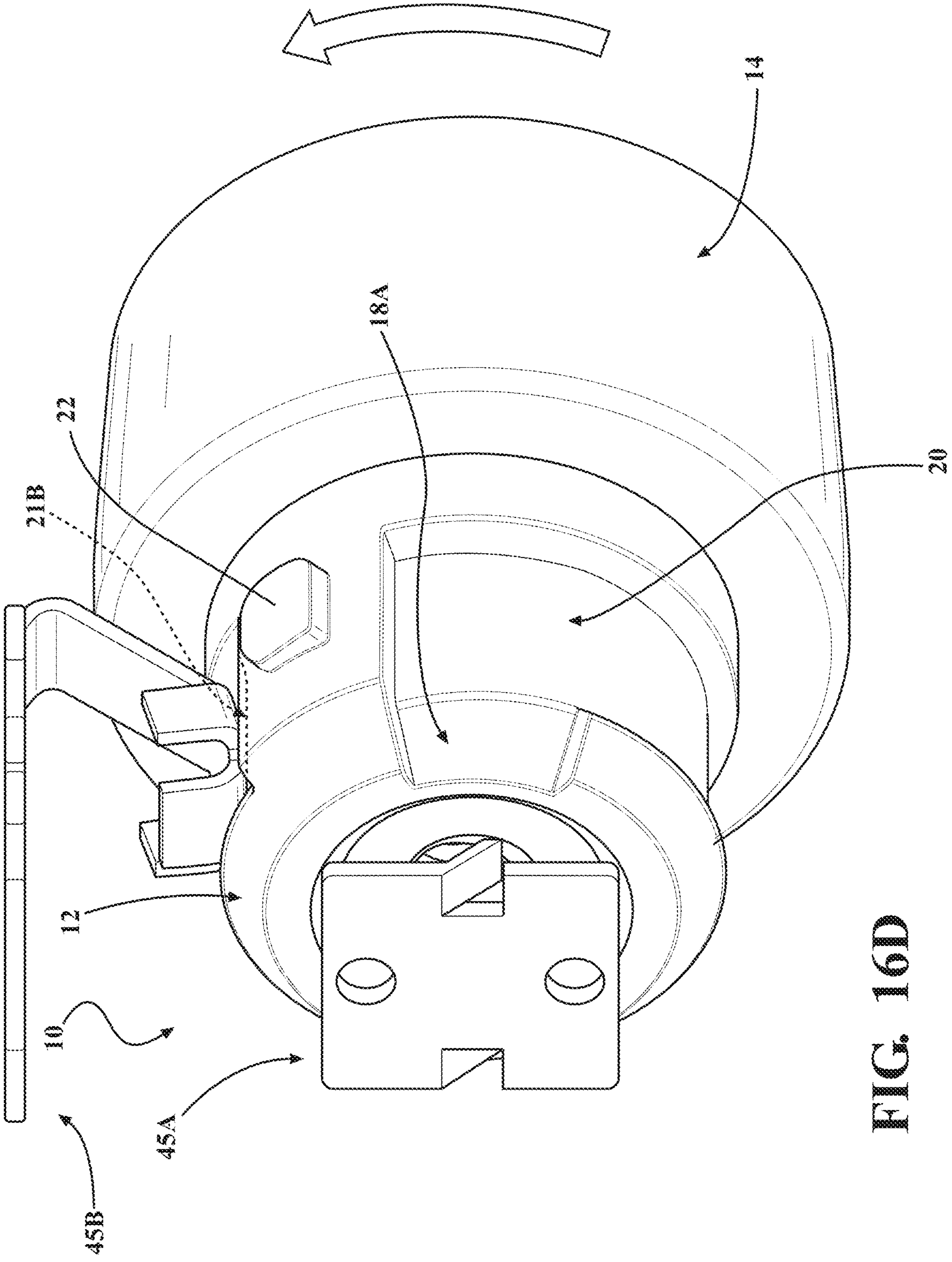
FIG. 16D is a perspective view of the battery assembly and the electrical connections disposed in the battery opening of FIG. 16A, illustrating the arrangement of the electrical connections of the battery opening relative to the battery assembly at a final stage of coupling the battery assembly to the tracker where the battery assembly is coupled to the tracker creating an electrical connection with the circuit board and activating the tracker.

FIG. 16D illustrates the position of the electrical contacts 45A, 45B of the battery mount 44 relative to the battery contacts 21A, 21B on the battery 16 as the battery assembly 10 is fully inserted into the opening 48 and is rotated to a second position rotationally relative to the tracker 30. Rotating the battery housing 12, 14 clockwise relative to the tracker 30 transitions the battery assembly 10 from the first position to the second position rotationally relative to the tracker 30. This causes the second battery contact 21B to move through the lateral channel 20A, 20B defined in the battery housing 12, 14. When fully inserted and rotated to the second position relative to the tracker, the first electrical contact 45A remains engaged with the first battery contact 21A and the second electrical contact 45B is now positioned to engage the second battery contact 21B of the battery 16. In this configuration, the circuit is closed allowing power from the battery 16 to flow to the components of the tracker assembly 30 requiring power for operation. At this point, the tracker assembly 1, including the tracker 30 and battery assembly 10, is activated. The process described above may be completed in reverse to remove the battery assembly 10 from the tracker 30 to deactivate the tracker assembly 1. In other words, the battery assembly 10 can be rotated counter-clockwise from the second position to the first position to deactivate the tracker assembly 1. The battery assembly 10 can remain securely coupled to the tracker mount 40 even while in the first position. In this way, the battery assembly 10 can act as both a power source and a rotatable selective switch. This may allow the user to avoid unnecessarily draining the battery 16 when the tracker 30 is not being used, as the tracker 30 is not activated and/or the power is not drawn from the battery 16 until the battery assembly 10 has been rotated from the first position to the second position.

It is also contemplated that the battery assembly 10, such as the housing 12, 14 may comprises indicia and symbols configured to identify the battery 16, batter assembly 10, or the like. The indicia may comprise text, visual identifiers, color coding, bar codes, or the like. The indicia may be etched into the housing 12, 14, provided on a sticker, or mounted to the housing 12, 14 in a similar fashion. For example, the housing 12, 14, such as the exposed surface of the second portion 14, may include indicia that identifies the size and/or power of the battery 16 disposed in the battery housing 12, 14. This may help the user in identifying which trackers 30 the battery 16 is capable of powering. The housing 12, 14 may also include indicia identify the size and/or shape of the housing 12, 14 to identify which trackers 30 the battery assembly 30 is compatible with. For example, there may be a plurality of different sized trackers 30, and the indicia may identify which tracker 30 the battery assembly 10 will couple to. The indicia may also comprise text or symbols illustrating the method of coupling and/or removing the battery assembly 10 from the tracker 30. For example, housing 12, 14 may comprise a curved line with arrows at the opposing ends of the line. The first arrow indicating the rotational direction to move the battery assembly 10 to the first position (i.e., OFF) and the second arrow indicating the rotational direction to move the battery assembly 10 to the second position (i.e. ON). This may also include illustrating the method of removing the battery 16 from the housing 12, 14.

The tracker body 32, 34 may similarly comprise textual or graphical indicia. The indicia may be etched into the surface, protruding from the surface, or printed on the surface of the tracker body 32, 34. The indicia may illustrate the method of coupling and/or removing the battery assembly 10 from the tracker 30. For example, the indicia on the tracker body 32, 34 may denote the first and second positions (ON or OFF) for the battery assembly 10. This could include a pair of arrows or marks spaced radially about the opening on the tracker body 34 that corresponds to a similar indicium on the battery assembly 10. The first arrow identifying the first position and the second arrow identifying the second position. When the corresponding marking on the battery assembly 10 is positioned adjacent the first arrow, the battery assembly 10 is in the first position (i.e., OFF). Alternatively, when the corresponding marking on the battery assembly 10 is positioned adjacent the second arrow, the battery assembly 10 is in the second position (i.e., ON).

The battery assembly 10 being separable from the tracker 30 allows for the battery 16 to be replaced and/or recharged. For example, following a medical procedure, the battery assembly 10 may be removed from the battery opening 48, and replaced with a new battery 16. The battery assembly 10 with the new battery 16 may then be re-installed in the opening 48 of the tracker 30 as described above to activate the tracker assembly 1. Alternatively, the battery assembly 10 may be removed from the battery opening 48 of the tracker 30 and a second battery assembly 10 may then be installed in the opening 48 of the tracker 30 in the same manner described above. The removed battery assembly 10 may optionally be discarded, disposed of, or reprocessed. Reprocessing may include replacing the battery 16 of the battery assembly 10. Attentively, reprocessing may include recharging the battery 16 of the battery assembly 10.

As described above, the tracker 30 may comprise one or more active markers 52A, 52B, 52C, 52D disposed on the PCB 50 and driven by the PCB 50 of the tracker 30. The control circuit of the PCB 50 (or coupled to the PCB) may be coupled to the battery assembly 16 to power the markers 52A, 52B, 52C, 52D through the PCB 50. The PCB 50 may be configured to control any operating parameters of the light emitted from the markers 52A, 52B, 52C, 52D, such as by regulating the current, voltage or power supplied to the markers 52A, 52B, 52C, 52D from the battery 16. These operating parameters can include transmission power, intensity, firing sequence, wavelength, or the like.

D. Tracker Mount

Figure 17A:
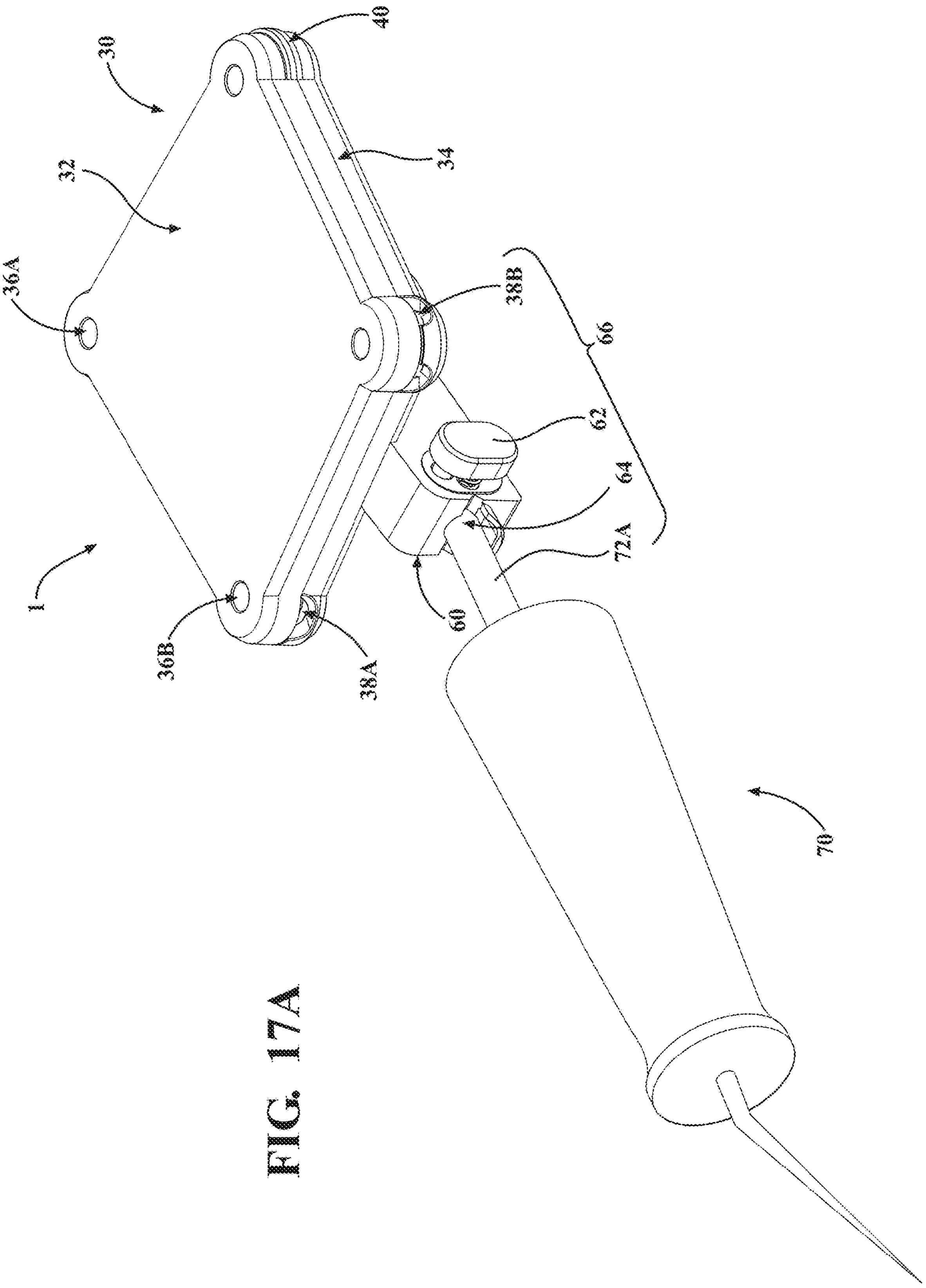
FIG. 17A is a perspective view of the tracker of FIGS. 7-13 coupled to a surgical instrument, illustrating one implementation for removably coupling a tracker mount of the tracker to a key on the surgical instrument.
Figure 17B:
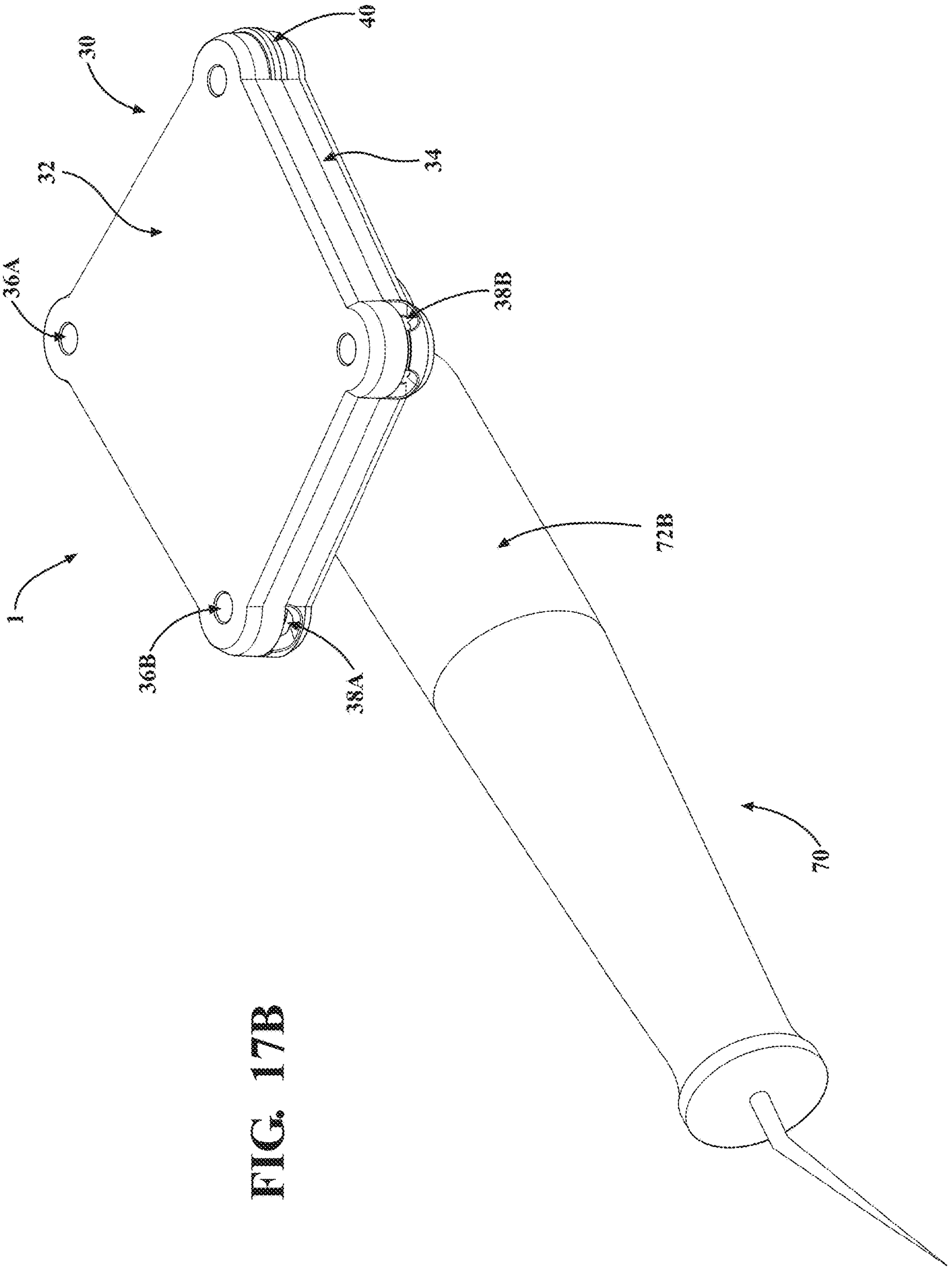
FIG. 17B is a perspective view of the tracker of FIGS. 7-13 coupled to a surgical instrument, illustrating one implementation for coupling the tracker directly to a base or housing of the surgical instrument.

Referring to FIGS. 17A and 17B, the tracker 30 may further comprise a tracker mount 60 for removably coupling the tracker assembly 1, including the tracker 30 and/or battery assembly 10, to the surgical object or instrument. The tracker mount 60 may comprise a preloading mechanism 62, such as a button or biased member, to secure the surgical instrument 70 to the tracker mount. The instrument may include a key 64, with the tracker mount 60 being configured to receive the key 64, and the preloading mechanism 62 configured to engage the key 64 to removably secure the key 64 to the tracker mount.

In FIG. 17A, the surgical tracker 30 and/or surgical tracker assembly 1 is illustrated as being coupled to a surgical instrument 70, according to one implementation. For illustrative purposes, generically-depicted surgical instruments 70 configured for hand-held use are shown in FIGS. 17A and 17B, such as a pointer. However, it is further contemplated that the surgical tracker 30 and/or surgical tracker assembly 1 may be used with any suitable type of surgical instrument 70 without departing from the scope of the present disclosure. For example, the surgical tracker assembly 1 may be coupled to a robotic arm, a surgical saw, a drill, to a patient, etc. As illustrated in FIG. 17A, the surgical instrument 70 includes a tracker coupling member 72A. The tracker coupling member 72A may be referred to as key 64 and configured for removably coupling with the tracker mount 60 of the surgical tracker assembly 1, which will be described in greater detail below.

It is further contemplated that the surgical tracker assembly 1 and the surgical instrument 70 may be constructed as a unitary device, where a portion of the surgical instrument 70 forms a tracker coupling member 72B and the surgical tracker assembly 1 is disposed on the tracker coupling member 72B. For example, the tracker coupling member 72B may be unitary formed with the first body member 32 or the second body member 34 of the tracker body 32, 34. Alternatively, the tracker coupling member 72B may be coupled to the tracker body 32, 34 by a weld, adhesive, epoxy, or similar coupling means.

In addition to hand-held surgical instruments 70 of various types and configurations, aspects of the tracker assembly 1 may also be employed in connection with surgical instruments 70 that may be controlled, guided, positioned, or otherwise manipulated with one or more types of surgical robots. Certain types of surgical robots are disclosed in U.S. Pat. No. 9,119,655, entitled "Surgical Robotic arm Capable of Controlling a Surgical Instrument in Multiple Modes;" U.S. Pat. No. 10,456,207, entitled "Systems and Tools for use with Surgical Robotic Manipulators;" U.S. Patent Application Publication No. 2019/0231447, entitled "End Effectors And Methods For Driving Tools Guided By Surgical Robotic Systems;" U.S. Patent Application Publication No. 2016/0302871, entitled "Integrated Medical Imaging and Surgical Robotic System;" and U.S. Patent Application Publication No. 2020/0078097, entitled "Methods and Systems for Robot-Assisted Surgery," the disclosures of each of which are hereby incorporated by reference in their entirety.

Figure 18:
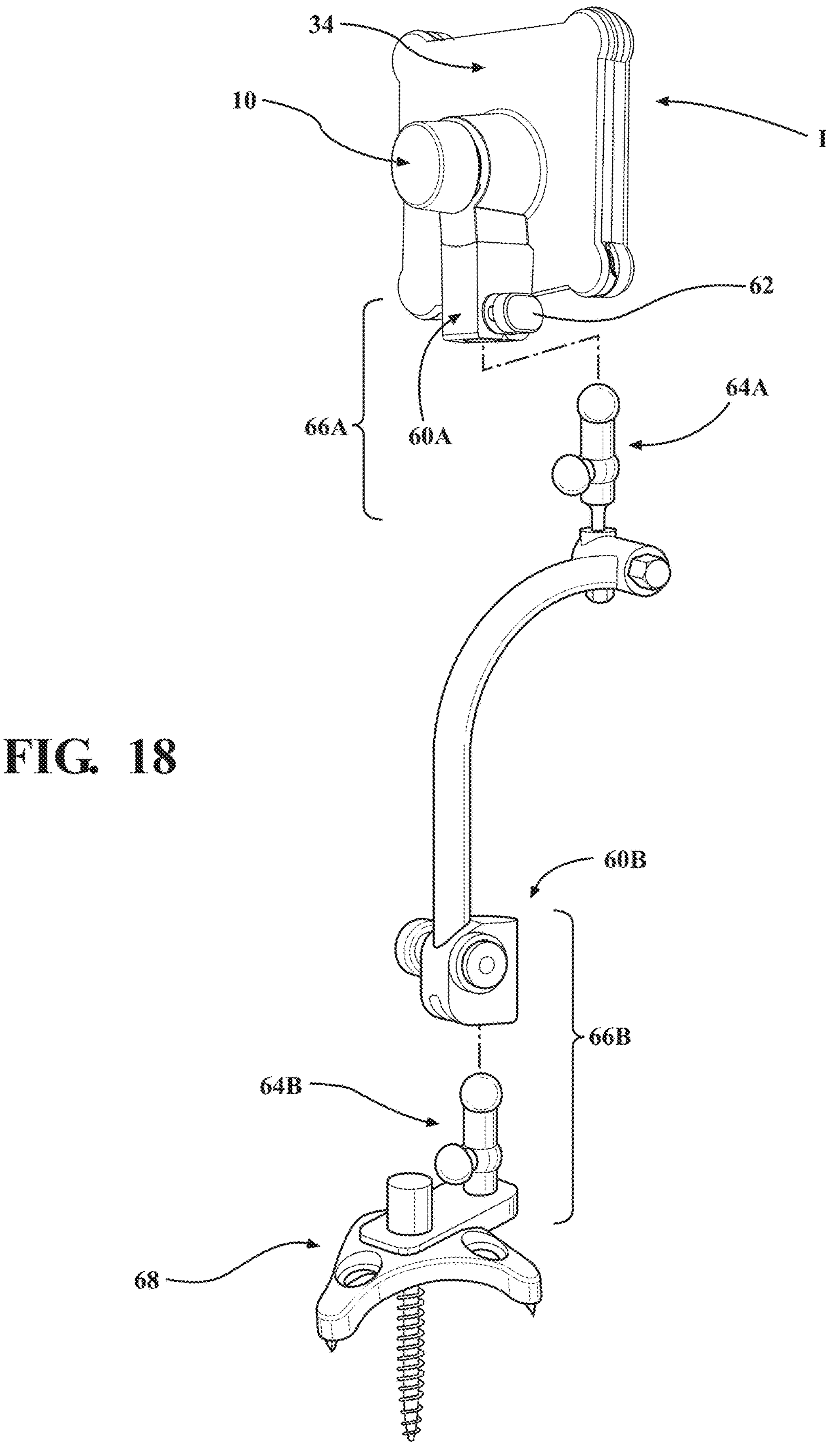
FIG. 18 is a perspective view of the tracker of FIGS. 7-13 coupled to a connector assembly including a key for attaching the tracker to the connector assembly.

It is further contemplated that the aspects of the tracker assembly 1 may also be employed in connection with a connector assembly 66, an implementation of a connector assembly 66A, 66B including a key 64 for removable attaching a tracker assembly 1 is described in U.S. Pat. No. 10,537,395, entitled "Navigation tracker with kinematic connector assembly;" which is hereby incorporated by reference in its entirety. Referring to FIG. 18, an implementation of the connector assembly 66A, 66B may comprise a preloading mechanism 62 to secure the key 64 in the tracker mount 60. The preloading mechanism 62 is configured to urge the key 64 into engagement with the tracker mount 60 such that the key 64 is kinematically constrained to the tracker mount 60 by the six points of contact. As illustrated in one implementation in FIG. 18, the connector assembly 66A, 66B may be used to couple the tracker 30 to an extension arm in the same relative position throughout the surgical procedure. The connector assembly 66A, 66B allows the tracker 30 to be disconnected from and repeatably connected to either the extension arm or directly to a bone plate 68 without requiring the navigation system to be recalibrated and/or the tracker assembly 1 to be re-registered to the object. Likewise, the tracker 30 and the extension arm could be disconnected from and repeatably connected to the bone plate 68 as a unit without requiring the navigation system to be recalibrated or the tracker assembly 1 to be re-registered to the object. At least one connector assembly 66A, 66B may be used to couple the tracker 30 and/or the bone plate 68 to opposite ends of the extension arm. The bone plate 68 may then be coupled to the patient, bone, or other object to be tracked by the navigation system.

In the configuration shown in FIG. 18, the tracker 30 is coupled to a first end of the extension arm using a first connector assembly 66A. The bone plate 68 is coupled to a second end of the extension arm through a second connector assembly 66B. It should be appreciated that the second connector assembly 66B is generally the same as the first connector assembly 66A such that components from the first connector assembly 66A are interchangeable with components from the second connector assembly 66B. For example, the tracker 30 may be coupled directly to the bone plate 68 such that the assembly only comprises one connector assembly 66A, 66B.

The tracker assembly 1, tracker 30, and/or the tracker mount 72 may be further comprise textual or graphical indica. The indicia may include arrows, text, or other similar markings. The indicia may be configured to assist the user in coupling and/or detaching the tracker 30 from the tracker mount and/or the connector assembly 66A, 66B. this may include markings to assist with alignment, provide directional indicators, or the like. For example, the tracker assembly 1 and the tracker mount 72 may include markings indicating how to align the tracker assembly 1 relative to the tracker mount 72.

E. Printed Circuit Board Implementations

Referring to FIGS. 19 to 23, various additional implementations and/or configurations of the Printed Circuit Board (PCB) 50, 150 are described.

Figure 19:
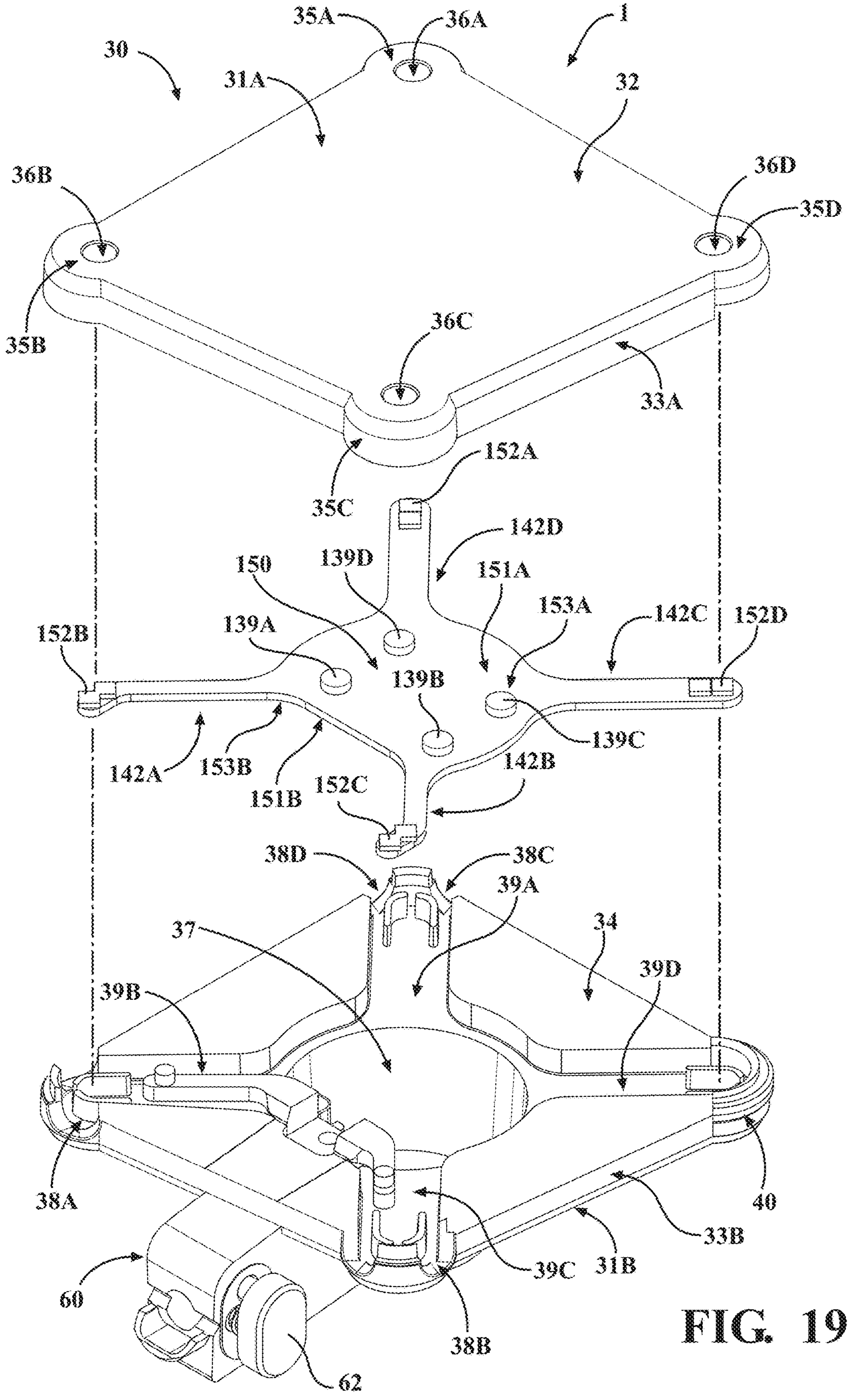
FIG. 19 is a partially exploded view of a configuration of a tracker, the tracker including a housing having top and bottom portions and a printed circuit board arranged to be disposed between the top and bottom portions of the housing.

Referring to FIG. 19 a sterilizable surgical device 1, such as a surgical tracker 30 and/or surgical tracker assembly 1, is illustrated. In the example configuration shown in FIG. 19, the sterilizable surgical tracker 30 may include all of the same features and provide all of the same functionality as the tracker assembly shown FIGS. 13 to 18 and described above. For example, as illustrated in FIG. 19, the tracker 30 may comprise a tracker body 32, 34 formed from a first body member 32 and a second body member 34. The tracker body 32, 24 includes a first surface 31A, an opposed second surface 31B, and a plurality of side surfaces 33 connecting between the first and second surfaces 31A, 31B.

The first body member 32 and second body member 34 may be formed from a material that is not susceptible to damage when exposed to a sterilant or repeatedly subjected to a sterilization process. It is also contemplated that the first body member 32 and the second body member 34 may be formed from a plastic or similar polymeric material, steel, carbon, titanium, or similar material. It is further contemplated that the first body member 32 and the second body member 34 may be formed from any rigid or generally rigid material, then coated with a conformal coating to one or more of the outer surfaces of the first body member 32 and the second body member 34, with the conformal coating configured to protect the first body member 32 and the second body member 34 from being damaged when subjected to sterilization process such as autoclaving. The conformal coating applied to the surface(s) of that the first body member 32 and the second body member 34 may comprise one or more of the following: an epoxy, a polyurethane, parylene or a parylene polymer, a silicone, an acrylic, or a similar protective coating. The coating may also be referred to as a film, film-coating, or film-like layer. In example, a parylene coating may be applied and/or disposed over the first body member 32 and/or the second body member 34 to protect first body member 32 and the second body member 34 from damage when undergoing a sterilization process. While a surgical tracker 30 is shown as one example configuration of a sterilizable surgical device 1 to which a conformal coating, such as a parylene, may be applied, it should be understood that is if further contemplated that the conformal coating may also be applied to other sterilizable surgical devices 1 to protect the device during a sterilization process. Some examples of a sterilizable surgical device 1 may include a drill, surgical handpiece, saw, driver, saw blade, tracker mount, surgical instrument, surgical instrument tip or bit, surgical helmet, headpiece, or similar sterilizable device.

As described above, the tracker body 32, 34 may comprise any shape, such as a square, rectangle, x-shape, circle, or the like. As illustrated in the figures, the tracker body 32, 34 may be configured in a generally square shape, with an arm 35A, 35B, 35C, 35D extending outward from the tracker body 32, 34. Each of the of the arms 35A, 35B, 35C, 35D may be configured to define an aperture 36A, 36B, 36C, 36D. While not required, each of the apertures 36A, 36B, 36C, 36D may be covered by a window or similar coating that allows for light to pass through and/or be visualized through the aperture 36A, 36B, 36C, 36D.

As shown in FIG. 19, a chamber 37 is defined between the first and second surface 31A, 31B of the first body member 32 and the second body member 34. The first body member 32 and/or the second body member 34 may further define one or more channels 39A, 39B, 39C, 39D that extend outward form the chamber 37. The one or more channels 39A, 39B, 39C, 39D may extend outward from the chamber 37 toward one of the exterior surfaces 31A, 31B of the tracker body 32, 34. While not shown in the figures, it is further contemplated that the channel 39A, 39B, 39C, 39D may extend outward from the chamber 37 and extend through either of the first or second surface 31A, 31B of the tracker body 32, 34.

The exterior surfaces 31A, 31B of the tracker body 32, 34 may further define one or more openings 38, each of the one or more openings in fluid communication with the one of the one or more channels 39A, 39B, 39C, 39D. The openings 38 in conjunction with the channels 39A, 39B, 39C, 39D form a pathway to/from and through the chamber 37 of the tracker body 32, 34 to allow sterilant to enter/exit through the chamber 37. The channels 39A, 39B, 39C, 39D and opening (s) 38 also serve as a drain for any debris, sterilant, or the like that may enter the channel 39A, 39B, 39C, 39D and/or chamber 37 to drain from the tracker body 32, 34. While the example configuration of the tracker body 32, 34 illustrated in the figures defines two openings 38 in each arm of the second body member 34, it is contemplated that one a single opening 38 may be defined in each arm of the second body member 34. Alternatively, it is also contemplated that opening 38 may be formed in the first body member 32 of the tracker body 32, 34 and in fluid communication with the one of the one or more channels 39A, 39B, 39C, 39D to form a pathway to/from and through the chamber 37 of the tracker body 32, 34 to allow sterilant to enter/exit through the chamber 37.

The tracker 30 may further comprise a printed circuit board (PCB) 50, 150. The printed circuit may comprise all of the same features and/or functionality as the PCB 50 described. As such, components of the PCB 150 illustrated in FIGS. 19 to 23B should be understood to have at least the same features and/or functionality as the PCB 50 described above with the same base number (last two digits of the reference number). For example, the markers 152A, 152B, 152C, 152D illustrated in FIGS. 19 to 23B have the same features and functionality as the markers 52A, 52B, 52C, 52D described.

The PCB 150 may be shaped to correspond to the shape of the chamber 37 and channels 39A, 39B, 39C, 39D defined by the tracker body 32, 34. For instance, assuming the chamber 37 and channels 39A, 39B, 39C, 39D defined by the tracker body 32, 34 are arranged in an X-shape, the PCB 150 may be configured to have a shape conforming to the X-shape (e.g., including leg portions 142A, 142B, 142C, 142D corresponding to the channels 39A, 39B, 39C, 39D formed in the tracker body 32, 34). The PCB 150 may include a central portion and a plurality of leg portions 142A, 142B, 142C, 142D that extend from the central portion of the PCB 150. While the tracker 30 is illustrated in the figures as having a generally X-shaped PCB 150, it is contemplated that the PCB 150 may be formed in any number of suitable shapes, such as a square, rectangle, disk, triangle, plate, circle, sphere, trapezoid cube, or the like that correspond to and/or fit within the shape of the chamber 37 and channels 39A, 39B, 39C, 39D defined by the tracker body 32, 34.

Figure 20:
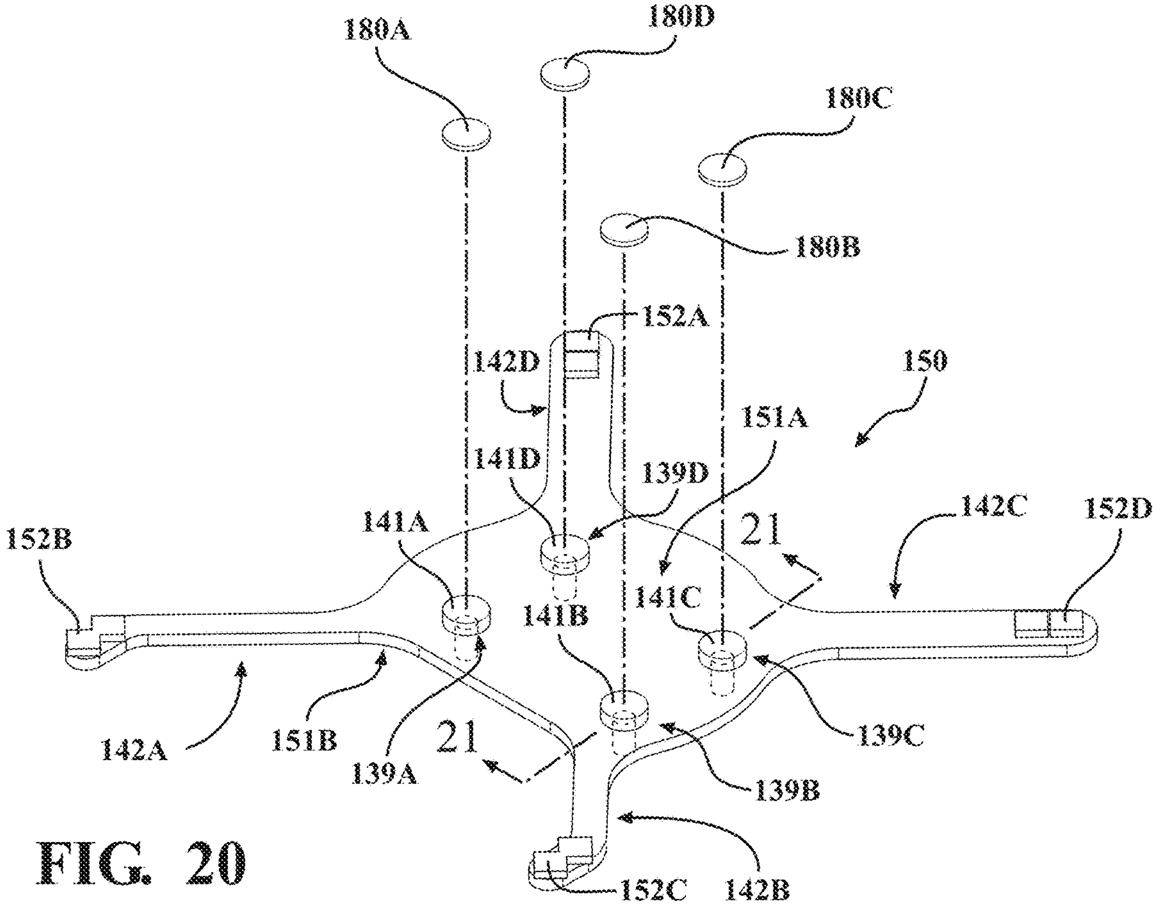
FIG. 20 is a perspective of a first configuration of a printed circuit board, the printed circuit board including via-in-pad arrangements for connecting an electronic or electrical component to traces disposed between the outer surfaces of the printed circuit board.
Figure 21A:
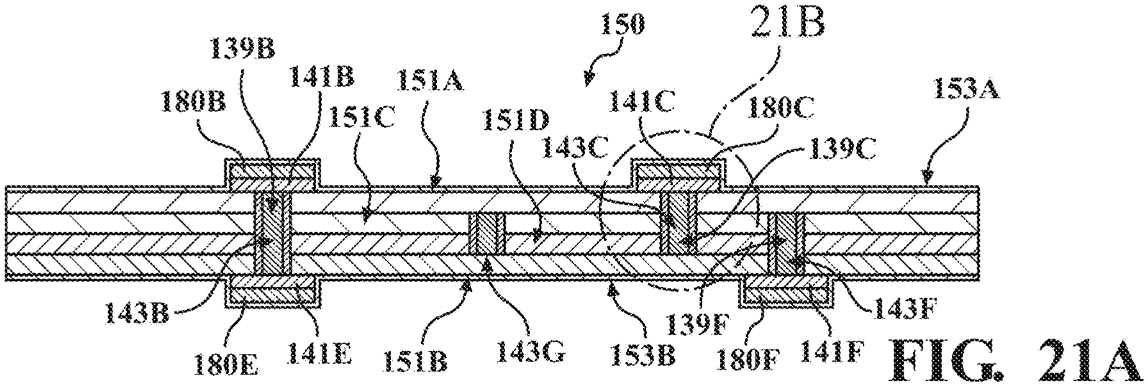
FIG. 21A is a sectional view of the printed circuit board of FIG. 20 illustrating various via-in-pad arrangements of the printed circuit board for defining connections between the electronic or electrical components to the traces disposed between the outer surfaces of the printed circuit board.
Figure 21B:
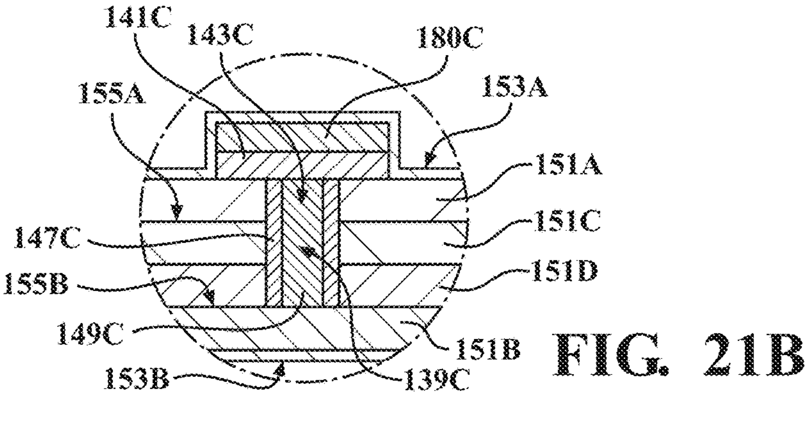
FIG. 21B is an enhanced section view of a via-in-pad arrangement of the printed circuit board of FIG. 21A.
Figure 21C:
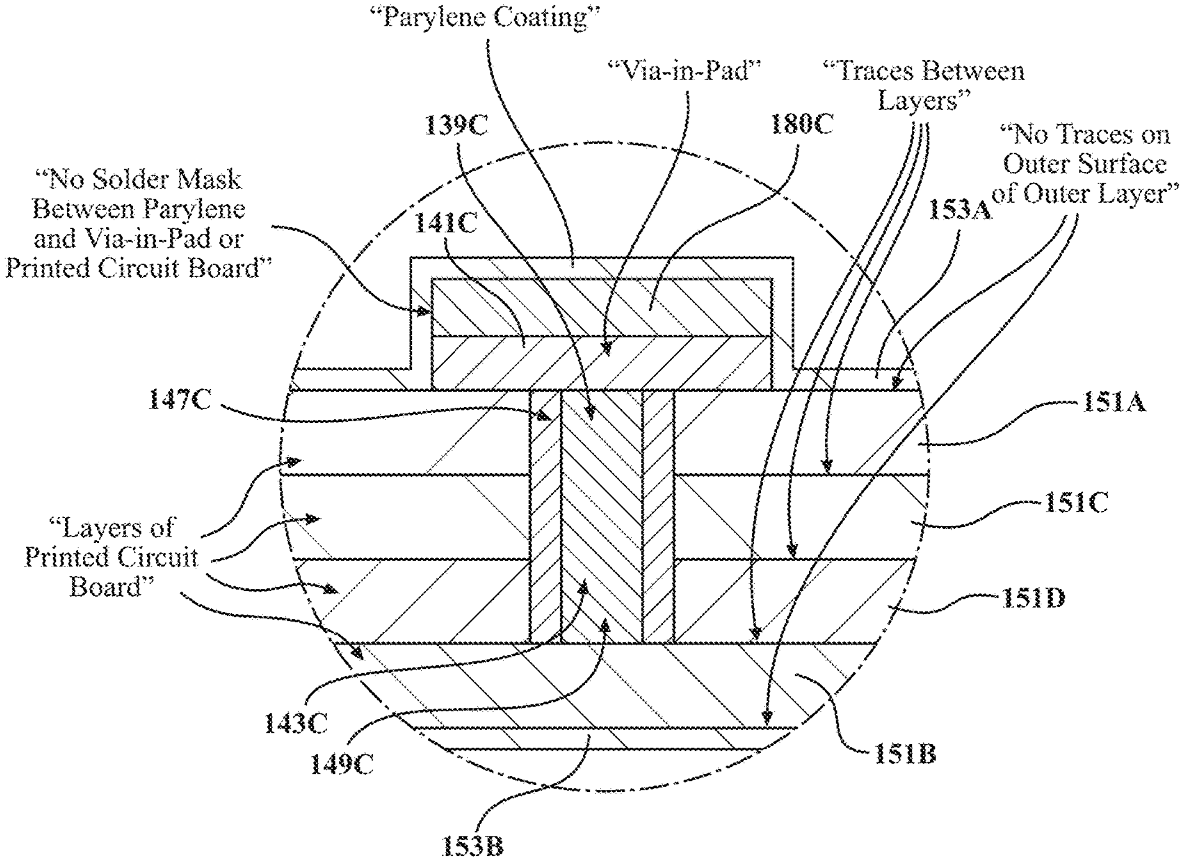
FIG. 21C is a further enhanced section view of a via-in-pad arrangement of the printed circuit board of FIG. 21A.
Figure 21D:
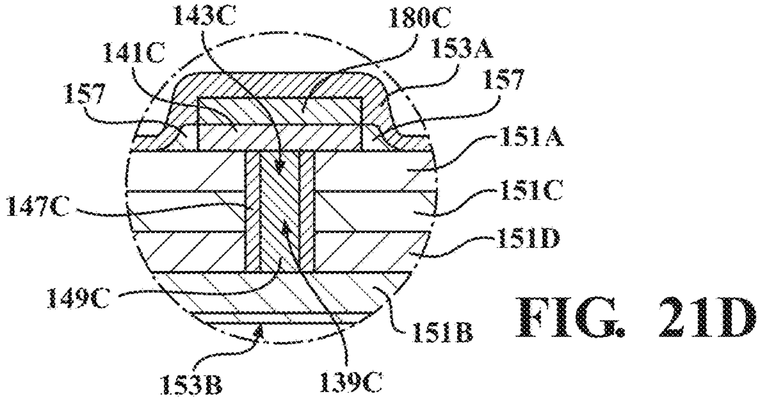
FIG. 21D is an enhanced section view of an alternate configuration of a via-in-pad arrangement of the printed circuit board of FIG. 21A.
Figure 23A:
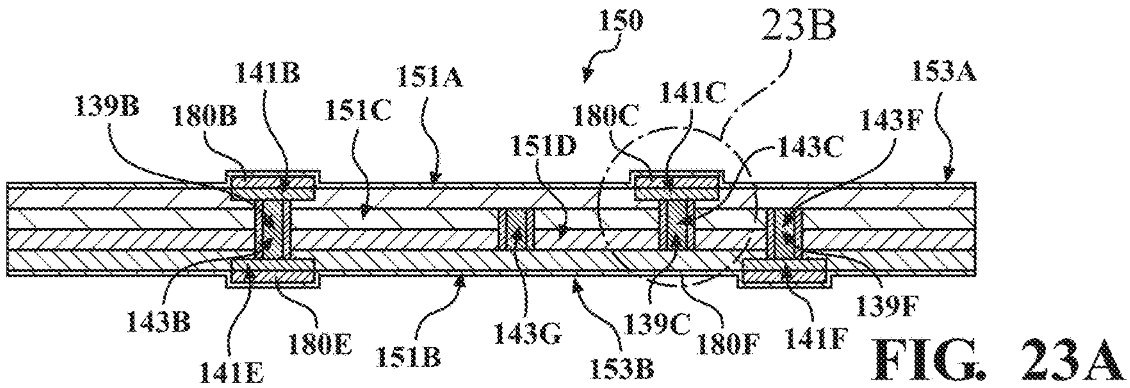
FIG. 23A is a sectional view of the printed circuit board of FIG. 22 illustrating various via-in-pad arrangements of the printed circuit board for defining connections between the electronic or electrical components to the traces disposed between the outer surfaces of the printed circuit board.

Referring to FIGS. 20 to 21D, the PCB 150 may be formed from one or more layers 151 that form the base or body of the PCB 150. The layers 151 may be stacked on top of one another, layered, positioned adjacent one another, or arranged in a similar relationship to one another. Referring to FIGS. 21A and 23A, an example configuration of the PCB may comprise a four layers 151A, 151B, 151C, 151D, including two outer layers 151A, 151B and two inner layers 151C, 151D, with the two inner layers 151C, 151D disposed or sandwiched between the two outer layers 151A, 151B in a stacked configuration. While the example configuration of the PCB 150 is illustrated as having two (2) inner layers 151C, 151D disposed between two outer layers 151A, 151B, it is contemplated that the PCB 150 may comprise any number of inner layers 151C, 151D, for example a PCB 150 may comprise three (3), four (4), five (5) or more inner layers 151C, 151D disposed between two outer layers 151A, 151B.

Similar to as described above, the PCB 150 may include traces, also known as circuit trace(s). Traces are generally conductive tracks of a printed circuit board that connect components electrically and allows electric current to flow with little resistance. For example, as described above, the trace(s) of the PCB 150 may be arranged on the PCB 150 and configured to connect the markers 152A, 152B, 152C, 152D, a control circuit (not shown), and electrical connector 45 for forming an electrical connection with the battery 16. The trace(s) may also be arranged and configured to form electrical connections between one or more electronic or electrical components 180 of the PCB 150. In the configurations of the PCB 150 illustrated in FIGS. 19 to 23B, there are no trace(s) disposed on an exterior surface of the PCB 150. For example, there are no trace disposed on the outer surface of either of the outer layers 151A, 151B. All traces are disposed between the outer surface of the opposed outer layers 151A, 151B. For example, traces may be disposed on any of the inner layers 151C, 151D. It is further considered that traces may be disposed on the inner surface of the outer layers 151A, 151B, e.g. where the outer layers 151A, 151B abuts one of the inner layers 151C, 151D. By removing the traces from the outer surface(s) of the PCB 150, the traces may be further protected from being damaged during use, exposure, and/or cleaning, such as when the PCB 150 is subjected to a sterilization process.

The PCB 150 may further comprise one or more via-in-pad 139 arrangements in/on the PCB 150. The via-in-pad 139, may include an aperture or hole 143 defined in one or more layers 151A, 151B, 151C, 151D of the PCB 150. For example, as illustrated in FIGS. 21A and 23A, a via-in-pad 139B may include a hole 143B defined by and extending through each of the layers 151A, 151B, 151C, 151D of the PCB 150. In another example, a via-in pad 139C may include a hole 143C defined by and extending through one of the outer layers 151A (top) and through two of the inner layers 151C, 151D of the PCB 150. The via-in-pad 139C may be utilized to connect an electronic or electrical component 180C disposed on the first outer layer 151A to one or more trace disposed between the two other layers 151A, 151B. Alternatively, in another example configuration a via-in pad 139C may include a hole 143F defined by and extending through one of the outer layers 151B (bottom) and through two of the inner layers 151C, 151D of the PCB 150. The via-in-pad 139F may be utilized to connect an electronic or electrical component 180F disposed on the second outer layer 151B to one or more trace disposed between the two other layers 151A, 151B.

Referring to FIGS. 21B to 21D and 23B, the hole 143 of the via-in-pad 139 that is defined in at least one of the outer layers 151A, 151B and/or one or more of the inner layers 151C, 151D may be filled with and/or plated with one or more materials 147, 149. The materials 147, 149 that are applied to and/or disposed in the hole 143 of the via-in-pad 139 may comprise a conductive material, non-conductive (electrically insulating) material, or a combination of conductive and non-conductive materials. The hole 143 of the via-in-pad 139 may be filled with a single material. It is also contemplated that the hole 143 of the via-in-pad 139 may be filled with multiple materials. For example, as illustrated in FIGS. 21B to 21D, the hole 143 of the via-in-pad 139 may include a first material 147 and a second material 149. The first material 147 may be applied to and/or disposed on the interior surface of the hole 143. The first material 147 may be applied to and/or disposed on the interior surface of the hole 143 along the entire length of the hole 143. The first material 147 may comprise a plating, metal, polymer, resin, epoxy, or similar material having conductive or non-conductive properties.

The hole 143 of the via-in-pad 139 may also include the second material 149. The second material 149 may also be disposed within the hole 143 of the via-in-pad 139. As illustrated in FIGS. 21B to 21D, an example configuration of the via-in-pad 139 includes the first material 147 disposed on the interior surface of the hole 143, the first material 147 having a thickness that defines a cylinder defining a void along the length of the hole 143, such that the first material 147 does not completely fill the hole 143. The second material 149 may then be applied within the void defined by the first material 147. The second material 149 may comprise plating, metal, polymer, resin, epoxy, or similar material having conductive or non-conductive properties. In an example configuration of the via-in-pad 139, the first material 147 may comprise conductive properties, and the second material 149 may comprise non-conductive or insulating properties, with the first material 147 configured to form an electrical connection with one or more traces disposed between the outer layers 151A, 151B of the PCB 150. Alternatively, it is also contemplated that the first material 147 may comprise non-conductive or insulating properties, and the second material 149 may comprise conductive properties, with the second material 149 configured to form an electrical connection with one or more traces disposed between the outer layers 151A, 151B of the PCB 150. While the figures show the hole 143 of the via-in-pad 139 as being filled with multiple materials, it is also contemplated that the hole 143 of the via-in-pad 139 may be filled with a single material, the material having conductive properties to form an electrical connection with one or more traces disposed between the outer layers 151A, 151B of the PCB 150.

The via-in-pad 139 may further comprise a cap 141 disposed over the opening of the hole 143 define in the outer layer 151A, 151B. The cap may also be referred to and/or described as plating. The cap 141 covers the opening in the hole 143 of the via-in-pad 139. A cap may be disposed over each opening defined in one of the outer layers 151A, 151B of the PCB 150. For example, as is illustrated in FIGS. 21A to 21D, the cap 141 may be disposed on the outer layer 151A, 151B and covering on the opening defined on the outer surface of the outer layer 151A, 151B, with a portion of the cap being coupled to and/or disposed on the outer surface of the outer layer 151A, 151B. In the example where the hole 143B of the via-in-pad 139B goes entirely through the PCB 150, a cap 141B, 141E may be disposed over the opening defined in each of the first and second outer layers 151A, 151B.

The cap 141 is configured to define an electrical connection with the material 147, 149 disposed within the hole 143 of the via-in-pad 139. More specifically, the cap 141 may form an electrical connection with the material 147, 149 within the hole 143 that comprises the conductive properties, with the material 147, 149 having conductive properties forming an electrical connection between the cap 141 and the one or more traces disposed between the outer layers 151A, 151B of the PCB 150. The cap 141 may also be configured to form an electrical connection with an electronic or electrical component 180 of the PCB 150. For example, as illustrated in FIGS. 20 to 21D an electrical component 180 may be coupled to and/or electrically connected to the PCB 150 by the via-in-pad 139, and more specifically the electrical component 180 may be connected by the cap 141 of the via-in-pad 139. The cap 141 may be configured to form an electrical connection between the electrical component 180 and the material 147, 149 within the hole 143 of the via-in-pad 139, and by extension with the one or more traces disposed between the outer layers 151A, 151B of the PCB 150. A plurality of via-in-pads 139A, 139B, 139C, 139D, 139E, 139F in combination with a plurality of traces interconnecting the various via-in-pads 139A, 139B, 139C, 139D, 139E, 139F may be utilized to form connections between a plurality of electrical components 180A, 180B, 180C, 180D, 180E, 180F of the PCB 150. In the example configuration where the hole 143B of the via-in-pad 139B goes entirely through the PCB 150, a cap 141B, 141E may be disposed over the opening defined in each of the first and second outer layers 151A, 151B, with each of the caps 141B, 141E forming a connection directly between the electrical components 180B, 180E coupled to the respective caps 141B, 141E.

A protective coating 153 may be applied to the exterior surface(s) of the PCB 150, such at least the exterior surface (s) of the outer layers 151A, 151B of the PCB 150. The coating 153 may also be referred to as a film, film-coating, or film-like layer. The coating 153 applied to the exterior surface(s) of the PCB 150 may comprise one or more of the following conformal coatings: an epoxy, a polyurethane, parylene or a parylene polymer, a silicone, an acrylic, or a similar protective coating. As is illustrated in FIGS. 21A to 21D, the protective coating 153 may be applied directly to the outer layers 151A, 151B of the PCB 150. The protective coating 153 may also be applied to the via-in-pad(s) 139 of the PCB 150, such as the cap 141 of the via-in-pad(s) 139. The protective coating 153, such as a conformal coating described above, may also be applied to the electrical components 180 of the PCB 150. For example, as illustrated in FIGS. 21A to 21D, the protective coating 153 may be applied directly to the exterior surfaces of at least outer layers 151A, 151B, the exposed portion of the via-in-pad 139 (the cap 141), and the exposed portion of the electrical component 180. In an example configuration, the protective coating 153 may comprise a conformal coating known as or referred to as a parylene coating 153, the parylene coating 153 being applied directly to the exterior surfaces of at least outer layers 151A, 151B, the cap 141, and the electrical component 180. In this example, there is no additional solder mask or other protective coatings are applied to the PCB 150 between the outer layers 151A, 151B and the parylene coating 153A, 153B. The absence of solder mask and/or other protective coatings being disposed between the outer layers 151A, 151B and the parylene coating 153A, 153B provides an advantage of improved adhesion between the outer layers 151A, 151B and the parylene coating 153A, 153B. Explained differently, applying the parylene coating 153 directly to the exterior surfaces of at least outer layers 151A, 151B, provides an advantage of improved adhesion between the outer layers 151A, 151B and the parylene coating 153A, 153B. Applying the parylene coating 153 directly to the exposed portion of the via-in-pad 139 (the cap 141), and the exposed portion of the electrical component 180 can similarly provide the advantage of improved adhesion between the parylene coating 153A, 153B and the via-in-pad 139 (such as the cap 141), and/or the electrical component 180.

As discussed above, there are no traces disposed on the outer surface to of the outer layers 151A, 151B of the PCB 150. By moving the traces from the outer surface to of the outer layers 151A, 151B to being disposed below or between the outer surface(s) of the outer layers 151A, 151B, such as on the outer surfaces of the inner layer(s) 151C, 151D, a parylene coating 153 can be utilized to protect the PCB 150 during use, handling, exposure to chemicals and/or undergoing cleaning/sterilization processes without need for solder mask or another protective coating in addition to the parylene coating 153. Other such conformal coatings that may be utilized as a protective coating on the PCB 150 include acrylic coatings, polyurethan coatings, silicone coatings, UV cure coatings or other hybrid conformal coatings.

While in the example configuration described above only includes a protective coating 153, such a parylene coating to the outer layers 151A, 151B, the exposed portion of the via-in-pad 139 (the cap 141), and the exposed portion of the electrical component 180, FIG. 21D illustrates an alternate configuration of the PCB 150 that includes a second protective coating 157. For example, a second protective coating 157 may be applied to a portion of exterior surface of the outer layer 151A, 151B of the PCB 150 that surrounds the cap 141 of the via-in-pad 139. The first protective coating 153 may then be applied directly to the remaining portion of the PCB 150, the exposed portion of the via-in-pad 139 (the cap 141), the exposed portion of the electrical component 180, and the second protective coating 157. An example of the second protective coating is a solder mask. This configuration of using a first and second protective coating may be advantageous for some very small electrical components 180 with very low pitch there might be a risk of shortcuts between the cap 141 of the via-in-pad 139 without the second protective coating, e.g. solder mask barrier, applied to a small portion of the exterior surface of the outer layer 151A, 151B of the PCB 150 that surrounds the cap 141 of the via-in-pad 139. In those situations, one could apply a thin (~70 μm) barrier of solder mask 157 around the cap 141 of the via-in-pad 139. Compared to the much bigger area of the PCB 150 without solder mask 157, this small area of the PCB 150 including both the first and second protective coating 153, 157 would not cause any issues even if there would be no adhesion from the first protective coating 153, e.g. parylene coating, to the areas with the second protective coating 157, e.g. solder mask.

Figure 22:
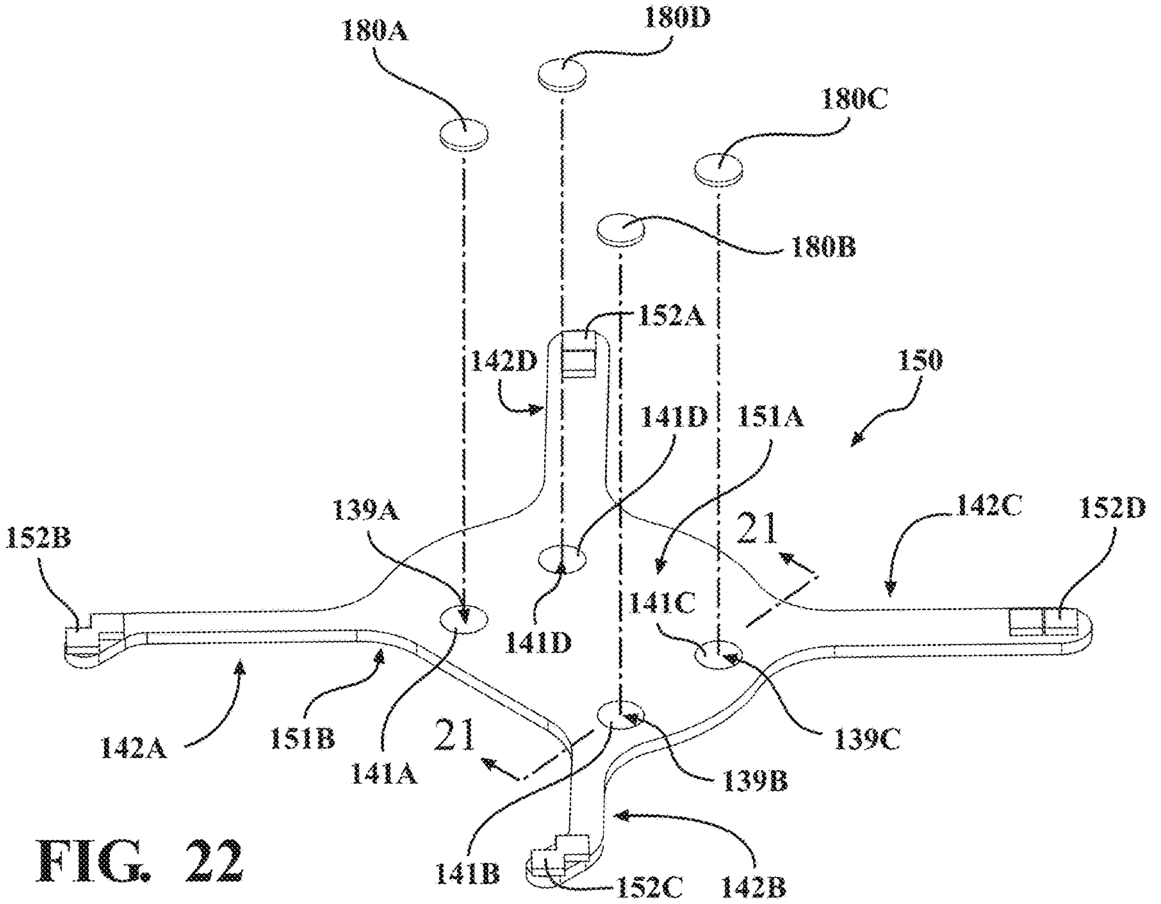
FIG. 22 is a perspective of a second configuration of a printed circuit board, the printed circuit board including via-in-pad arrangements for connecting an electronic or electrical component to traces disposed between the outer surfaces of the printed circuit board.
Figure 23B:
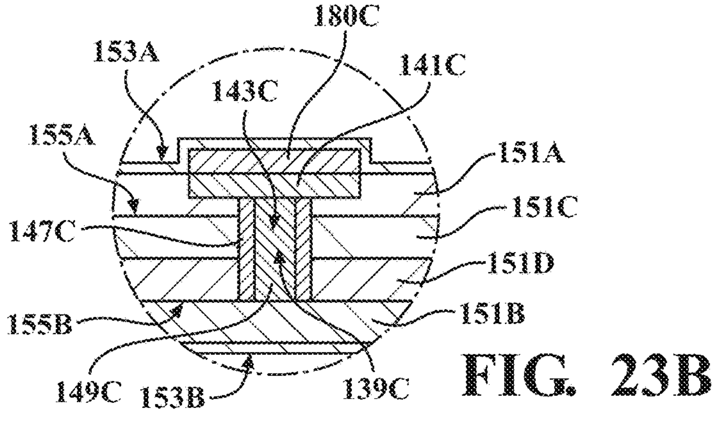
FIG. 23B is an enhanced section view of a via-in-pad arrangement of the printed circuit board of FIG. 23A.

Referring to FIGS. 22 to 23B, an example of a PCB 150 as described above is illustrated showing an alternative configuration of the via-in-pad 139 arrangement. The via-in-pad 139 may be configured to include all the same features and functionality as described above, however, at least a portion of the cap 141 of the via-in-pad 139 may be recessed within the outer layer 151A, 151B. As illustrated FIGS. 22 to 23B, the outer layer 151A, 151B of the PCB 150 may define a recess for receiving at least a portion of the cap 141 of the via-in-pad 139. This may allow top surface of the cap 141 to mounted flush, or close to flush with the exterior surface of the outer layer 151A, 151B of the PCB 150. The electronic or electrical component 180 may then still be disposed on and/or coupled to the cap 141 to form an electrical connection between the electrical component 180 and the via-in-pad 139, and by extension to the traces of the PCB 150.

F. Method of Manufacturing a Sterilizable Surgical Device

Figure 24:
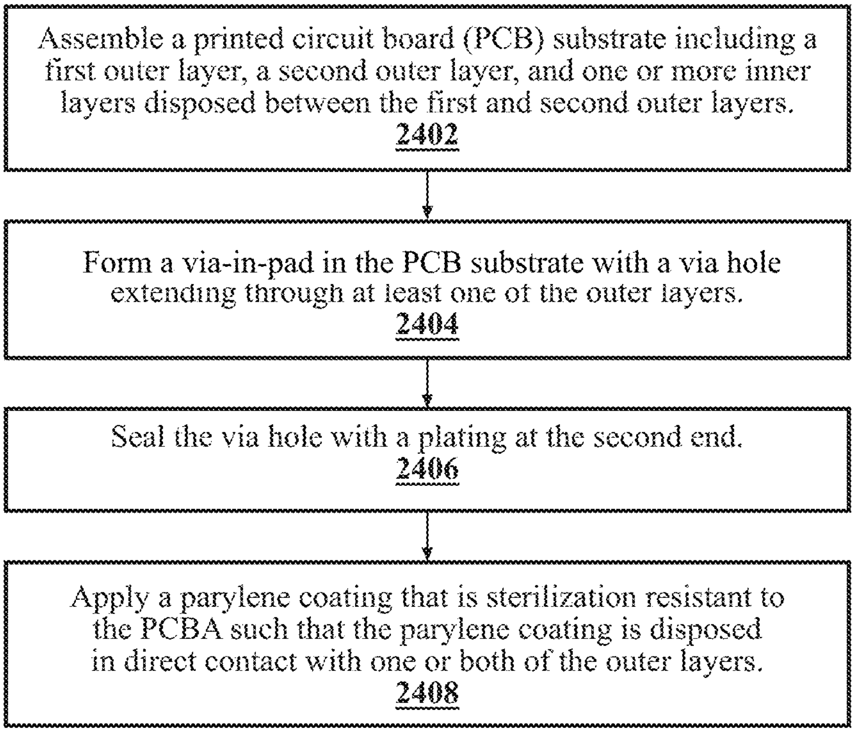
FIG. 24 is a flow chart illustrating a method of manufacturing a sterilizable printed circuit board assembly (PCBA).
Figure 25:
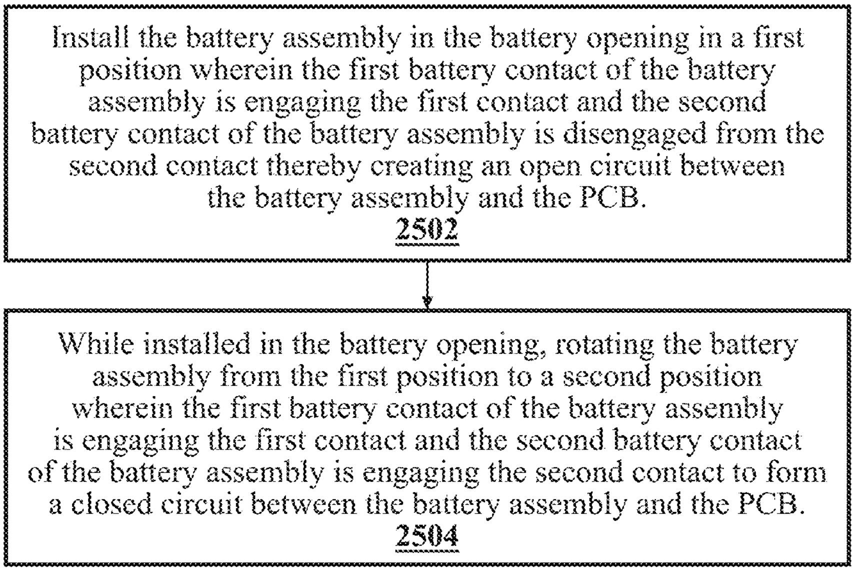
FIG. 25 is a flow chart illustrating a method of installing a battery assembly to a surgical tracker.

Referring to FIG. 24, a method of manufacturing a sterilizable printed circuit board assembly (PCBA) 30, 150 is illustrated. The method includes assembling a printed circuit board (PCB) substrate 150 including a first outer layer 151A, a second outer layer 151B, and one or more inner layers 151C, 151D disposed between the first and second outer layers. The method also includes forming a via-in-pad 139 in the PCB substrate 150 with a via hole 143 extending through at least one of the outer layers 151. The method also includes sealing the via hole with a plating or cap 141 at the second end. The method also includes applying a parylene coating 153 that is sterilization resistant to the PCBA 30, 150 such that the parylene coating 153 is disposed in direct contact with one or both of the outer layers 151A, 151B.

The method may also further comprise applying the parylene coating 153 directly to PCBA 150 without a solder mask 157 being applied to the PCBA 150 for increasing adhesion of the parylene coating 153 to the PCBA 150. This may include applying the parylene coating 153 directly to PCBA 150 such that the parylene coating 153 is solely the only coating applied to the PCBA 150. This may also include applying the parylene coating 153 such that the parylene coating 153 is disposed in direct contact with both of the outer layers 151A, 151B and the plating/cap 141.

The method of manufacturing a sterilizable printed circuit board assembly (PCBA) 30, 150 may also comprise a step of disposing a surface cap over the plating; and applying the parylene coating in direct contact with the surface cap. As describe above, the surface cap may be at least partially disposed on top of one of the exterior surfaces of the outer layers 151A, 151B of the PCB 150.

The method of manufacturing a sterilizable printed circuit board assembly (PCBA) 30, 150 may also comprise a step of forming the via hole 143 such that an interior surface of the via hole is plated with a conductive material 147, 149; and filling the via hole with a non-conductive material 147, 149.

The method of manufacturing a sterilizable printed circuit board assembly (PCBA) 30, 150 may also comprise a step of filling the via hole 143 with a conductive material 147, 149.

The method of manufacturing a sterilizable printed circuit board assembly (PCBA) 30, 150 may also comprise a step of sealing the via hole with the plating at the second end such that the plating is integrated and flush with the one of the outer layers or such that the plating is disposed on top of one of the outer layers.

The method of manufacturing a sterilizable printed circuit board assembly (PCBA) 30, 150 may also comprise a step of attaching an electronic or electrical component to the PCBA and electrically connecting the electronic or electrical component to the via-in-pad.

The method of manufacturing a sterilizable printed circuit board assembly (PCBA) 30, 150 may also comprise a step of applying the parylene coating such that the parylene coating covers at least a portion of the electronic or electrical component.

The method of manufacturing a sterilizable printed circuit board assembly (PCBA) 30, 150 may also comprise a step of forming one or more conductive traces in or on the inner layers of the PCB; and maintaining an exterior surface of the outer layers of the PCB to be absent of any conductive traces.

The method of manufacturing a sterilizable printed circuit board assembly (PCBA) 30, 150 may also comprise a step of applying a solder mask directly to a portion of the first and second outer layers surrounding the via-in-pad, the parylene coating being in direct contact with a remaining portion of the first and second outer layers and is applied over the solder mask.

It will be further appreciated that the terms “include,” “includes,” and “including” have the same meaning as the terms “comprise,” “comprises,” and “comprising.” Moreover, it will be appreciated that terms such as “first,” “second,” “third,” and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical tracker comprising:

a tracker body comprising a first surface, a second surface spaced from and opposite the first surface, and a side surface defined between the first and second surfaces, the tracker body defining a chamber formed within the first surface, second surface, and side surface;

a plurality of apertures formed in the first surface of the tracker body;

a plurality of openings formed in the side surface;

at least one channel formed in the tracker body, each of the at least one channel extending from the chamber and terminating at one of the plurality of openings formed in the side surface of the tracker body;

a printed circuit board (PCB) being located within the chamber of the tracker body and configured to support a plurality of markers that are actively energizable through the PCB, each of the plurality of markers being visible through one of the plurality of apertures of the tracker body; and wherein the tracker body is configured to be sterilizable with the PCB being located within the chamber of the tracker body, and wherein each of the at least one channel and each of the plurality of openings formed in the side surface are configured to enable sterilization fluid to enter into and drain from the chamber of the tracker body during sterilization to sterilize the PCB.

2. The surgical tracker of claim 1, wherein the tracker body defines at least three tracker body arms.

3. The surgical tracker of claim 2, wherein each of the tracker body arms defines at least one of the plurality of apertures formed in the first surface.

4. The surgical tracker of claim 2, wherein the at least one channel comprises a plurality of channels, and wherein one of the plurality of channels is formed in each of the tracker body arms of the tracker body.

5. The surgical tracker of claim 4, wherein each of the tracker body arms comprises a distal end and each of the at least one channel formed in each of the tracker body arms extends from the chamber to the distal end of the tracker body arm.

6. The surgical tracker of claim 1, wherein the PCB and the tracker body have similar shapes.

7. The surgical tracker of claim 1, wherein the PCB comprises a plurality of PCB arms and each of the plurality of PCB arms is configured to support one of the plurality of markers.

8. The surgical tracker of claim 7, wherein each of the plurality of PCB arms is disposed in one of the at least one channel formed in the tracker body and each of the plurality of markers is positioned on each of plurality of the PCB arm to occupy one of the plurality of apertures formed in the first surface.

9. The surgical tracker of claim 1, wherein the PCB comprises a protective coating to protect the PCB during sterilization, the protective coating comprising a parylene coating.

10. The surgical tracker of claim 1, wherein the tracker body comprises a first body member including the first surface and a second body member including the second body surface, each of the first body member and the second body member defining a portion of the side surface defined between the first surface and second surface; and wherein at least one of the plurality of openings formed in the side surface is formed in the portion of the side surface defined by the second body member.

11. The surgical tracker of claim 1, wherein each one of the plurality of apertures of the tracker body is substantially occupied by one of the markers.

12. The surgical tracker of claim 1, wherein the PCB comprises an infrared (IR) communication receiver.

13. The surgical tracker of claim 1, wherein the PCB comprises an IR LED that is separate from the markers and configured to communicate with a camera of a surgical navigation system.

14. The surgical tracker of claim 1, wherein the PCB comprises a line-of-sight (LOS) indicator that is configured to be controlled to indicate presence and/or absence of a line-of-sight communication from any one or more of the markers to a camera of a surgical navigation system.

15. The surgical tracker of claim 1, further comprising a battery opening defined in the second surface of tracker body that is configured to receive a battery assembly, a battery removably couplable to the tracker body via that battery opening.

16. The surgical tracker of claim 15, further comprising:

a first electrical contact and a second electrical contact disposed in the battery opening and being connected to the PCB, the first electrical contact and the second electrical contact configured to engage opposing battery contacts of the battery assembly to form an electrical connection between the battery assembly and the PCB when the battery assembly is disposed in the battery opening.

17. A surgical tracker comprising:

a tracker body comprising a first surface, a second surface spaced from and opposite the first surface, and a side surface defined between the first and second surfaces, the tracker body defining a chamber formed within the first surface, second surface, and side surface;

a plurality of openings formed in the side surface; and at least one channel formed in the tracker body, each of the at least one channel extending between the chamber and one of the plurality of openings formed in the side surface of the tracker body;

a printed circuit board (PCB) being configured to support a plurality of markers that are actively energizable through the PCB, the PCB being located within the chamber of the tracker body and each of the plurality of markers being disposed within one of the at least one channel formed in the tracker body; and wherein each of the plurality of openings with one of the at least one channel form a fluid pathway between the chamber and an external environment allowing sterilization fluid to enter and drain from the chamber of the assembled tracker body through one of the plurality of openings to sterilize the PCB located within the chamber of the tracker body.

18. The surgical tracker of claim 17, further comprising a plurality of apertures formed in the first surface of the tracker body, each of the plurality of markers positioned within the tracker body to be visible through one of the plurality of apertures defined in the first surface of the tracker body.

19. The surgical tracker of claim 18, wherein the PCB further comprises a plurality of PCB arms, each of the plurality of PCB arms is disposed within one of the at least one channel and is configured to support one of the plurality of markers;

wherein each of the plurality of markers is disposed on one of the plurality of PCB arms such that each of the plurality of markers is positioned at a distal end of one of the at least one channel and is visible through one of the plurality of apertures.

* * * * *